(12) United States Patent
Silver

(10) Patent No.: US 8,129,121 B2
(45) Date of Patent: Mar. 6, 2012

(54) REGULATION OF LIPID DROPLET FORMATION BY MODULATION OF FIT1 AND FIT2 AND USES THEREOF

(75) Inventor: David L. Silver, New York, NY (US)

(73) Assignees: Albert Einstein College of Medicine of Yeshiva University, Bronx, NY (US); The Trustees of Columbia University in the City of New York, New York, NY (US)

(*) Notice: Subject to any disclaimer, the term of this patent is extended or adjusted under 35 U.S.C. 154(b) by 281 days.

(21) Appl. No.: 12/448,840

(22) PCT Filed: Jan. 8, 2008

(86) PCT No.: PCT/US2008/000258
§ 371 (c)(1),
(2), (4) Date: Nov. 20, 2009

(87) PCT Pub. No.: WO2008/088694
PCT Pub. Date: Jul. 24, 2008

(65) Prior Publication Data
US 2010/0095391 A1    Apr. 15, 2010

Related U.S. Application Data

(60) Provisional application No. 60/880,279, filed on Jan. 12, 2007.

(51) Int. Cl.
*C12Q 1/68*       (2006.01)
*A61K 51/00*    (2006.01)
*C12N 15/11*    (2006.01)

(52) U.S. Cl. .............. 435/6.13; 514/44 A; 424/1.65
(58) Field of Classification Search ................ None
See application file for complete search history.

(56) References Cited

OTHER PUBLICATIONS

Kadereit et al., Evolutionarily conserved gene family important for fat storage, PNAS Jan. 8, 2008, 105(1):94-99.
AK043244, Mus musculus 7 days neonate cerebellum cDNA, Oct. 3, 2006, 5 pages, http:www.ncbi.nlm.nih.gov/entrez/viewer.fcgi?db=Nucleotide&dopt=GenBank&val=AK043244.
Motojima et al., A metabolic Switching Hypothesis for the First Step in the Hypolipidemic Effects of Fibrates. Biol. Pharm. Bull. 2002, 25(11):1509-1511.
PCT Notification of Transmittal of the International Search Report and The Written Opinion of The International Searching Authority, or the Declaration dated Sep. 17, 2008 by the U.S. Patent Office in connection with PCT International Patent Application No. PCT/US2008/00258, 11 pages.
International Preliminary Report on Patentability dated Jul. 14, 2009.

*Primary Examiner* — Doug Schultz
(74) *Attorney, Agent, or Firm* — Amster, Rothstein & Ebenstein LLP

(57) ABSTRACT

This invention provides methods of regulating fat storage in tissue by modulating the levels of Fibrate Induced Transcript 1 (FIT1) and/or Fibrate Induced Transcript 2 (FIT2), as well as diagnostic screens for disorders and conditions involving regulation of fat storage in tissue, assays for identifying agents that can regulate fat storage in tissue through modulating the levels of FIT1 and/or FIT2, and genetically altered mammals in which expression of FIT1 and/or FIT2 is altered in one or more tissue.

14 Claims, 23 Drawing Sheets

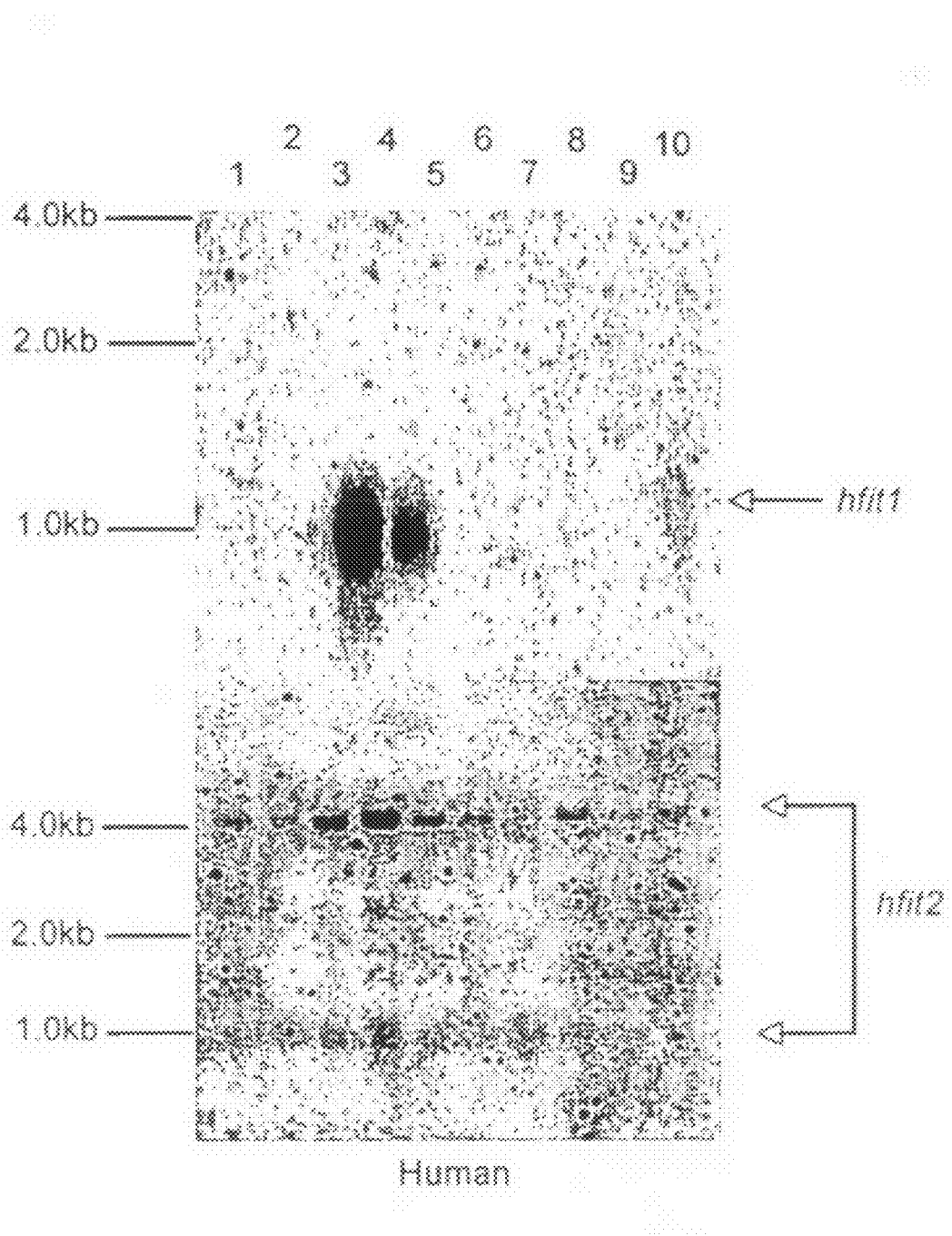

Figure 1D mFIT1

```
  1 MERGPTVGAG LGAGTRVRAL IGCLVKVLLW VASALLYFGS EQAARLLGSP CLRRLYHAWL  60
 61 AAVVIFGPLL QFHVNSRTIF ASHGNFFNIK FVNSAWGWTC TFLGGFVLLV VFLATRRVAV 120
121 TARHLSRLVV GAAVWRGAGR AFLLIEDLTG SCFEPLPQGL LLHELPDRKS CLAAGHQWRG 180
181 YIVSSHTFLL TFCCLLMAEE AAVFAKYLAH GLPAGAPLRL VFLLNVLLLG IWNFLLLCTV 240
241 IYFHQYTHKV VGAAVGTFAW YLTYGSWYHQ PWSPGIPGHG LFPRSRSMRK HN
``` mFIT2

```
  1 MEHLERCAWF LRGTLVRATV RRHLPWALVA AMLAGSVVKE LSPLPESYLS NKRNVLNVYF  60
 61 VKLAWAWTVC LLLPFIALTN YHLTGKTSLV LRRLSTLLVG TAIWYICTAL ESNIEHYTGS 120
121 CYQSPALEGI RQEHRSKQQC HREGGFWHGF DISGHSFLLT FCALMIVEEM AVLHEVKTDR 180
181 GHHLHAAITT LVVALGFLTF WVWMFLCTA VYFHDLTQKV FGTMFGLLGW YGTYGYWYLK 240
241 SFSPGLPPQS CSLTLKRDTY KK
```

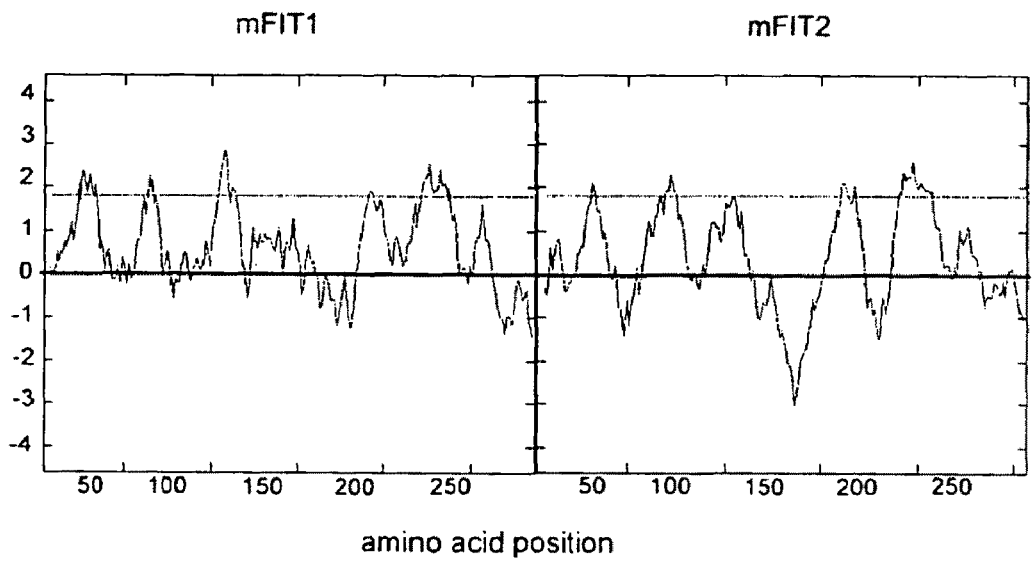

B

C

REGULATION OF LIPID DROPLET FORMATION BY MODULATION OF FIT1 AND FIT2 AND USES THEREOF

CROSS-REFERENCE TO RELATED APPLICATIONS

This application is a U.S. national stage entry under 35 U.S.C. §371 of PCT International Patent Application No. PCT/US2008/000258, filed Jan. 8, 2008, and claims priority to U.S. Provisional Patent Application No. 60/880,279, filed Jan. 12, 2007, the contents of which are incorporated herein by reference in their entirety.

STATEMENT OF GOVERNMENT SUPPORT

This invention was made with government support under grant number P30-DK42196 awarded by the National Institutes of Health. The government has certain rights in the invention.

FIELD OF THE INVENTION

The invention is directed to methods of regulating fat storage in tissue by modulating the levels of Fibrate Induced Transcript 1 (FIT1) and/or Fibrate Induced Transcript 2 (FIT2), as well as to assays for identifying agents that can regulate fat storage in tissue through modulating the levels of FIT1 and/or FIT2. Preferred forms of the invention are directed to methods of reducing fat storage in tissue by decreasing the levels of FIT1 and/or FIT2, as well as to assays for identifying agents that can reduce fat storage in tissue through decreasing the levels of FIT1 and/or FIT2. The reduction of fat storage may aid in treatment of any disease that involves storage of cytoplasmic fat in droplets, such as obesity, diabetes, metabolic syndrome, fatty liver disease (steatosis and steatohepatitis), atherosclerosis, diabetic nephropathy, and hepatitis C infection. Also provided are diagnostic screens for disorders involving regulation of fat storage in tissue, which involve assaying the level of expression or activity of FIT1 and/or FIT2 in a blood, fluid, tissue or cell sample from a subject. The invention also provides genetically altered mammals in which expression of FIT1 and/or FIT2 is altered in one or more tissue.

BACKGROUND OF THE INVENTION

Throughout this application various publications are referred to in parenthesis. Full citations for these references may be found at the end of the specification immediately preceding the claims. The disclosures of these publications are hereby incorporated by reference in their entireties into the subject application to more fully describe the art to which the subject application pertains.

The ability to store energy in the form of triglyceride (TG) is conserved from *S. cerevisiae* to humans. Triglycerides are stored in the cytoplasm surrounded by a monolayer of phospholipid in distinct structures or organelles given numerous names such as lipid particles, oil bodies, adiposomes, eicosasomes, and more commonly lipid droplets (1). Under normal physiological conditions, lipid droplets are involved in maintaining energy balance at the cellular and organismal level; but under conditions of extreme lipid droplet acquisition as in obesity, type II diabetes and cardiovascular diseases may ensue (2-6).

Recently, a great body of information has been generated revealing details of the composition and functions of many of the components of lipid droplets from *S. cerevisiae* (7), *drosophila* and mammalian cells (8-10). In mammalian cells, the catabolism of lipid droplets is a highly regulated process involving hormonal signals, droplet structural proteins and lipases (2, 11, 12). While much has been learned about the components and catabolism of lipid droplets, the molecular mechanism of lipid droplet biogenesis remains unknown. The identification of many components of lipid droplets has not revealed obvious proteins that would be involved in their formation. A widely accepted model of lipid droplet biogenesis involves the budding of a single leaflet of the endoplasmic reticulum (ER) membrane with a newly forming core or "lens" of triglyceride (1). The evidence that cytosolic lipid droplets are derived from the ER is based on the findings that some lipid droplet associated proteins are also associated with the ER membrane, and in many instances lipid droplets have been shown to be in close association with the ER membrane (8, 13-16).

The occurrence of obesity is approaching epidemic proportions. Many of the diseases associated with obesity, namely diabetes, hepatic steatohepatitis and atherosclerosis are the result of inappropriate storage of fat. Thus, there is a need for means that can effectively reduce fat storage in human tissues.

SUMMARY OF THE INVENTION

The present invention provides methods of reducing fat storage in a subject by administering to the subject an amount of an agent that is effective to decrease the level of FIT1 and/or FIT2 in the subject.

The invention also provides methods of increasing fat storage in a subject by administering to the subject an amount of an agent that is effective to increase the level of FIT1 and/or FIT2 in the subject.

The invention also provides methods of screening for a disorder involving regulation of fat storage in tissue, the methods comprising determining the level of expression and/or activity of FIT1 and/or FIT2 in a blood, body fluid, tissue biopsy or cell sample from a subject, wherein alternation from normal of the level of expression or activity of FIT1 and/or FIT2 is indicative of a disorder involving regulation of fat storage in tissue.

The invention provides methods for screening for candidate agents that can reduce fat storage in tissue by determining whether or not an agent is effective to decrease the level of FIT1 and/or FIT2 in tissue or cells, wherein the method comprises contacting an agent with a cell line or tissue culture that expresses FIT1 and/or FIT2, and wherein reduction in expression and/or activity of FIT1 and/or FIT2 is indicative that the agent is a candidate agent for reducing fat storage in tissue.

The invention also provides methods for screening for candidate agents that can increase fat storage in tissue by determining whether or not an agent is effective to increase the level of FIT1 and/or FIT2 in tissue or cells, wherein the method comprises contacting an agent with a cell line or tissue culture that expresses FIT1 and/or FIT2, and wherein an increase in expression and/or activity of FIT1 and/or FIT2 is indicative that the agent is a candidate agent for increasing fat storage in tissue.

The invention also provides transgenic mammals in which FIT1 and/or FIT2 is overexpressed in one or more tissue. The invention further provides mammals that have been genetically altered so that expression of FIT1 and/or FIT2 is reduced in one or more tissue.

BRIEF DESCRIPTION OF THE FIGURES

FIG. 1A-1D. Analysis of FIT gene expression. (A) Total RNA (15 μg) from mouse tissues were subjected to Northern blot analysis for murine FIT1 and FIT2 (mfit1 and mfit2). The tissues analyzed were as follows: 1, brain; 2, eye; 3, heart; 4, lung; 5, liver; 6, kidney; 7, adrenal; 8, spleen; 9, skeletal muscle; 10, white adipose; 11, brown adipose; 12, ovary; 13, testis; 14, stomach. Gapdh served as a positive hybridization probe. (B) Total cell lysates (80 μg) from selected mouse tissues were subjected to Western blot analysis. The following tissues were analyzed: 1, lung; 2, heart; 3, skeletal muscle; 4, liver; 5, kidney; 6, adrenal gland; 7, white adipose tissue; 8, brown adipose tissue; 9, HEK293 cell positive control expressing FIT1 or FIT2. Calnexin served as a loading control. (C) A human RNA blot containing 2 μg of poly(A) RNA per lane (FirstChoice Human Blot 1 from Ambion) was analyzed for both fit1 and fit2 (hfit1 and hfit2) expression in the following tissues: 1, brain; 2, placenta; 3, skeletal muscle; 4, heart; 5, kidney; 6, pancreas; 7, liver; 8, lung; 9, spleen; 10, colon. (D) Amino acid sequences of murine FIT1 (SEQ ID NO:3) and FIT2 (SEQ ID NO:4) and hydropathy plots. The horizontal line (slightly below +2) indicates the average hydrophobicity.

DETAILED DESCRIPTION OF THE INVENTION

Figures 1A, 1B:
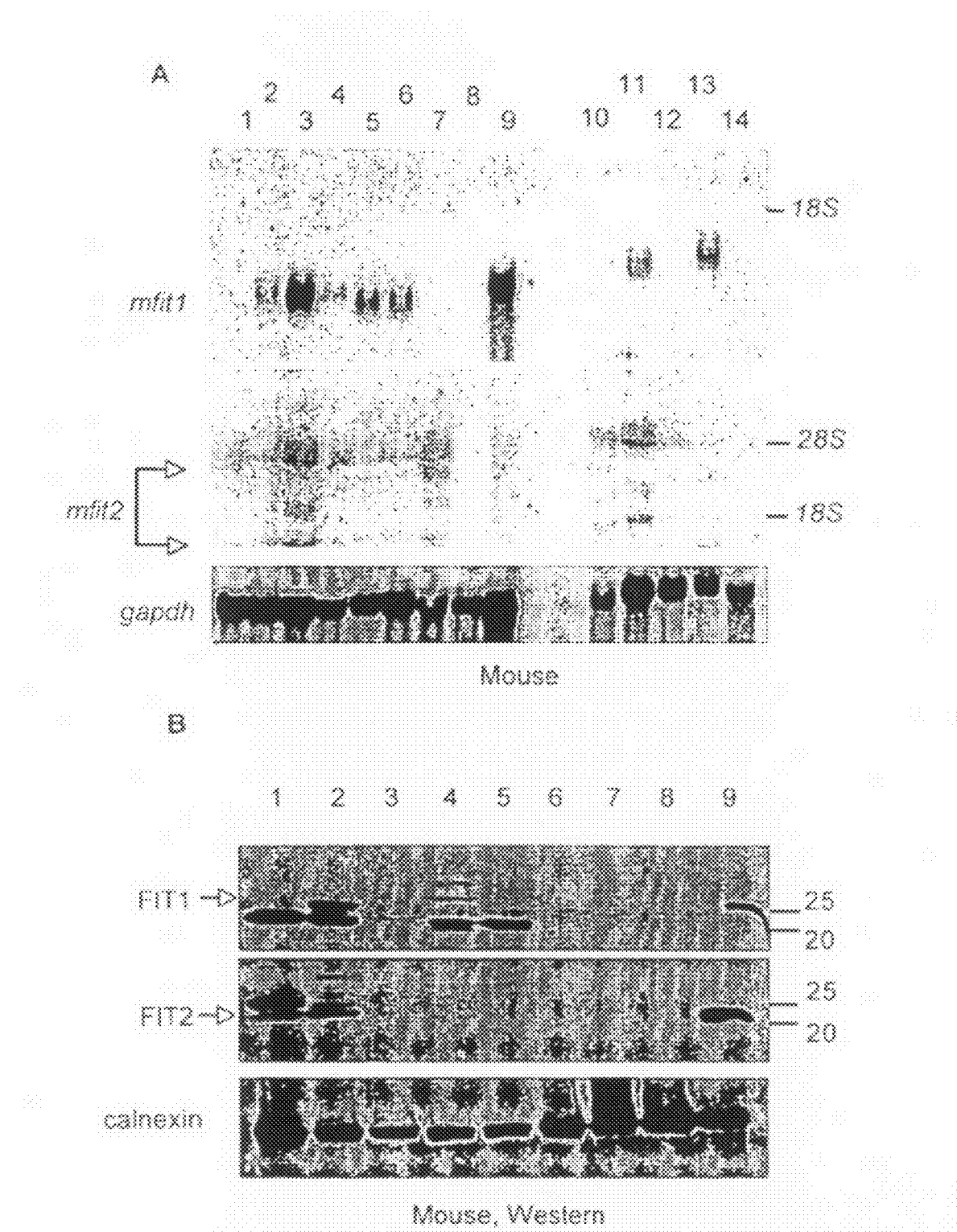

The invention provides a method of reducing fat storage in a tissue in a subject by administering to the subject an amount of an agent that is effective to decrease the level of FIT1 and/or FIT2 in the tissue in the subject. Preferably, the reduced fat storage involves reduced storage of cytoplasmic fat.

The subject can be a mammal, such as a mouse, rat, cat, dog, horse, sheep, cow, steer, bull, livestock, or monkey or other primate. Preferably, the subject is a human. The subject can have a disease involving storage of cytoplasmic fat in droplets. For example, the subject can have one or more of obesity, diabetes, metabolic syndrome, fatty liver disease, steatosis, steatohepatitis, atherosclerosis, diabetic nephropathy, and hepatitis C infection.

An examination of human tissues showed that FIT1 is primarily expressed in heart and skeletal muscle, while FIT2 is expressed in all tissues investigated (FIG. 1). Accordingly, agents that reduce FIT1 would be expected to decrease fat storage primarily in the heart and skeletal muscle, while agents that reduce FIT2 would be expected to decrease fat storage in a wide range of tissues including, for example, heart, lung, liver, kidney, brain and adipose tissue. Decreasing fat storage especially in adipose tissue would be expected to result in loss of body weight.

The methods can involve intervention at the level of DNA, RNA, and/or protein. For example, the presence or activity of FIT1 and/or FIT2 can be reduced by addition of an antisense molecule, a ribozyme, or an RNA interference (RNAi) molecule such as short hairpin RNA (shRNA), where the antisense molecule, ribozyme or RNAi molecule specifically inhibits expression of FIT1 or FIT2. The antisense molecule, ribozyme, or RNAi molecule can be comprised of nucleic acid (e.g., DNA or RNA) or nucleic acid mimetics (e.g., phosphorothionate mimetics) as are known in the art. Methods for treating tissue with these compositions are also known in the art. The antisense molecule, ribozyme or RNAi molecule can be added directly to the tissue in a pharmaceutical composition that preferably comprises an excipient that enhances penetration of the antisense molecule, ribozyme or RNAi molecule into the cells of the tissue. The antisense molecule, ribozyme or RNAi can be expressed from a vector that is transfected into the tissue. Such vectors are known in the art.

The presence or activity of FIT1 and/or FIT2 can be reduced by addition of an antibody or aptamer to the tissue, wherein the antibody or aptamer specifically binds to and reduces the activity of FIT1 or FIT2 in the tissue. The antibody or aptamer can be added directly to the tissue, preferably in a pharmaceutical composition comprising an agent that enhances penetration of the antibody or aptamer into the tissue. The antibody or aptamer can be encoded on a vector that is used to transfect the tissue. The antibody can be a polyclonal antibody or a monoclonal antibody. The antibody can be a humanized antibody. Preferably, the antibody is an internalizing antibody that is taken up by cells. The agent can be a small molecule.

The invention also provides a method of increasing fat storage in a tissue in a subject by administering to the subject an amount of an agent that is effective to increase the level of FIT1 and/or FIT2 in the tissue in the subject. The commercial compounds TZDs (e.g. rosiglitazone) can be used to increase FIT2. Increasing fat storage in tissues may be useful for treating malnutrition or for creating animal models for disease. In addition, since the anti-diabetic drugs TZDs also increase body weight and data presented herein show that they increase FIT2 in adipocytes, increased FIT2 expression in adipocytes might be part of the anti-diabetic effect of TZDs.

In different forms of the methods disclosed herein, the agent can target amino acids phenylalanine-leucine-leucine (FLL), corresponding to amino acids 157 through 159 of mouse FIT2 (mFIT2); amino acid leucine (L), corresponding to amino acid 164 of mFIT2; and/or amino acid glutamic acid (E), corresponding to amino acid 169 of mFIT2.

The invention also provides a method of screening for a disorder involving regulation of fat storage in tissue, the method comprising determining the level of expression and/or activity of FIT1 and/or FIT2 in a blood, body fluid, tissue biopsy or cell sample (e.g., skin cells) from a subject, wherein alternation from normal of the level of expression or activity of FIT1 and/or FIT2 in the sample is indicative of a disorder involving regulation of fat storage in tissue. For example, the assays can involve measuring the level of FIT1 and/or FIT2 mRNA expression, the level of FIT1 and/or FIT2 protein, or FIT1 and/or FIT2 protein activity levels. In different examples, the expression or activity of FIT1 and/or FIT2 is increased or decreased in comparison to the level found in subjects not having a disorder involving regulation of fat storage. The disorder may be; for example, obesity, type 2 diabetes, metabolic syndrome, fatty liver disease (steatosis and steatohepatitis), atherosclerosis, diabetic nephropathy, hepatitis C infection, viral infection, or a disorder of cardiac, kidney, muscle or liver function.

The invention also provides a method for screening for a candidate agent that can reduce fat storage in tissue by determining whether or not the agent is effective to decrease the level of FIT1 and/or FIT2 in tissue or cells, wherein the method comprises contacting the agent with cells or tissue that express FIT1 and/or FIT2, and wherein reduction in expression and/or activity of FIT1 and/or FIT2 is indicative that the agent is a candidate agent for reducing fat storage in tissue.

The invention further provides a method for screening for a candidate agent that can increase fat storage in tissue by determining whether or not the agent is effective to increase the level of FIT1 and/or FIT2 in tissue or cells, wherein the method comprises contacting the agent with a cells or tissue that express FIT1 and/or FIT2, and wherein an increase in expression and/or activity of FIT1 and/or FIT2 is indicative that the agent is a candidate agent for increasing fat storage in tissue.

To screen for activators or inhibitors of FIT1 or FIT2, mammalian, insect, or yeast cells can be stably or transiently transfected with FIT1 or FIT2 gene under regulated control (such as the tet-on system) or constitutively active regulation. FIT1 and FIT2 expressing cells can be treated with molecules such as chemicals, proteins, nucleic acids (e.g., RNAi, antisense oligonucleotides (ASO), aptamers) and then or prior to treatment FIT1 and FIT2 expression is induced. Cells can be screened for fluorescence of lipid droplets (automated using a fluorimeter, facs sorter, microscope with camera, or manually visibly) by incubating cells with BODIPY 492/503 or Nile red, or other lipophilic dye (specific for neutral lipids such as oil-red-o). Alternatively, cellular neutral lipids can be screened by mass measurements of lipids (e.g., using TLC, mass spec, gas chromatography). Compounds that result in cells having enhanced fluorescent signals or neutral lipid mass will be considered as activators and further studied/ verified. Compounds that result in cells having decreased fluorescent signals or neutral lipid mass will be considered as inhibitors and further studied/verified.

The following is a description of a specific example of a protocol that can be used to screen for small molecule inhibitors of FIT proteins. Infect NIH-3T3 L1 preadipocytes in 96 well plates with adenoviruses ($1\times10^8$ particles per ml) expressing either FIT1 or FIT2 for 2 hours in normal growth media (DMEM). Remove virus and incubate cells in normal growth conditions (37 deg C., 5% $CO_2$ chamber) overnight. Next day, a single species of chemical will be added to individual wells and incubated for 24 hrs. The next day the presence of lipid droplets will be detected by adding 20 µg/ml of BODIPY 492/503 lipid stain for 20 minutes. Cells will be washed and imaged using a fluorimeter or fluorescent microscope. Drugs or agents that are effective in blocking lipid droplet formation are those that result in a decrease in fluorescence signal at a wavelength of 510-665 nm. Drugs or agents that are identified through this screen can be further analyzed for specificity toward FIT proteins and cytotoxicity.

In addition, mouse embryo fibroblasts isolated from FIT2 knockout embryos may also serve as a suitable model for the screening methods described herein. These fibroblasts can be stably or transiently transfected with FIT1 and/or FIT2 under the control of regulated or constitutively active promoters. These cells may have the advantage over other cell types because they do not have endogenous FIT2 or FIT1 expression and thus have lower "background" lipid droplet formation.

The cell culture screens for activator and inhibitors of FIT 1 and FIT2 can use, for example, human FIT1 and/or human FIT2 genes or mouse FIT1 and/or TIF2 genes.

The invention also provides a transgenic mammal in which FIT1 and/or FIT2 is overexpressed in one or more tissue. Preferably, fat storage is increased in the tissue compared to a wild-type mammal. For example, FIT1 and/or FIT2 can be overexpressed in the liver, heart, and/or skeletal muscle. As another example, FIT2 can be overexpressed in adipose tissue. The adipose tissue can be white and/or brown adipose tissue. The invention further provides a mammal that has been genetically altered so that expression of FIT1 and/or FIT2 is reduced in one or more tissue. Preferably, fat storage is reduced in the tissue in comparison to a wild-type mammal. For example, the mammal can be a FIT1 knockout or FIT1 conditional knockout or can be heterozygous for FIT1. The mammal can also be heterozygous for FIT2 or be a FIT2 conditional knockout. The mammal can be a non-human mammal such as a mouse.

This invention will be better understood from the Experimental Details that follow. However, one skilled in the art will readily appreciate that the specific methods and results discussed are merely illustrative of the invention as described more fully in the claims that follow thereafter.

EXPERIMENTAL DETAILS

Materials and Methods

Reagents. FirstChoice Human Blot 1 (purchased from Ambion, cat#3140). Mouse total RNA was extracted from C57BL/6J mice and 15 µg of total RNA was used for Northern blot analysis. Rabbit polyclonal antibodies were raised against peptides corresponding to the C-terminal 15 amino acids of murine FIT1 and FIT2. Anti-V5 antibodies were purchased from Invitrogen Corporation. Full length FIT1 and FIT2 cDNAs were amplified from cDNA generated from mouse liver RNA using Thermoscript RT with polyDT primers (Invitrogen Corporation), followed by subcloning into pcDNA3.1 Directional TOPO (Invitrogen Corporation). BODIPY 493/503 and Nile Red were purchased from Invitrogen Corporation and used at 10 µg/ml.

Mice and gene arrays. 3 male wild-type mice and 3 male PPARalpha−/− mice (purchased from Jackson labs, Bar Harbor, Me.) were fed a chow diet containing 0.2% fenofibrate (purchased from Sigma-Aldrich) for 7 days. After day 7, mice were euthanized and liver RNA extracted. RNA from the 3 wild-type mice and 3 PPARalpha−/− mice were pooled in equal proportions to create 2 pools of RNA (wild-type versus PPARalpha−/−). RNA was processed by standard Affymetrix protocols to screen the MG_430 2.0 mouse gene expression array.

Figure 6:
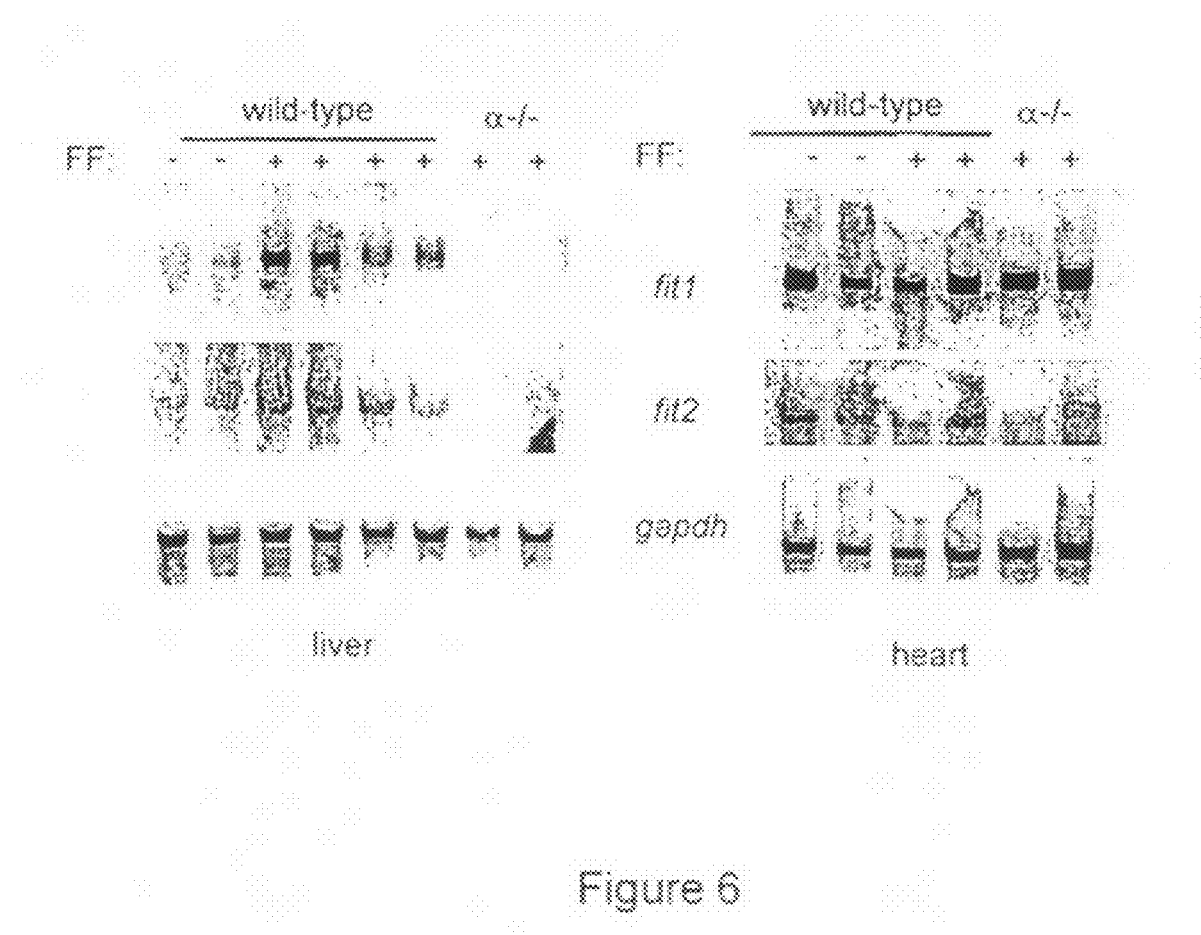
FIG. 6. Fenofibrate induction of FIT1 and FIT2 in mouse liver and heart. Mice were fed fenofibrate (FF) as described in materials and methods. Total RNA (15 μg) was subjected to Northern blot analysis. PPARalpha deficient mice (α−/−) served to demonstrate dependence of induction on PPARalpha. GAPDH served as a loading control.

Manual analysis of the gene array data revealed the presence of sequence 1451488 on the array (See Affymetrix data file at Gene Expression Omnibus) to be induced in the wild-type mice relative to the PPARalpha−/− mice. 1451488 corresponds to gene bank accession number NM_026808. Using the BLAST search algorithm by NCBI, FIT2 (Affymetrix number 1454935 and accession number NM_173397) and many other FIT orthologs were identified (FIG. 6). Sequence alignments were made using the publicly accessed program ClustaW.

Cell culture. HEK293, and HeLa cells were grown in DMEM 10% FBS. NIH-3T3 L1 adipocytes were a kind gift from Philip Scherer and grow and differentiated by standard methods (24).

Membrane fractionation. Mouse hearts were homogenized with 25 strokes using a dounce homogenizer in a buffer containing 10 mM Hepes pH7.4, 1 mM MgCl2 and proteinase inhibitors (Complete EDTA free, Roche) followed by 3 brief sonication pulses on ice. Nuclei were removed by a 2000×g spin for 5 min and samples were loaded on the top of a continuous sucrose gradient and centrifuged in a SW41 rotor at 100,000×g for 18 hrs. The continuous sucrose gradient was prepared by mixing a 1.1 M sucrose solution made in the above buffer used for homogenization with a 0.58M sucrose solution made in the same buffer using a standard 12 ml gradient maker. After centrifugation, the top 3 fractions (800 µl each) were discarded because of visible cellular debris. All subsequent 800 µl fractions were collected for Western blot analysis.

Confocal immunofluorescence microscopy. HEK293 cells were transiently transfected with expression plasmids for mFIT1 and mFIT2 with C-term V5 tags and RFP-KDEL. Cells were fixed with 10% formalin for 15 minutes at room temperature, followed by permeablization with 0.1% triton X-100. Cells were then blocked with Goat serum (5%) followed by consecutive incubations with anti-V5 antibody, and anti-mouse Alexa 488. After several post-antibody washes, cells were visualized by confocal microscopy using a BioRad Radiance 2000 Laser Scanning Confocal Microscope.

Human FIT expression. Human FIT2 cDNA (hFIT2) was amplified from the human hepatic cell line HepG2 using primers forward primer: 5'-CACCATGGAGCATCTG-GAGCGCTGCGAGTGGTTGTTGCG-3' (SEQ ID NO:56) and reverse primer: 5'-TTATTTCTTGTAACTATCTTGCT-TCAAATTCAAAC-3' (SEQ ID NO:57). To produce a V5-epitope tagged version of hFIT2 (hFIT2-V5) the following reverse primer was used instead of the one described above: 5'-TTTCTTGTAACTATCTTGCTTCAAAT-TCAAACTAC-3' (SEQ ID NO:58). The amplified hFIT2 cDNA was subcloned into pcDNA3.1 topo directional plasmid (Invitrogen Corp.). To test if hFIT2 and hFIT2-V5 can produce droplets, HEK293 cells were transfected with 2.4 µg of the above described plasmid expressing hFIT2 and stained 36 hr posttransfection with the lipid droplet stain BODIPY493/503. Lipid droplets were visualized by fluorescence microscopy.

TLC assays. Lipids were extracted from cells in culture using HIP: Hexane:isopropanol (3:2 V/V). Triglyceride and cholesterol ester mass was quantified using TLC according (21, 25). The TLC solvent system used was Hexane:Ethyl ether:Acetic acid (80:20:1).

Triglyceride biosynthesis and DGAT assays. Cells in culture were incubated with 7.5 µCi/mL of 14C-glycerol (Specific activity: 125-180 mCi/mmol, NEN-Amersham) for the indicated times, followed by extraction with HIP and separation by TLC as referenced above. Radioactive triglycerides were quantified using PhosphorImager analysis and represented as a rate of triglyceride production using arbitrary units obtained from PhosphorImager analysis.

Lipase activity assay. Total cellular lipase activity was measured using the established method of Holm and Osterlund in Methods in Molecular Biology 1999; 109, p 109-121.

Lentivirus shRNA. The following short hairpin RNA (shRNA) sequences (sense strand shown) were used to knockdown mouse FIT2 expression: shRNAcont, CAC-CGAATTCTCCGAACGTGTCACGC-GAACGTGACACGTTCGGAGAA (SEQ ID NO:20); shRNAFIT2, (SEQ ID NO:21) CACCGCACCATGTTTG-GTTTGTTGGCGAACCAACAAACCAAACATGGTGC.

Double stranded shRNA DNAs were used to generate lentiviruses using the U6 promoter driven BLOCK-iT Lentivirus RNAi expression system (Invitrogen Corporation). Knockdown of human FIT2 in HEK293 cells was performed by stably transfection using pEntryU6 vector (Invitrogen Corp). NIH-3T3 L1 pre-adipocytes and HepG2 cells were infected with an MOI of 10-50.

FIT2 mutations. FLL157-9 and single 164L and 169E residues were changed to alanines using standard PCR mutagenesis methods on the mouse FIT2 cDNA. Mutants were subcloned into pcDNA3.1 Topo Directional plasmid (Invitrogen corp.) for expression in HEK 293 cells. HEK 293 cells were transfected with 2 µg of DNA from each construct and cells were stained 36 hrs after transfection with BODIPY493/503 (10 µg/ml for 10 minutes) to visualize lipid droplets.

Mouse transgenic models of FIT) and FIT2 overexpression: liver-specific expression. Transgenic mice were generated that overexpress mouse FIT1 and FIT2 specifically in liver using the murine albumin promoter (Albe/p vector, kind gift from Ronald Kahn, Harvard University). FIT1 and FIT2 located in pcDNA3.1 Directional vector were digested with HindIII-EcoRV and blunt ended using Klenow enzyme. A bovine growth hormone polyadenylation sequence was amplified by PCR from pcDNA3.1 using primers containing a 5' BamH1 site and a 3' EcoRV site. This PCR product was digested with the aforementioned restriction enzymes and subcloned into Albe/p vector digested with the same enzymes and now designated Albe/p-BGH. This step introduced a necessary polyadenylation sequence. Next, the FIT1 and FIT2 blunt ended DNA fragment was subcloned into Albe/p-BGH digested with EcoRV yielding FIT1-, FIT2-Albe/p-BGH construct. This construct was then used to create transgenic mice at the Albert Einstein College of Medicine.

Mouse transgenic models of FIT1 and FIT2 overexpression: muscle-specific expression. Transgenic mice were generated that overexpress mouse FIT1 specifically in skeletal muscle using the muscle creatine kinase promoter (MCK pCK4800, kind gift from Rhonda Bassel-Duby, UT Southwestern Medical Center). The transgene was constructed by subcloning HindIII-EcoRV blunt ended FIT1 cDNAs into MCK pCK4800 digested with EcoRV to yield MCK-FIT1.

Mouse transgenic models of FIT1 and FIT2 overexpression: heart-specific expression. Transgenic mice were generated that overexpress mouse FIT1 specifically in cardiac myocytes using the alpha myosin heavy chain promoter enhancer vector (alpha-MHC vector, a kind gift of Ira Goldberg, Columbia University). To generate the transgene construct alpha-MHC vector was digested with SalI and made blunt using klenow enzyme. A HindIII-EcoRV blunt ended fragment of FIT1 was subcloned into the digested alpha-MHC vector to generate alpha-MHC-FIT1.

Mouse transgenic models of FIT1 and FIT2 overexpression: adipose-specific expression. Transgenic mice were generated that overexpress mouse FIT2 specifically in adipose tissue (white and brown adipose) using the Ap2 promoter/enhancer (kind gifts from Philip Scherer, Albert Einstein College of Medicine). To produce this transgene the 3'UTR Ap2 enhancer was digested with HindIII-EcoRV. FIT2 was digested with HindIII-EcoRV (from pcDNA3.1) and ligated into the vector containing the 3'UTR Ap2 enhancer to yield FIT2-3'UTR. The Ap2 promoter was digested with XmaI then made blunt, followed by digestion with SalI. FIT2-3'UTR was digested with HindIII and made blunt, then cut with SalI. The Ap2 digested fragment was then ligated into FIT2-3'UTR to make the final transgene Ap2-FIT2-3'UTR.

Mouse deficiency models for FIT1 and FIT2: FIT1 gene targeted mice. BAC recombineering methods were utilized according to the protocols found in Warming et al. (26) and publicly available at http://recombineering.ncifcrf.gov/. All materials obtained to perform BAC recombineering were obtained free of charge from NIH Division of Technology Development and Transfer Office (Phone: 301-435-5502). BAC RP23-186J4 (referred to as BAC J4) was purchased from Children's Hospital Oakland Research Institute. BAC J4 was electroporated into SW102 cells for further use in recombineering. Plasmid p1452 was used as template to add on 50 base pairs of homology flanking the NEO cassette located in p1452. The primer sequences are as follows: forward primer: CATTAGCCCCTCCTCAGCCTCCAGCAGAGCAGACAGTTAGTGGGGAGGGGCCAT GGccgatcatattcaataaccc (SEQ ID NO:22); reverse primer: TGTTTGCGCATTGAGCGGGATCGAGGGAAGAGCCCGTGGCCTGGGATCCCATAA CTTCGTATAGCATAC (SEQ ID NO:23). Plasmid p1452 has the sequence set forth in SEQ ID NO:54.

Purified PCR product (200 ng) was used to electroporate SW102 cells harboring BAC J4, and Kan and Chlor resistant colonies were selected for on plates (designated as BAC J4-NEO). Verification of correct targeting was carried out using the following pairs of PCR primers:

```
                              (SEQ ID NO: 24)
1) FIT1F-TVP, GTTGACCGTCAGTCCTCAAACTGGCCCCTTGC;

(SEQ ID NO: 25)
   PGK-R-TVP, GCTTGGCTGGACGTAAACTCCTCTTCAGACC;

(SEQ ID NO: 26)
2) FIT1R-TVP, GAAAAGAATCGGAGGAGACAGAGCCAGGCCTGG;

(SEQ ID NO: 27)
   BGH-F-TVP, GAACCAGCTGGGGCTCGACTAGAGCTTGCGG.
```

In addition, Southern blot analysis was performed to confirm proper targeting. BAC J4-NEO DNA was digested with NcoI and probed with a radiolabeled PCR fragment (300 bp fragment) generated using the following two PCR primers and BAC J4 as template:

NcoI-F: Acacaagttttgcacagacatagatgcagg (SEQ ID NO:28);

Nco-R: Caacttcacacagcctagaatcatctgagaggagaacc (SEQ ID NO:29).

Following confirmation that exon 1 and exon 2 were replaced by the NEO cassette from plasmid p1452, a diphtheria toxin cassette with Amp resistance, DTA (kind gift of Chingwen Yang, Rockefeller University) was homologously recombined into BAC J4-NEO. 50 bp homology arms were add by PCR to the DTA cassette using the following pair of primers:

```
FIT-DTA-F:
                              (SEQ ID NO: 30)
ACACAAGTTTTGCACAGACATAGATGCAGGTAAAATATACATAAGTAAGC

GAACAACTCCGCCGCGCGCTC;

FIT-DTA-R:
                              (SEQ ID NO: 31)
CAACTTCACACAGCCTAGAATCATCTGAGAGGAGAACCTCAATGGAGGAA

GAGTAAACTTGGTCTGACAG.
```

PCR product (200 ng) was electroporated into SW102 cells harboring the BAC J4-NEO and colonies were selected that were Chlor, Kan and Amp resistant. Targeting of the DTA cassette was verified using the following two sets of PCR primer pairs:

```
                                 (SEQ ID NO: 32)
1) FIT3F-TVP,   CAGGCTGCTCTTCAGGAGTATATCTGGGTTC;

(SEQ ID NO: 33)
   POLIIP1R-TVP, CCGGGAGCCACCTTCTTCTCCAACCGTCCCGG;

(SEQ ID NO: 34)
2) FIT3R-TVP,   AGTTACAGACAATTGTGAGTTGCCATGTGGC;

(SEQ ID NO: 35)
   AMP1F-TVP,   CTGAGATAGGTGCCTCACTGATTAAGCATTGG.
```

10 μg of BAC J4-NEO-DTA was cut with NotI to linearize and then electoporated into embryonic stem (ES) cells at the Columbia University Transgenesis facility. 45 ES cells were screened for homologous recombination using the following two PCR primers:

```
                                 (SEQ ID NO: 36)
FIT-ES1-TVP-F, GTACCCCACAGTCACATCCATAGGACAATCC;

(SEQ ID NO: 37)
FIT-ES1-R,     CTAACTGTCTGCTCTGCTGGAGGCTGAGGAGG.
```

Targeted ES cells were then confirmed by Southern blot analysis using the NcoI probe as described above. The targeted D5 ES cell line was used to generate chimeric mice. The FIT1 Knockout mice are viable and fertile.

Mouse deficiency models for FIT1 and FIT2: FIT2 gene targeted mice. BAC recombineering methods were utilized according to the protocols found in Warming et al. (26) and publicly available at http://recombineering.ncifcrf.gov/. All materials obtained to perform BAC recombineering were obtained free of charge from NIH Division of Technology Development and Transfer Office (Phone: 301-435-5502). BAC RP23-36P22 (referred to as BAC P22) was purchased from Children's Hospital Oakland Research Institute. BAC P22 was electroporated into SW105 cells for further use in recombineering to specifically delete exon2. Plasmid p1452 was used as template to add on 50 base pairs of homology flanking the NEO cassette located in p1452. The primer sequences are as follows:

```
pL452FIT2a-F,
                              (SEQ ID NO: 38)
GCTCAGAGGAGGCAGACATGGCAGATGTTGCTGTATCTGGCCTAATGAAC ccgatcatattcaataaccc;

pL452FIT2a-R,
                              (SEQ ID NO: 39)
ACGTGGGAATCCTATTAGCCATTGTCCTCCTGTCCCTATGTCCTTCTCTT ataacttcgtatagcatac.
```

Purified PCR product (200 ng) was used to electroporate SW105 cells harboring BAC P22, and Kan and Chlor resistant colonies were selected for on plates (designated as BAC P22-NEO). Verification of correct targeting was carried out using the following pairs of PCR primers:

```
                                 (SEQ ID NO: 40)
1) FIT2-TVP1c-F, TAAGAATAGAGTGTAAGGGTGGTAGTTGTTCC;

(SEQ ID NO: 25)
   PGK-R-TVP,    GCTTGGCTGGACGTAAACTCCTCTTCAGACC;

(SEQ ID NO: 41)
2) FIT2-TVP1d-F, CCTTCATCCTTCCCCACTCGTAGTGGCTGGTC;

(SEQ ID NO: 27)
   BGH-F-TVP,    GAACCAGCTGGGGCTCGACTAGAGCTTGCGG.
```

Following confirmation that exon 2 were replaced by the NEO cassette from plasmid p1452, a diphtheria toxin cassette with Amp resistance, DTA (kind gift of Chingwen Yang, Rockefeller University) was homologously recombined into BAC P22-NEO. 50 bp homology arms were add by PCR to the DTA cassette using the following pair of primers:

FIT2-DTA-F,
 (SEQ ID NO: 42)
ACAGTCCCAGCTCCCATGGCACTCCTCACTGTAAATATAACTCGCCGATG gaacaactccgccgcgcgcgctc;

FIT2-DTA-R,
 (SEQ ID NO: 43)
GCTGGCCTGGAACTCACTTTATAGAGAGGGCTGGTTTTGAACCTGTGTT

Ggagtaaacttggtctgacag.

200 ng of PCR product was electroporated into SW102 cells harboring the BAC P22-NEO and colonies were selected that were Chlor, Kan and Amp resistant. Targeting of the DTA cassette was verified using the following two sets of PCR primer pairs:

(SEQ ID NO: 44)
1) FIT2-TVP5-F, CTTCGTGCACACTAGTCAAGCATCCTACCAAC;

(SEQ ID NO: 33)
POLIIP1R-TVP, CCGGGAGCCACCTTCTTCTCCAACCGTCCCGG;

(SEQ ID NO: 45)
2) FIT2-TVP7-R, CTATTTTGAAACAGGATCTCTTACGTGACCC;

(SEQ ID NO: 35)
AMP1F-TVP, CTGAGATAGGTGCCTCACTGATTAAGCATTGG.

10 μg of BAC P22-NEO-DTA was cut with NotI to linearize and then electoporated into ES cells at the Columbia University Transgenesis facility. 48 ES cells were screened for homologous recombination by Southern blot analysis. ES cell DNA was digested in 96 well plates with NcoI and probed with a 300 bp fragment, which is the same fragment replaced by the DTA cassette on the P22 BAC. Wild-type alleles yielded a 2.8 kb fragment and targeted alleles resulted in the appearance of a 3.5 kb fragment.

The targeted A3, ES cell line was used to generate chimeric mice. It was been determined that deletion of FIT2 results in embryonic lethality and therefore conditional FIT2 targeted mice were generated as described below.

FIT2 Conditional targeted mice. Based on the finding described herein that gene targeted deletion of FIT2 results in embryonic lethality, BAC recombineering was used to produce a "foxed" allele of FIT2 to conditionally knock it out in adult mice.

The same BAC, P22 was used for generating an engineered targeting vector. For insertion of a single loxP site within intron 1 upstream of exon 2, pL451 was PCR amplified to introduce 50 bp homology arms to this region using the following primers (uppercase letters correspond to vector sequences of pL451):

FIT2pL451a-F,
 (SEQ ID NO: 46)
taatgaaccaggagcccagcagcctggcacgccaattgtttaggggtagc

GATATCGAATTC;

FIT2pL451a-R,
 (SEQ ID NO: 47)
gaaaaaaagaaagaaagaaagcgagcaagctttagttcaagctacaagac

AGTGGATCCACC.

Plasmid p1451 has the sequence set forth in SEQ ID NO:55.

200 ng of PCR product was electroporated into SW105 cells harboring the P22 BAC and cells were selected for kanamycin resistance yielding P22-NEO. Homologous recombination was verified using the following primers:

(SEQ ID NO: 48)
1) FIT2-TVPC1-R, accacatggtggctcataaccatctgtcatg;

(SEQ ID NO: 27)
BGH-F-TVP, GAACCAGCTGGGGCTCGACTAGAGCTTGCGG;

(SEQ ID NO: 49)
2) FIT2-TVP1c-F, TAAGAATAGAGTGTAAGGGTGGTAGTTGTTCC;

(SEQ ID NO: 25)
PGK-R-TVP, GCTTGGCTGGACGTAAACTCCTCTTCAGACC.

The Neo cassette was then removed from BAC-NEO by treating cells with arabinose to induce the endogenous flip recombinase resulting in a single loxP and Frt site left behind in intron 1, and also sensitivity to kanamycin. This construct is called BAC-Frt-loxP.

Next, insertion of a second loxP site downstream of exon 2 was made by PCR amplification of pL451 with the following primers:

FIT2pL451b-F,
 (SEQ ID NO: 50)
acaagcttagttggcagactctgctggcggtgccaccatgttgccagcag

GATATCGAATTC;

FIT2pL451b-R,
 (SEQ ID NO: 51)
acgatgaggcaggctgctctccctctgctgagcctcagctctccctctgg

AGTGGATCCACC.

200 ng of PCR product was electroporated into SW105 cells harboring BAC-Frt-loxP and cells were again selected for kanamycin resistance and the new recombined BAC was designated BAC-Frt-Loxp-exon2-NEO-loxP.

Homologous recombination was verified using the following primers:

(SEQ ID NO: 52)
1) FIT2-TVPC-4R, agtgagttccagaacacgcagggctacacag;

(SEQ ID NO: 27)
BGH-F-TVP, GAACCAGCTGGGGCTCGACTAGAGCTTGCGG;

(SEQ ID NO: 53)
2) FIT2-TVPC5-F, gctcagcagagggagagcagcctgcctgatcgt;

(SEQ ID NO: 25)
PGK-R-TVP, GCTTGGCTGGACGTAAACTCCTCTTCAGACC.

Following confirmation that exon 2 was flanked by both an upstream loxp-frt site and downstream loxp-neo cassette from pL451, a diphtheria toxin cassette with Amp resistance, DTA (kind gift of Chingwen Yang, Rockefeller University) was homologously recombined into BAC P22-NEO. 50 bp homology arms were add by PCR to the DTA cassette using the following pair of primers:

FIT2-DTA-F:

(SEQ ID NO: 42)
ACAGTCCCAGCTCCCATGGCACTCCTCACTGTAAATATAACTCGCCGATG gaacaactccgccgcgcgcgctc;

FIT2-DTA-R:

(SEQ ID NO: 43)
GCTGGCCTGGAACTCACTTTATAGAGAGGGCTGGTTTTGAACCTGTGTTG gagtaaacttggtctgacag.

200 ng of PCR product was electroporated into SW105 cells harboring the BAC-P22 Frt-Loxp-exon2-NEO-loxP and colonies were selected that were Chlor, Kan and Amp resistant. The completed vector is now designated BAC-P22 Frt-Loxp-exon2-NEO-loxP-DTA. Targeting of the DTA cassette was verified using the following two sets of PCR primer pairs:

(SEQ ID NO: 44)
1) FIT2-TVP5-F, CTTCGTGCACACTAGTCAAGCATCCTACCAAC;

(SEQ ID NO: 33)
POLIIP1R-TVP, CCGGGAGCCACCTTCTTCTCCAACCGTCCCGG;

(SEQ ID NO: 45)
2) FIT2-TVP7-R, CTATTTTGAAACAGGATCTCTTACGTGACCC;

(SEQ ID NO: 35)
AMP1F-TVP, CTGAGATAGGTGCCTCACTGATTAAGCATTGG.

10 µg of BAC-P22 Frt-Loxp-exon2-NEO-loxP-DTA was cut with NotI to linearize and then electoporated into ES cells at the Columbia University Transgenesis facility. ES cells will be screened for homologous recombination by Southern blot analysis. ES cell DNA will be digested in 96 well plates with NcoI and probed with a 300 bp fragment which is the same fragment replaced by the DTA cassette on the BAC-P22 Frt-Loxp-exon2-NEO-loxP-DTA. Wild-type alleles yield a 2.8 kb fragment and Neo-floxed exon 2 allele will result in the appearance of a 5.6 kb fragment. Removal of the Neo cassette by crossing Neo-foxed mice with a flip-recombinase expressing mouse line (e.g. constitutive expression driven by the beta-actin promoter available for purchase from Jackson Laboratories, Bar Harbor Me.) will result in a floxed exon 2 allele (without the neo cassette downstream of exon 2) of 6 kb. Exon 2 can be deleted in a tissue- and stage-specific manner by crossing mice to cre or flip recombinase transgenic mice with the recombinase under the control of a tissue or developmentally regulated promoter. Many of these transgenic lines expressing cre or flip are available for purchase.

Regulated promoter for FIT1 and FIT2 expression. To generate an inducible expression system for murine FIT1 and FIT2, FIT1-V5 and FIT2-V5 (both having c-terminal V5 epitopes) have been subcloned from pcDNA3.1 topo directional (plasmid from Invitrogen corp.) using restriction enzymes HindIII and PmeI into pcDNA5/TO cut with restriction enzymes HindIII and EcoRV. pcDNA5/TO contains two tetracycline operator sites in the promoter region of the plasmid that serve as binding sites for the tetracycline repressor. Induction of either FIT1 or FIT2 expression will be achieved by treating cells with 1 µg/ml of tetracycline or doxycycline. All cell lines that will be used must express the tetracycline repressor. Tetracycline repressor expressing cells will be generated by stably transfecting cells with pcDNA6/TR (from Invitrogen corp.) and selecting for G418 resistance. pcDNA6/TR harboring cells will also be made to stably harbor FIT1 and FIT2 pcDNA5/TO constructs by selection on hygromycin.

Results and Discussion

Identification of FIT genes. The initial goal was to identify genes involved in intracellular fatty acid transport toward either storage in lipid droplets as triglyceride or catabolism via beta-oxidation in peroxisomes and mitochondria. Fenofibrate and other fibrate drugs are agonists for the peroxisome proliferator-activated receptor alpha (PPARalpha) nuclear hormone receptor, and activation of PPARalpha leads to the induction of the genes coding for proteins involved in the entire biochemical repertoire of beta-oxidation (17-19). To carry out this goal, genotype matched wild-type and PPARalpha deficient mice were fed a diet containing fenofibrate for 7 days. mRNA from livers were used to query gene arrays. Since most of the genes activated by PPARalpha likely have been identified, the focus was exclusively on genes that were listed as expression sequence tags (ESTs) or having unknown function. By performing BLAST searches against the mouse genome, many of the ESTs to the 3 prime end of the final exons of genes were located. This analysis was followed by both an examination using the Signal P algorithm to determine the putative cellular location of the gene product and using Novartis SymAltas (http://symatlas.gnf.org/SymAtlas/) to determine the putative tissue expression pattern. Attention was directed toward a particular unknown transcript, named Fibrate Induced Transcript 1 (FIT1, Affymetrix number 1451488). FIT1 potentially has multiple transmembrane domains (FIG. 1D), was putatively located in the secretory pathway (determined by Signal P), and highly expressed in heart and skeletal muscle by gene array studies (determined by Novartis Gene Atlas). However, FIT1 did not have homology to known proteins or known protein domains found in any species. These characteristics indicated a protein potentially involved in lipid transport in oxidative tissues.

Figure 5A:
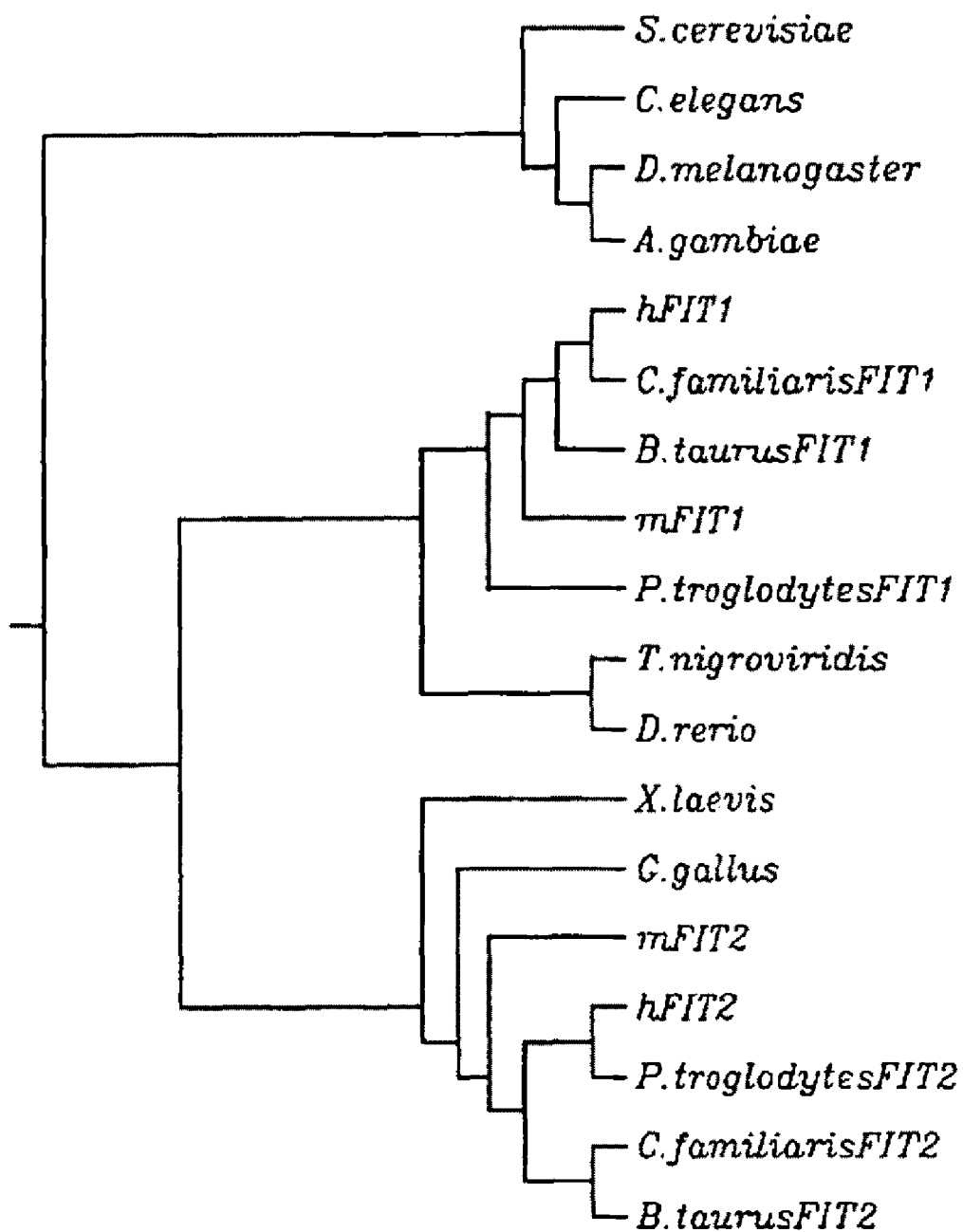
FIG. 5A-5B. Sequence alignments of FIT orthologs in multiple species. (A) Cladogram generated with ClutalW showing the amino acid sequence homologies among FIT proteins. Accession numbers for each FIT ortholog is indicated next to the cladogram. (B) Amino Acid sequence alignment of some FIT orthologs shown in A. Alignment was generated using the ClustalW algorithm. S. cerevisiae (YDR319-C, U32517, AAB64755) (SEQ ID NO:5), C. elegans (SEQ ID NO:7), D. melanogaster (SEQ ID NO:8), D. rerio (SEQ ID NO:11), X. laevis (SEQ ID NO:12), G. gallus (SEQ ID NO:13), mFIT2 (NM173397, NP775573) (SEQ ID NO:4), hFIT2 (XM371399, XP371399) (SEQ ID NO:2), hFIT1 (NM203402, NP981947) (SEQ ID NO:1), and mFIT1 (NM026808, NP081084) (SEQ ID NO:3). Additional FIT sequences are shown in the Sequence Listing: S. cerevisiae (SCS3, NP011389, NC001139) (SEQ ID NO:6), A. gambiae (SEQ ID NO:9), T. nigroviridis (SEQ ID NO:10), P. troglodytes FIT2 (SEQ ID NO:14), C. familiaris FIT2 (SEQ ID NO:15), B. taurus FIT2 (SEQ ID NO:16), P. troglodytes FIT1 (SEQ ID NO:17), C. familiaris FIT1 (SEQ ID NO:18), and B. taurus FIT1 (SEQ ID NO:19).
Figure 5B:
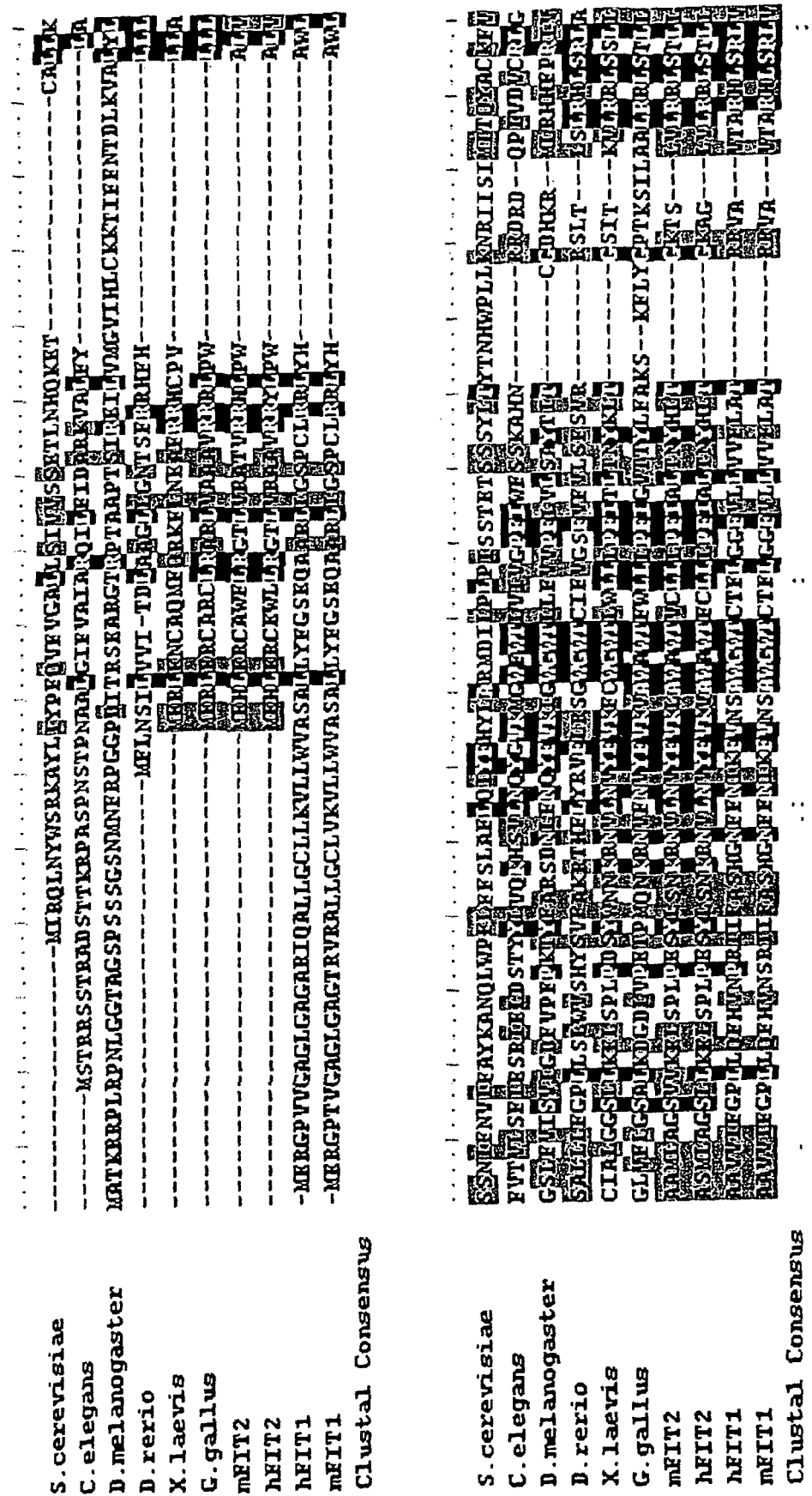
Figure 5B:
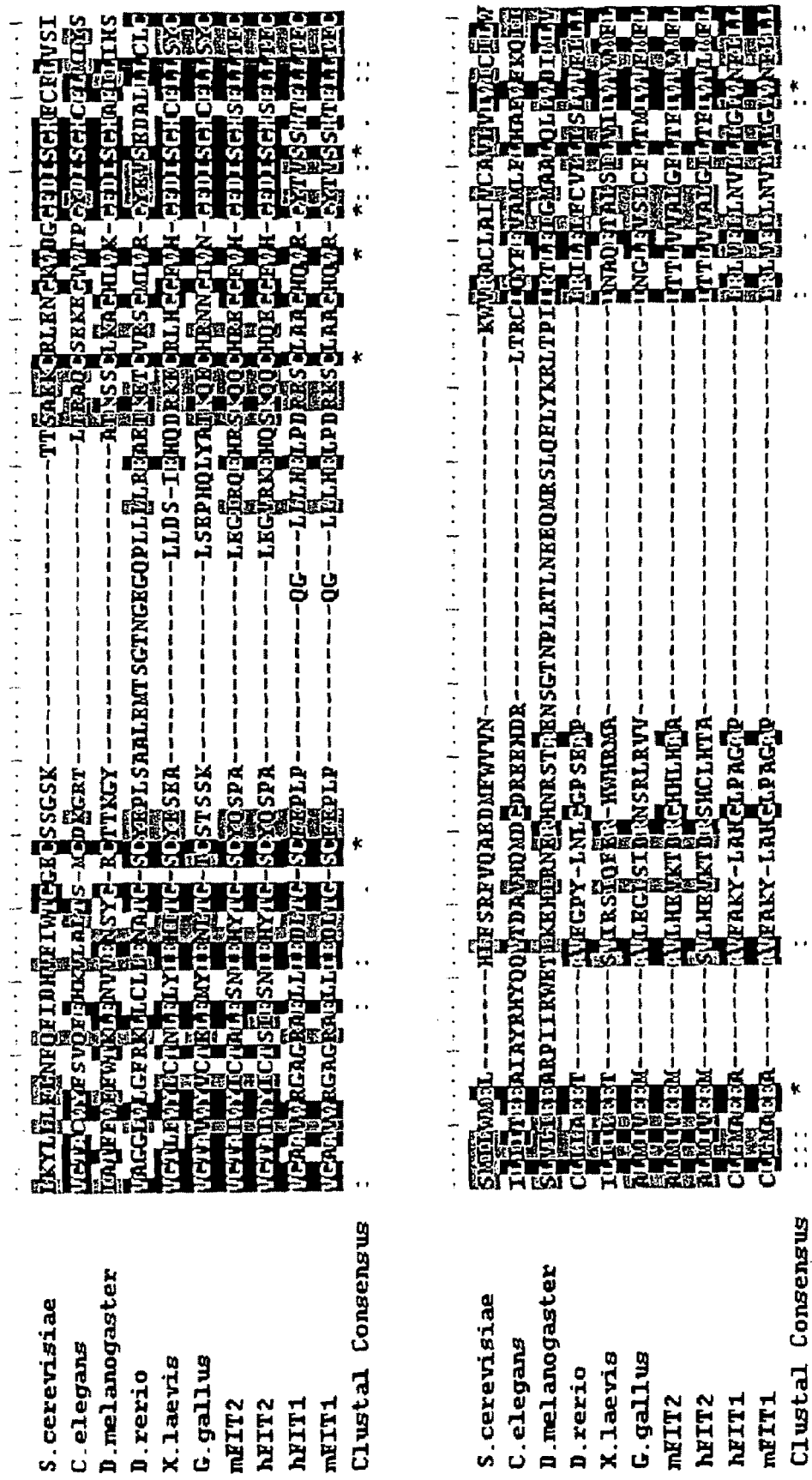
Figure 5B:
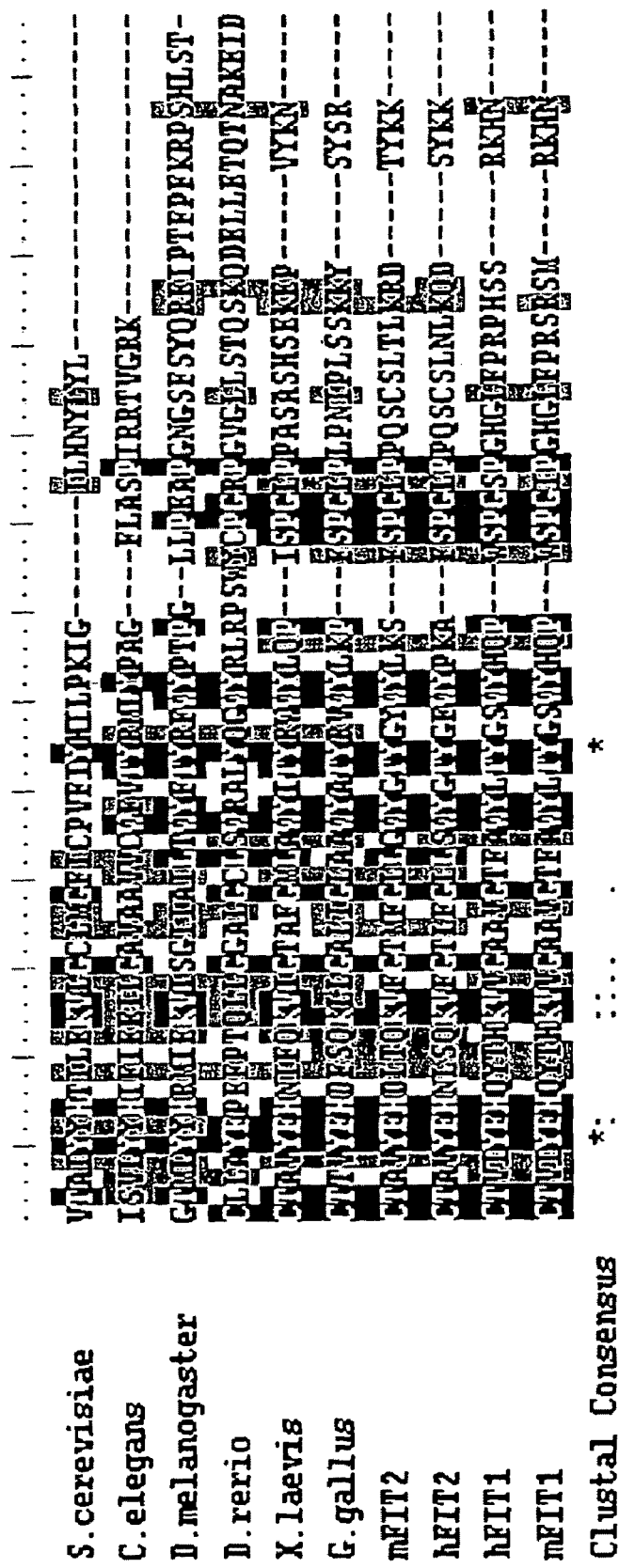

Performing a BLAST search of the full-length mouse FIT1 amino acid sequence against the expressed data base, a second FIT1 homolog was identified in mammals that was designated FIT2. Mammals have two FIT genes, FIT1 and FIT2, while amphibians, birds, fish, insects, worms have a single FIT gene exhibiting higher homology to FIT2 (FIG. 5B) *S. cerevisiae* is an exception because it has two FIT2 orthologs. A second FIT2 ortholog not shown in the cladogram of FIG. 5A is called SCS3. FIT2 was found on the same Affymetrix gene array used to identify FIT1 (Affymetrix number 1454935) and was also increased by fenofibrate on the gene array. The expression of both mouse FIT1 and FIT2 were confirmed to be induced by fenofibrate in a PPARalpha-dependent fashion in liver (FIG. 6). Northern blot analysis of mouse tissues indicated that FIT1 is highly expressed in heart and skeletal muscle, and to lower levels in liver, kidney, brown adipose, testes, and eye (FIG. 1A). Western blot analysis of mouse tissues indicated that FIT1 protein was detected primarily in heart and at low levels in liver and skeletal muscle (FIG. 1B). Mouse FIT2 mRNA was detected as two transcripts in most tissues examined with highest levels in heart, skeletal muscle and brown adipose tissue (FIG. 1A). Note that mFIT2 but not mFIT1 is expressed in white adipose tissue (FIG. 1A). Western blot analysis indicated FIT2 protein highest in heart, and lower levels in lung, liver, and kidney (FIG. 1B) An examination of human tissues showed that FIT1 was primarily expressed in heart and skeletal muscle, while FIT2 was expressed in all tissue represented on the Northern blot (FIG. 1C). Together, these analyses indicated that both mouse and human FIT 1 have a more restricted expression pattern to oxidative tissues, while FIT2 has a broader tissue expression pattern.

Figures 2A, 2B:
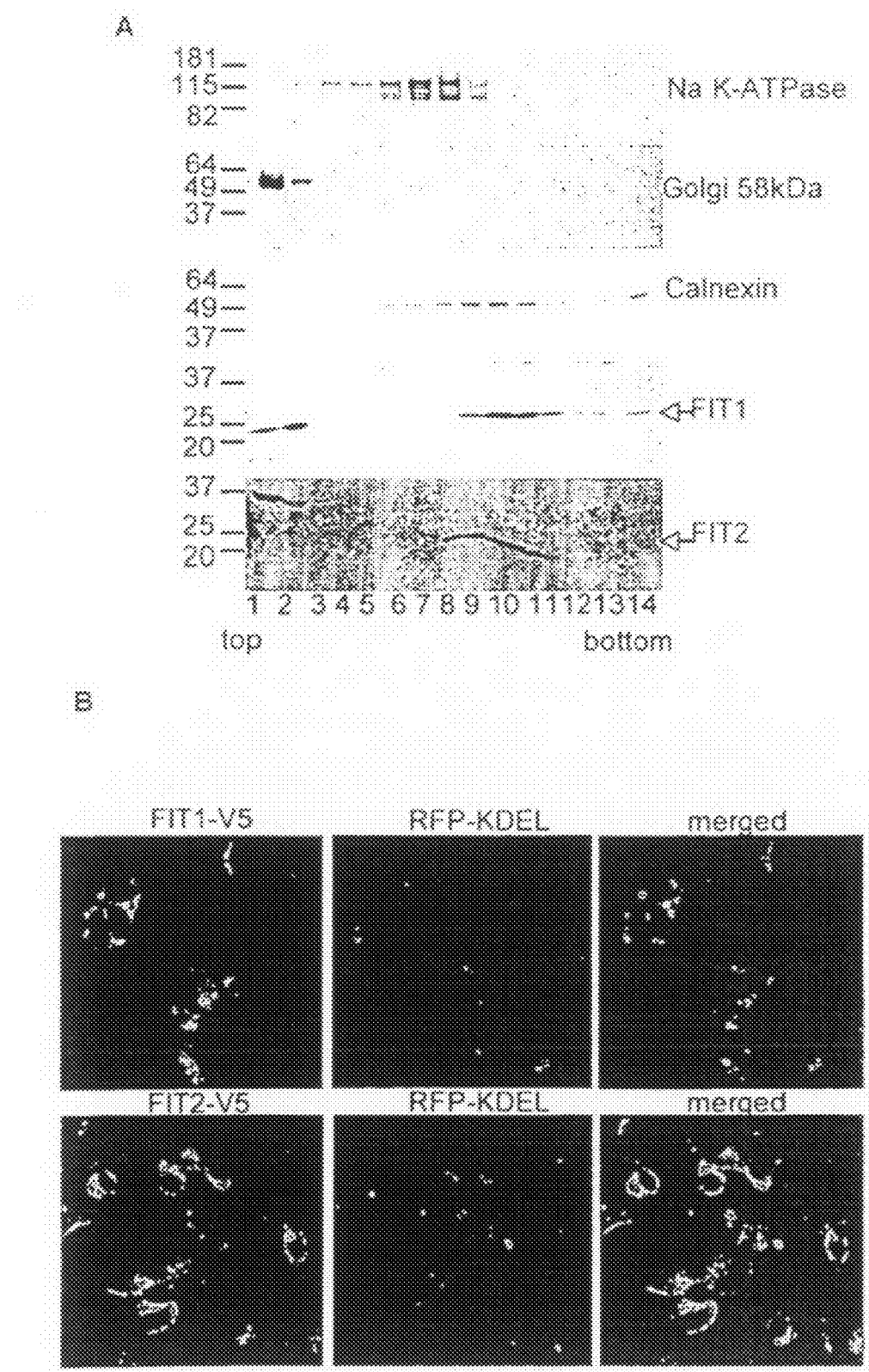
FIG. 2A-2B. Subcellular localization of FIT proteins. (A) Total post-nuclear membranes from mouse hearts were separated by continuous sucrose gradients. Fractions were subjected to Western blot analysis using antibody markers for the plasma membrane (Na K-ATPase), Golgi apparatus (Golgi 58 kDa), endoplasmic reticulum (calnexin), and FIT1 and FIT2. (B) Immunofluorescence localization of mouse FIT1-V5 and FIT2-V5 with the ER marker protein RFP-KDEL in HEK293 cells.
Figure 8:
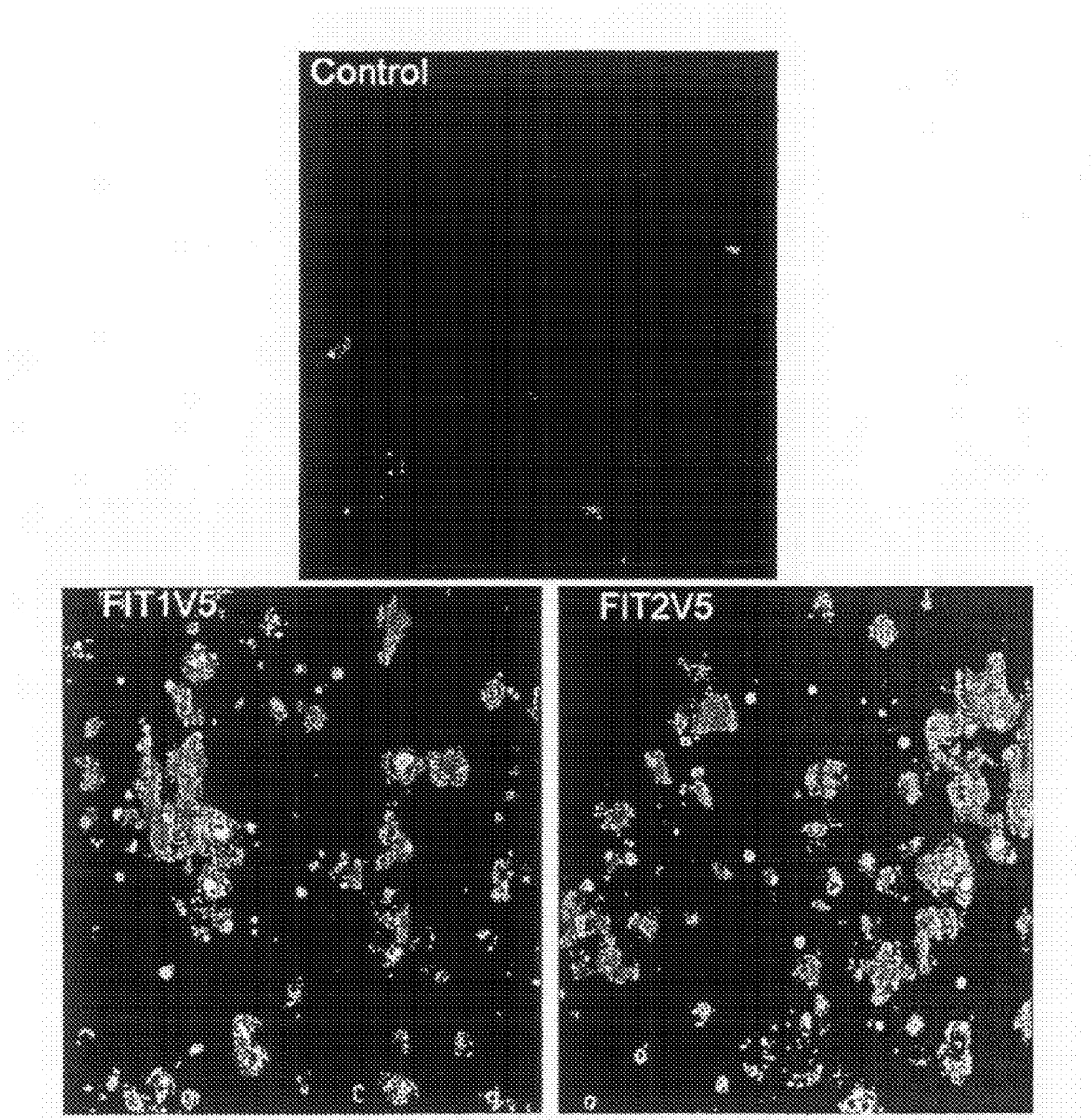
FIG. 8. V5 epitope tagged FIT proteins produce lipid droplets. HEK293 cells were transiently transfected with FIT1-V5 and FIT2-V5 and lipid droplets were visualized by staining cells with BODIPY493/503. Control cells were mock transfected.

FIT1 and FIT2 are localized to the endoplasmic reticulum. In order to define a specific function to FIT proteins, both subcellular fractionation of mouse heart membranes and confocal immunolocalization studies were carried out. Sucrose density fractionation of mouse heart membranes indicated that both FIT1 and FIT2 were co-localized exclusively with endoplasmic reticulum (ER) membrane fractions (FIG. 2A). Expression of a c-terminal V5 tagged FIT1 and FIT2 in HEK 293 cells co-localized with the ER resident protein calnexin (FIG. 2B). Importantly, the V5 tag on FIT1 and FIT2 did not abolish its activity (FIG. 8). Together, the data indicated that FIT1 and FIT2 are localized in the ER.

Figure 3A:
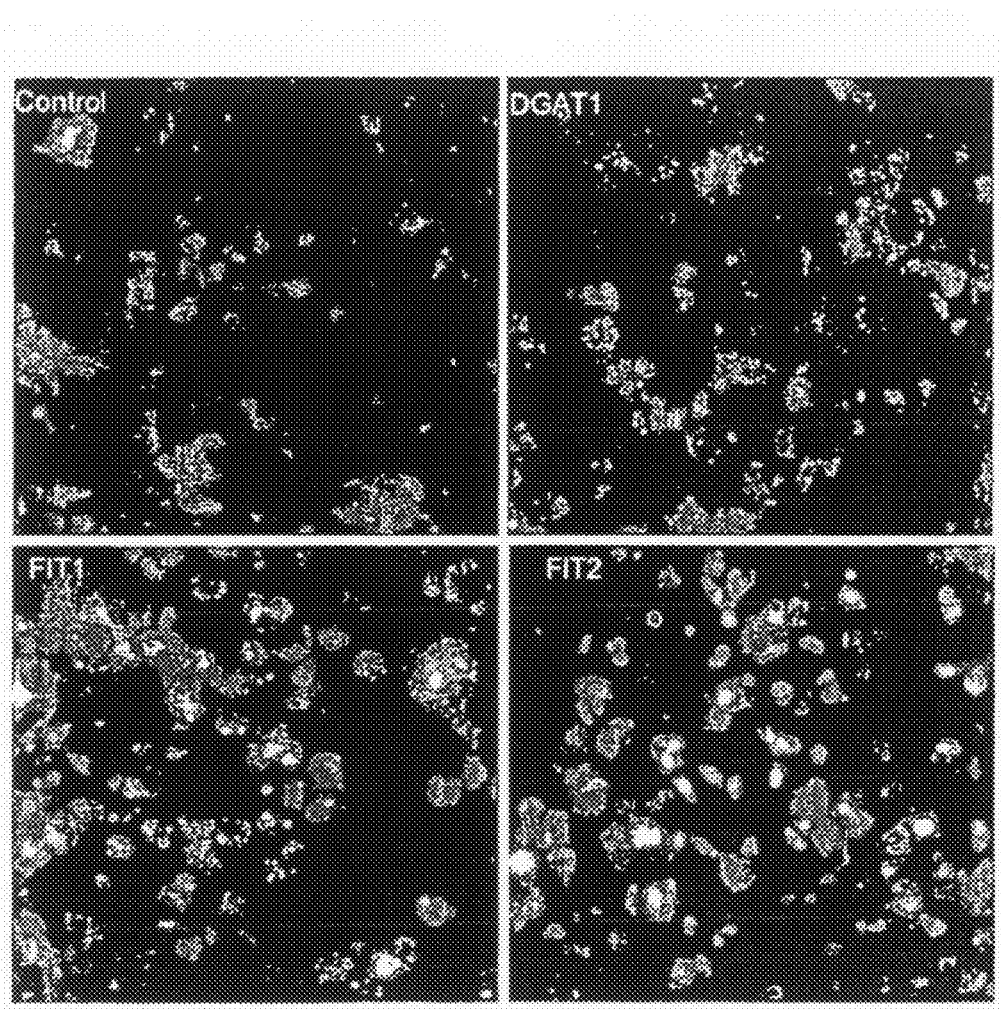
FIG. 3A-3C. Lipid droplet formation induced by FIT1 and FIT2. (A) HEK293 cells were transiently transfected with mouse FIT1, FIT2, or DGAT1 and lipid droplets were visualized using fluorescence microscopy by staining with BODIPY 493/503. (B) Triglyceride mass measurements from transiently transfected cells. M, mock transfected; F1, FIT1 transfected; F2, FIT2 transfected; D1, DGAT1 transfected; D2, DGAT2 transfected. Data are represented as the average±SD. N=4 transfections per construct. (C) Triglyceride (TG) biosynthesis was determined by incubating transiently transfected HEK293 cells with the indicated constructs with $^{14}$C glycerol for the indicated times. $^{14}$C TG were separated using TLC analysis and quantified using phosphorImager analysis. DGATs served as positive controls for TG biosynthesis.
Figure 3B:
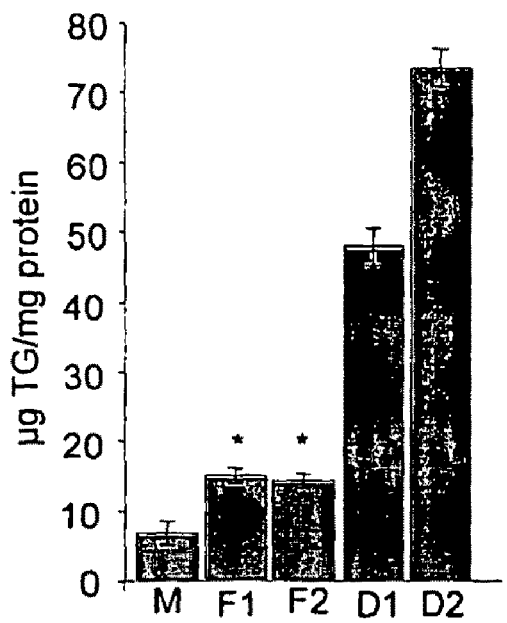
Figure 7:
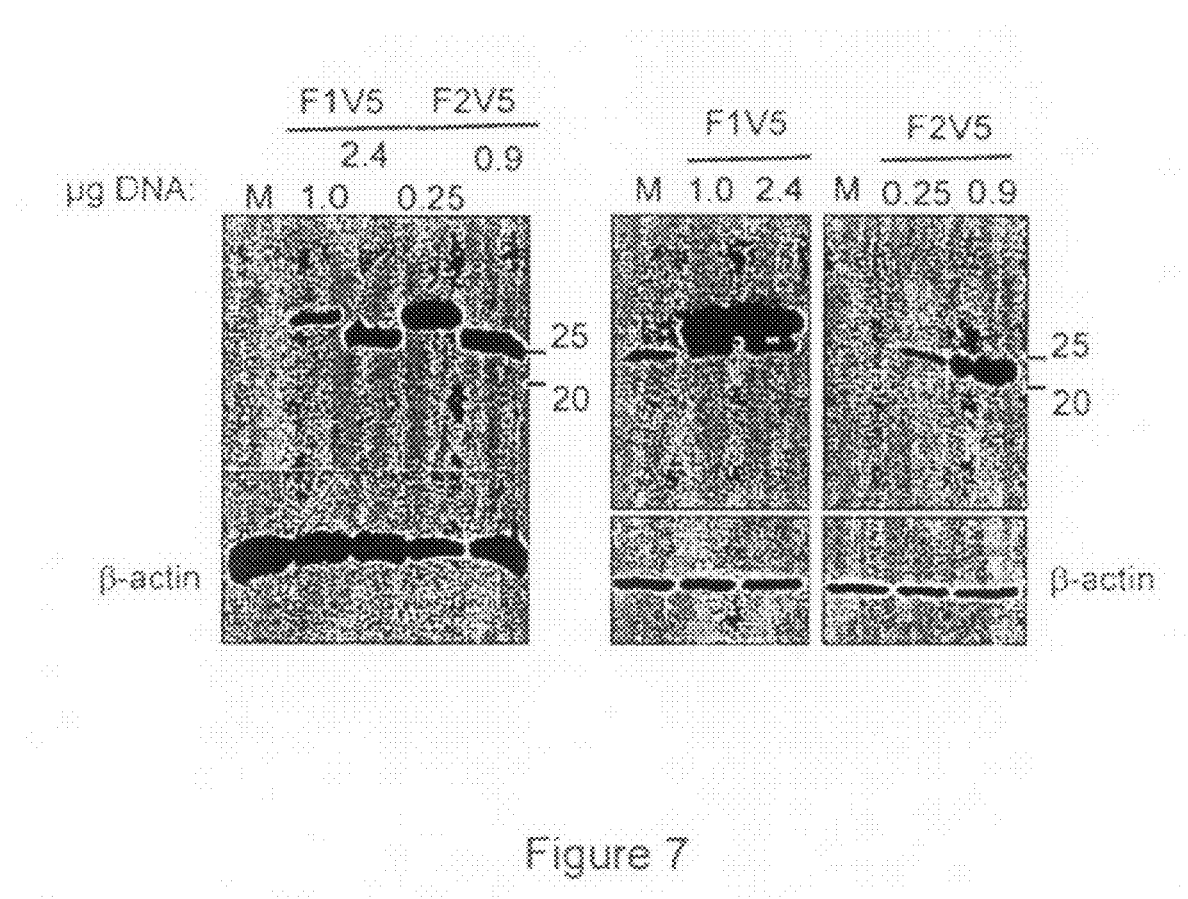
FIG. 7. Titration of FIT expression plasmids in HEK293 cells. HEK293 cells were transiently transfected with the concentrations of plasmid DNA indicated for each construct shown above the Western blots. M, mock transfected; F1V5, mouse FIT1-V5; F2V5, mouse FIT2-V5; F1, mouse FIT1; F2, mouse FIT2. β-actin served as a loading control. The Western blot on the far left was probed with anti-V5 antibody, and blots to the right were probed with either anti-FIT1 or anti-FIT2 antibodies. 2.4 μg of FIT1-V5 and 0.9 μg of FIT2-V5 plasmid consistently gave similar expression levels and were used thought this study.
Figure 9:
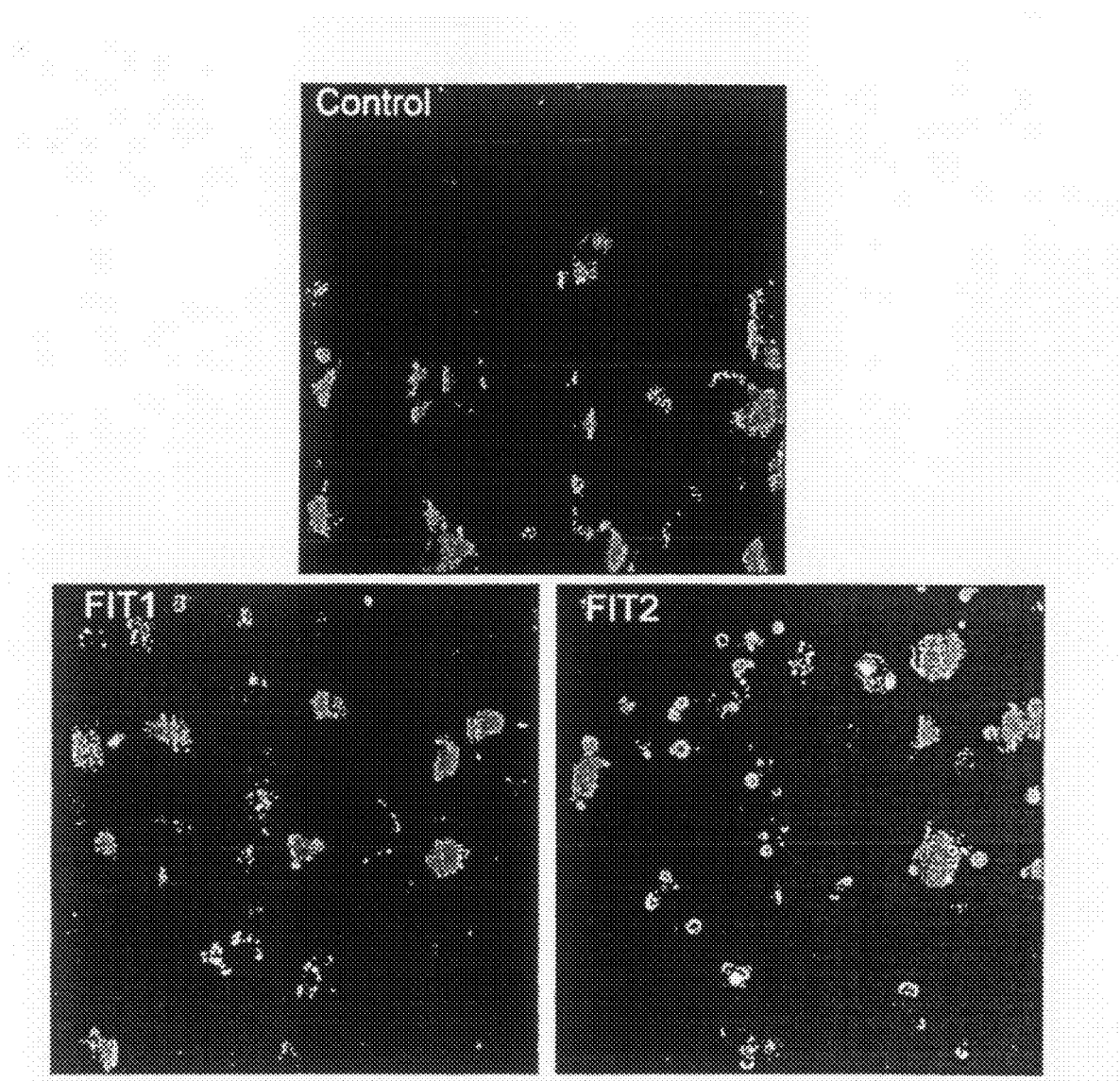
FIG. 9. FIT proteins cause lipid droplet formation in HeLa cells. HeLa cells were transiently transfected with mouse FIT1 and FIT2 and lipid droplets were visualized by staining cells with BODIPY493/503. Control cells were mock transfected.

Overexpression of FIT1 and FIT2 results in the formation of lipid droplets. In order to determine if FIT proteins play a role in lipid metabolism, experiments were designed to overexpress FIT proteins in cells. FIT1 and FIT2 were overexpressed in HEK293 cells and examined using the fluorescent lipid droplet stain BODIPY493/503. FIG. 3A shows that overexpression of FIT1 or FIT2 resulted in the accumulation of lipid droplets. FIT1 overexpression led to the accumulation of multiple droplets per cell with one or two larger droplets per cell, while FIT2 expressed to similar levels as FIT1 (FIG. 7) led to the frequent appearance of a single large droplet. Cells expressing DGAT1, one of two acyltransferases important in the committed step in TG biosynthesis (20) showed multiple lipid droplets smaller than those produced in FIT1 and FIT2 expressing cells (FIG. 3). Overexpression of FIT1 and FIT2 in HeLa cells resulted in similar findings except that FIT2 expression resulted in multiple large droplets per cell, together indicating that FIT1 and FIT2-induced lipid droplet accumulation is not cell-type specific (FIG. 9). Compared to mock transfected cells, cellular TG mass was significantly increased in cells expressing FIT1 and FIT2 (FIG. 3B). These data are consistent with the fluorescent images indicating the presence of lipid droplets in FIT1 and FIT2 expressing cells (FIG. 3A). As a positive control, cells were transfected with DGAT1 or DGAT2, a second acyltransferases important in the committed step in TG biosynthesis (20). Overexpression of DGAT1 or DGAT2 resulted in increased levels of cellular TG that were significantly greater than in FIT1 and FIT2 cells (FIG. 3A).

Figure 17:
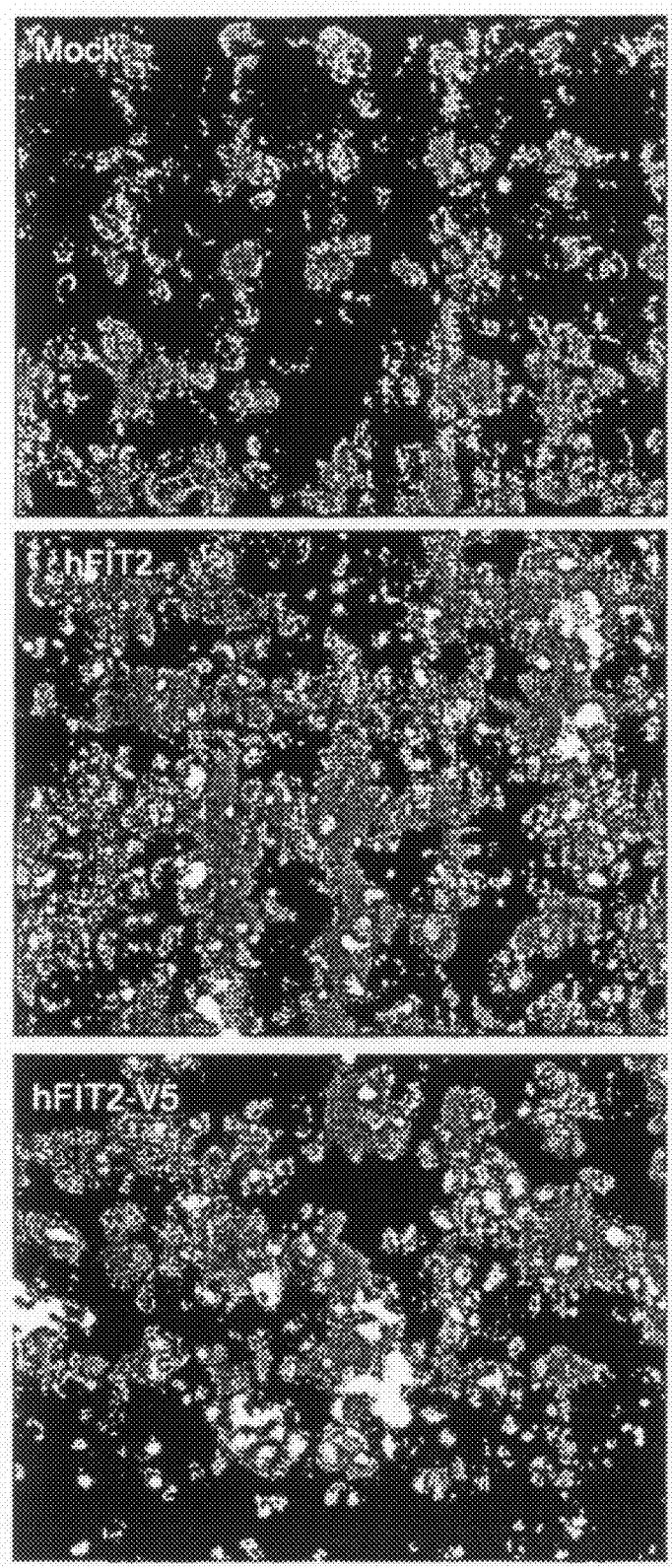
FIG. 17. Human FIT2 expression produces lipid droplets. Overexpression of human FIT2 (hFIT2) and human FIT2 with a C-terminal V5 epitope tag (hFIT2-V5) in HEK293 cells resulted in numerous lipid droplets compared to mock transfected control cells.

Human FIT expression produces lipid droplets. Overexpression of human FIT2 (hFIT2) and human FIT2 with a C-terminal V5 epitope tag (hFIT2-V5) in HEK293 cells resulted in numerous lipid droplets compared to mock transfected control cells (FIG. 17).

Figure 3C:
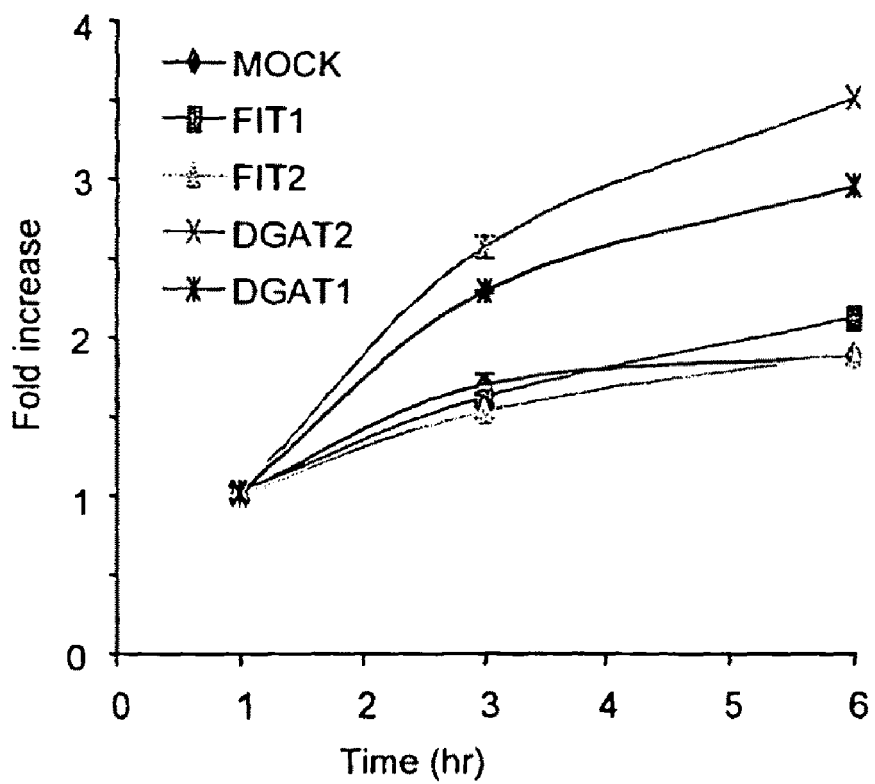
Figures 4A, 4B, 4C:
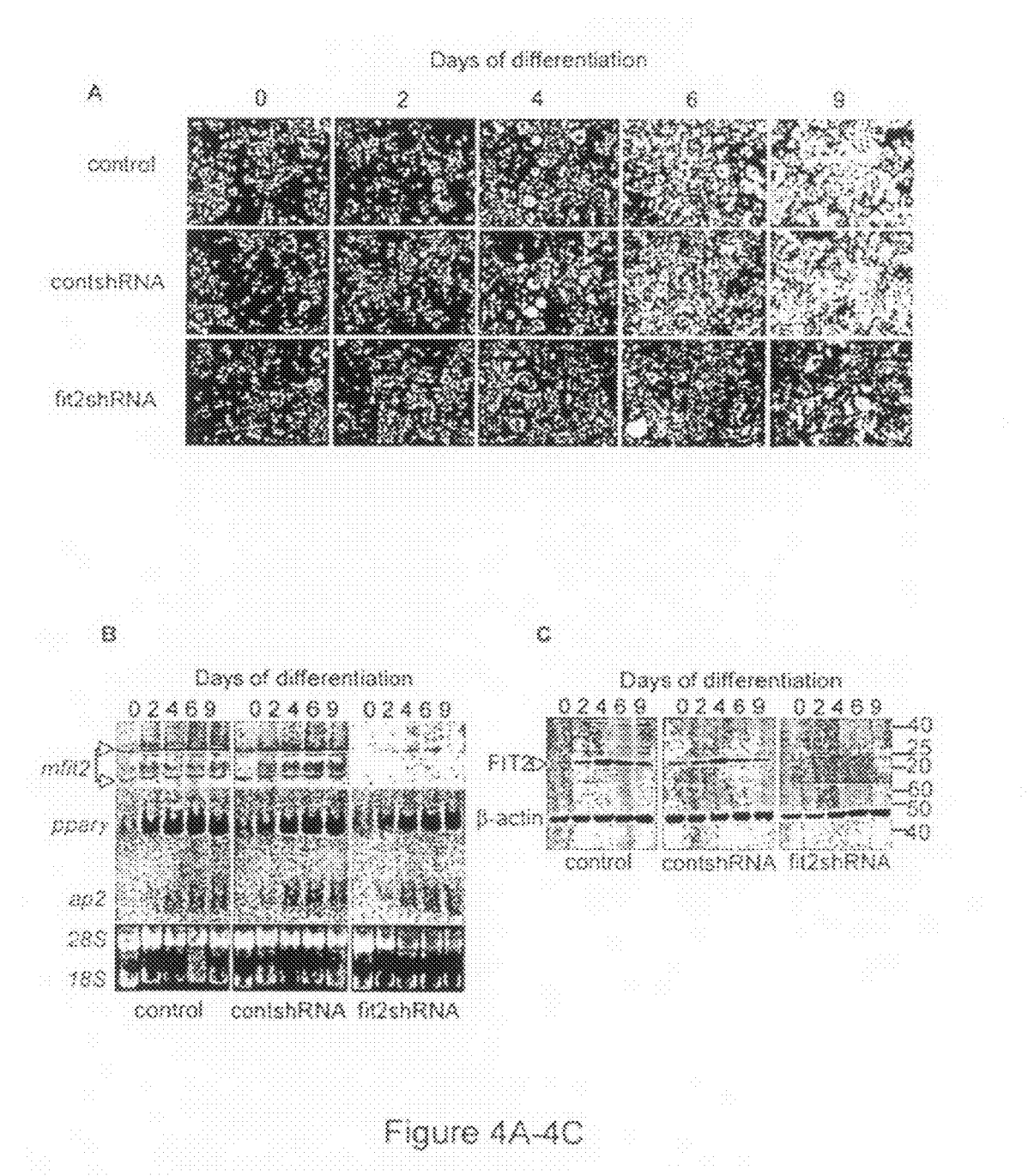
FIG. 4A-4C. shRNAi mediated knockdown of FIT2. NIH-3T3 or RAW246.7 cells were infected with lentivirus expressing shRNA sequence targeting murine FIT2 (FIT2shRNA), or control shRNA (contshRNA), or no lentivirus (control). (A) FIT2shRNA reduced lipid droplet formation during NIH-3T3 cell differentiation (days of differentiation are shown above image) as visualized by BODIPY493/503 staining. (B) Northern blot analysis shows that FIT2shRNA significantly reduced FIT2 mRNA levels compared to control or cont-shRNA infected cells. Expression of differentiation markers Apt and PPARgamma, were not changed in FIT2shRNA treated cells compared to controls. (C) Western blot analysis shows that FIT2 protein is reduced in FIT2shRNA cells compared to controls.
Figure 10:
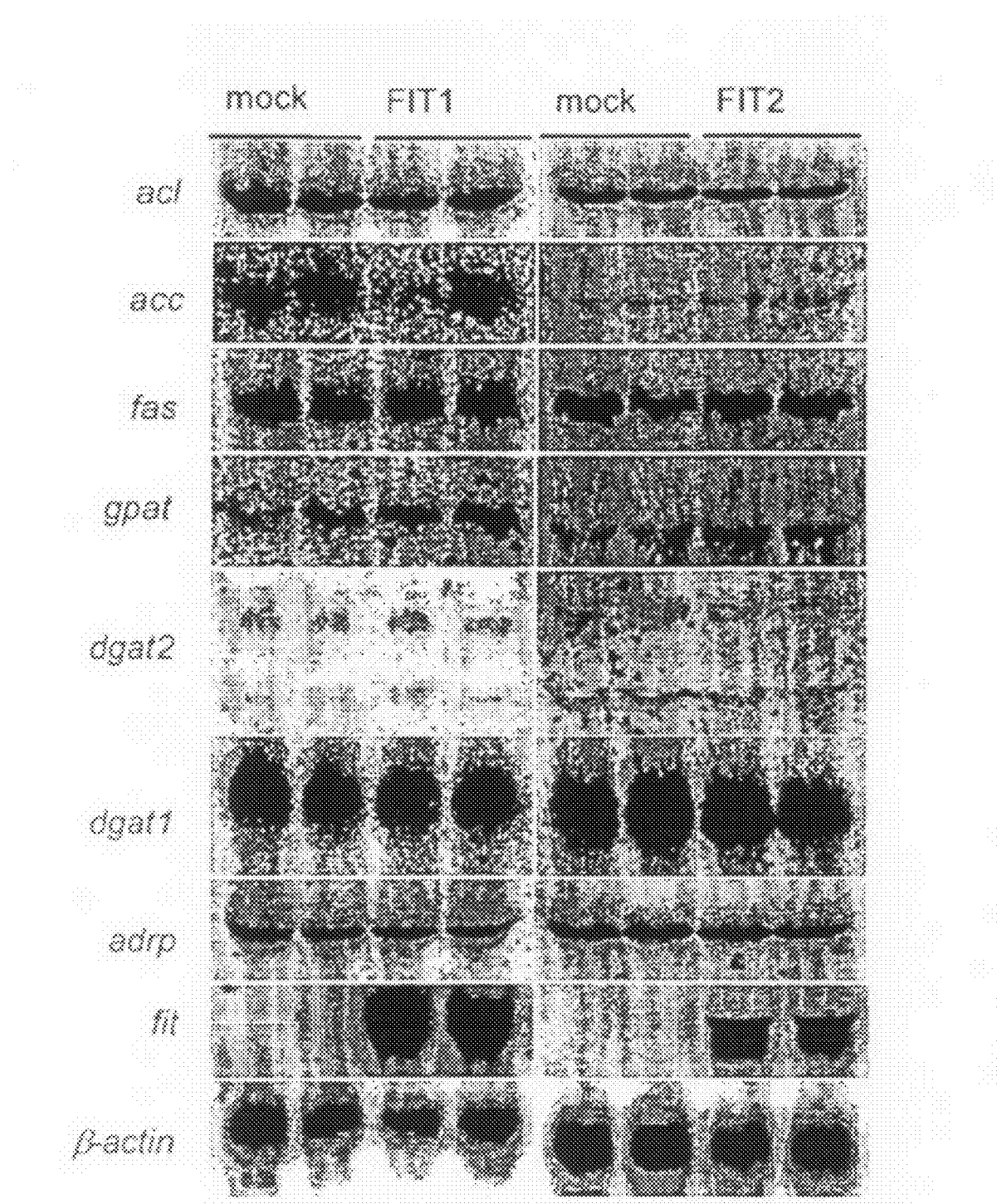
FIG. 10. Expression analysis of genes involved in TG biosynthesis in FIT expressing cells. Northern blot analysis was performed on total RNA (15 μg) from HEK293 cells transfected with mouse FIT1 or FIT2, and hybridized to human DNA probes that listed. Acl, citrate lyase; acc, acetyl-CoA carboxylase; fas, fatty acid synthase; gpat, glyceraldehyde phosphate acyltransferase; dgat2, diacylglycerol acyltransferase 2; dgat1, diacylglycerol acyltransferase 1; adrp, adipocyte differentiation related protein; fit, either human fit1 or fit2. β-actin was used as a loading control.
Figure 11A:
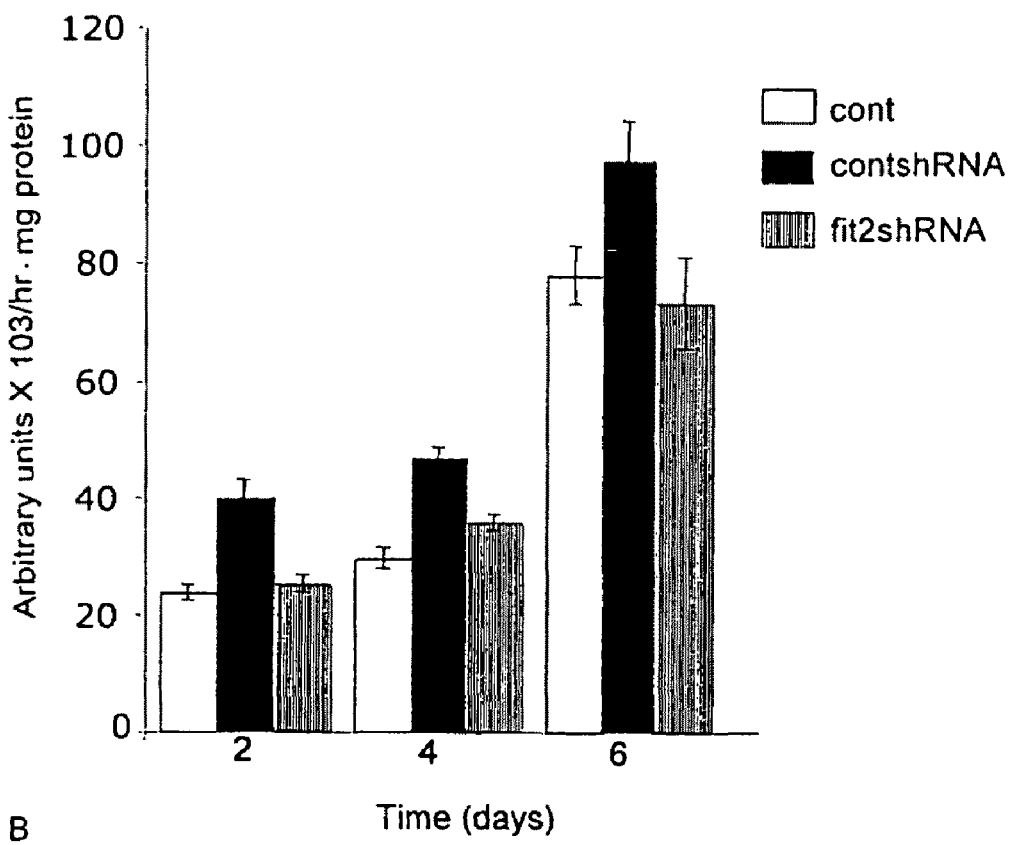
FIG. 11A-11B. Triglyceride biosynthesis and lipolysis assays in FIT2 knockdown cells. (A) Triglyceride synthesis measurements were performed at each time point during differentiation using $^{14}$C glycerol and TLC analysis of triglyceride levels quantified by PhosphorImager analysis. Each time point contained 3 independent samples for each condition, and represented as mean±std, p<0.001. 3 independent samples were used for each condition, and represented as mean±std, p<0.001. (B) Lipolysis assays performed on cell lysates from NIH 3T3-L1 cells at day 4 and day 6 of differentiation. No differences were observed between control and shRNAcont and FIT2shRNA adipocytes.
Figure 11B:
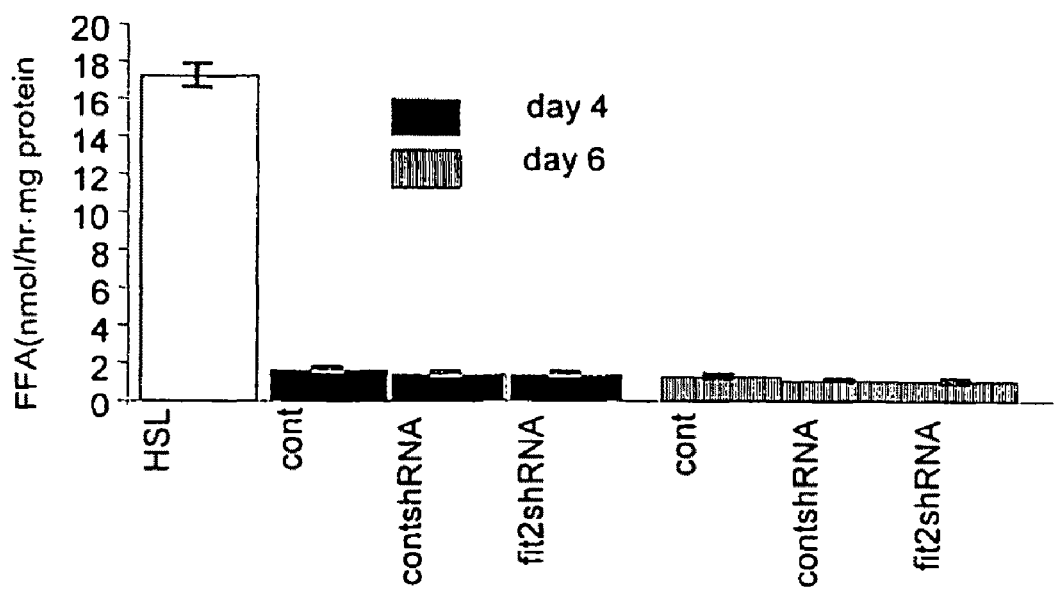

FIT proteins do not enhance triglyceride biosynthesis. It was also determined whether FIT1 and FIT2 enhance TG biosynthesis causing lipid droplets to form by quantifying the rate of TG biosynthesis using radiolabeled glycerol as a precursor for TG. Cells expressing FIT1 or FIT2 showed similar rates of TG biosynthesis compared to mock transfected cells, indicating that the accumulation of lipid droplets in FIT1 and FIT2 expressing cells is not the result of enhanced TO biosynthesis. The mRNAs of genes important in fatty acid and TG biosynthesis were not changed in cells expressing FIT1 or FIT2 (FIG. 10). As expected from previous studies, DGAT1 and DGAT2 overexpression led to a significant increase in TG biosynthetic rate (20) (21). To test if increased cellular TG is the result of partitioning of TG into lipid droplets, cells were incubated with $^{14}C$ glycerol tracer for 24 hrs and radiolabel in lipid droplets were quantified. FIG. 3C shows that cells expressing FIT1 and FIT2 had a significant increase in the percent of labeled glycerol in lipid droplets compared to mock transfected cells. As a positive control, DGAT1 and DGAT2 expressing cells exhibited a significant increase in radiolabeled glycerol in lipid droplets compared to mock, FIT1 and FIT2 expressing cells (FIG. 3C). Taken together, these results indicate that FIT1 and FIT2 do not directly mediate triglyceride biosynthesis, but lipid droplet formation leading to the accumulation of cellular neutral lipids.

shRNA suppression of FIT2 abolishes lipid droplet formation during adipogenesis. To provide a direct test if FIT proteins are essential for the formation of lipid droplets, knockdown of FIT expression was sought in established cellular models of lipid droplet formation. If FIT genes are essential for lipid droplet formation, then the NIH-3T3 L1 cell line, a classic adipocyte differentiation cell model that produces large amounts of lipid droplets during differentiation of pre-adipocytes into adipocytes, should express FIT genes during adipogenesis at the onset of lipid droplet accumulation. FIGS. 4B and 4C show that high levels of FIT2 at both mRNA and protein levels, but not FIT1 (data not shown), were detected during adipogenesis at the onset of formation of visible lipid droplets (FIG. 4A). This is in line with the observation that Fin and not FIT1 are expressed in white adipose tissue in vivo (FIGS. 1A,B). If FIT2 is indeed essential for droplet formation, then suppression of FIT2 expression should abolish lipid droplet formation. Pre-adipocytes cells infected with lentivirus expressing shRNA against FIT2, a control shRNA, or no virus were induced to differentiate. FIT2 mRNA and protein were significantly suppressed in adipoctyes infected with lentivirus expressing FIT2 shRNA. Examination of these cells for lipid droplets showed that cells having suppressed FIT2 expression had an almost complete absence of lipid droplets in pre-adipocytes (day 0) and in mature adipocytes (between day 4 and 9) (FIG. 4A). Only a low level of cells expressing the FIT2shRNA exhibited multiple lipid droplets per cell between day 6 and 9 (FIG. 4A). Further examination of FIT2 suppressed cells showed that the expression of PPAR-gamma and AP2, genetic markers of adipocyte differentiation, were not changed (FIG. 4B). Triglyceride biosynthesis or triglyceride lipase activities were similar in adipocytes having a knockdown of FIT2 compared to controls (FIG. 11-11B). Taken together, the data indicate that knockdown of FIT2 specifically inhibited lipid droplet formation.

Figure 12:
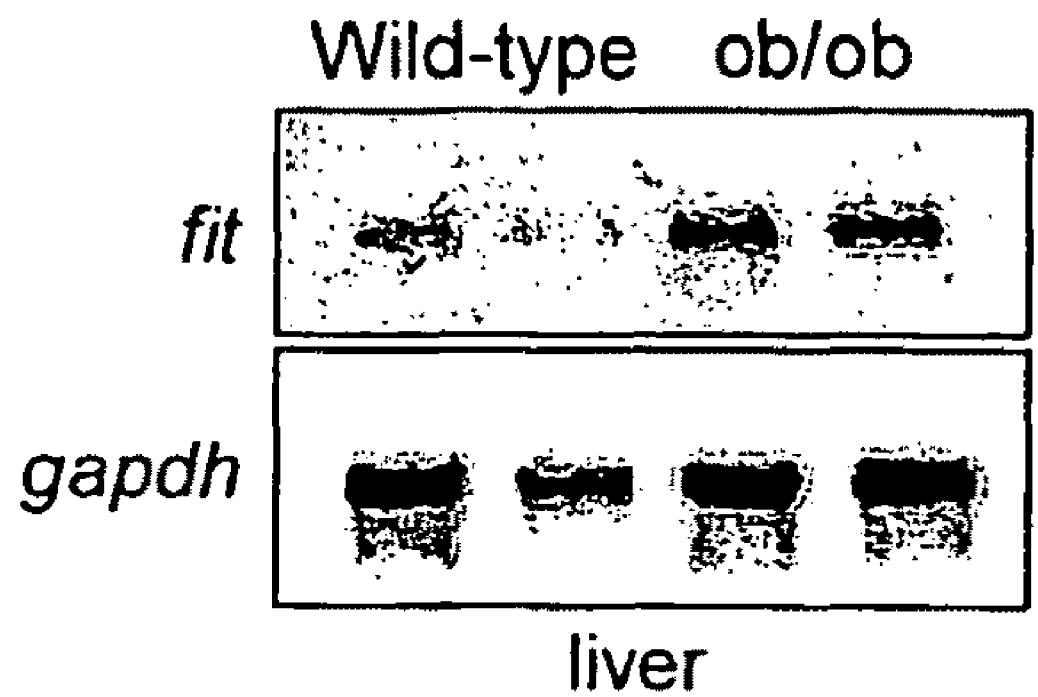
FIG. 12. FIT1 is overexpressed in steatotic livers of ob/ob mice. RNA was isolated from wild-type and ob/ob mouse livers and adipose tissue and analyzed by Northern blot (20 µg of RNA per lane). Figure shows results from two independent mice per genotype. FIT1 is upregulated in both livers and adipose tissue of ob/ob mice compared to wild-type lean controls.

FIT is overexpressed in steatotic livers of ob/ob mice. Ob/ob mice are insulin resistant, have fatty livers and are obese. RNA was isolated from wild-type and ob/ob mouse livers and adipose tissue and analyzed by Northern blot (20 μg of RNA per lane). FIG. 12 shows results from two independent mice per genotype. FIG. 12 indicates that FIT1 is upregulated in both livers and adipose tissue of ob/ob mice compared to wild-type lean controls. This data suggests that FIT1 overexpression in livers of obese animals might be responsible for the formation of fatty liver.

Figure 13A:
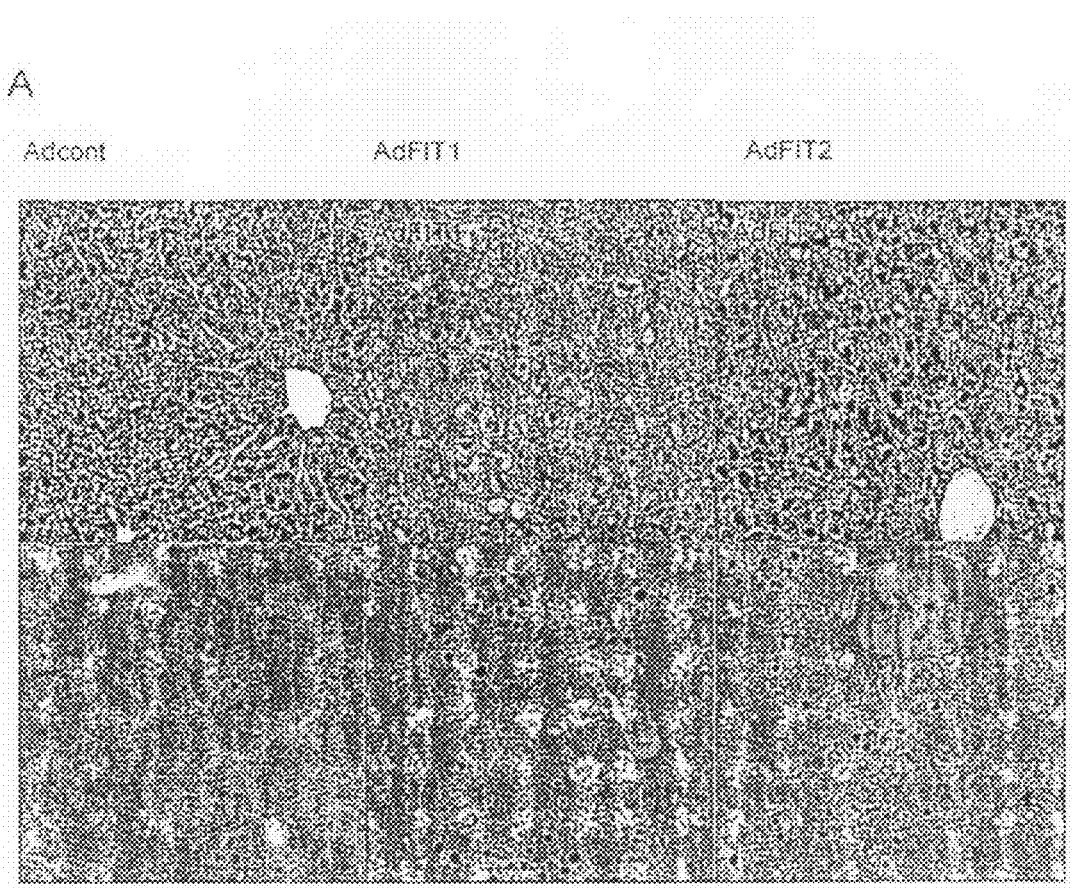
FIG. 13A-13B. FIT1 and FIT2 overexpression in mouse liver increases lipid deposition. (A) Control adenovirus injected mice had normal lipid deposition and liver morphology, while mice injected with the AdFIT1 and AdFIT2 adenovirus showed an accumulation of lipid in livers. Left column, Ad control; middle column, Ad FIT1; right column Ad FIT2. (B) FIT1 and FIT2 protein levels are increased in mouse livers injected with FIT1 and FIT2 adenoviruses compared to control injected mice.
Figure 13B:
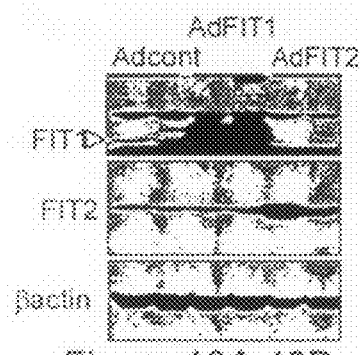

FIT1 and FIT2 overexpression in mouse liver increases lipid deposition. Overexpression of mouse FIT1 and FIT2 in mouse liver causes triglyceride accumulation. Mouse FIT1 and FIT2 were first subcloned into adenovirus shuttle vector (pVW-CVM K-NpA) and adenovirus was synthesized (service provided by Viraquest, Iowa). Two groups of 6 wild-type male C57BL6J mice were injected intravenously with $1 \times 10^8$ pfu with empty adenovirus control (adEmpty) or adenovirus expression FIT1 (adFIT1). All mice were fed a standard chow diet for the first 3 days, then switched to a high fat diet (cat#TD.93075 Harlan Teklad) for 4 days. Perfused livers from mice were either frozen in OTC for producing frozen sections for oil-red-o staining, or fixed in 10% formalin and embedded in paraffin for H&E staining. FIG. 13A shows that control adenovirus injected mice had normal lipid deposition and liver morphology, while mice injected with the AdFIT1 and AdFIT2 adenovirus showed an accumulation of lipid in livers. FIG. 13B shows increased protein levels of FIT1 and FIT2 in mouse livers injected with FIT1 and FIT2 adenoviruses compared to control injected mice.

Figure 14:
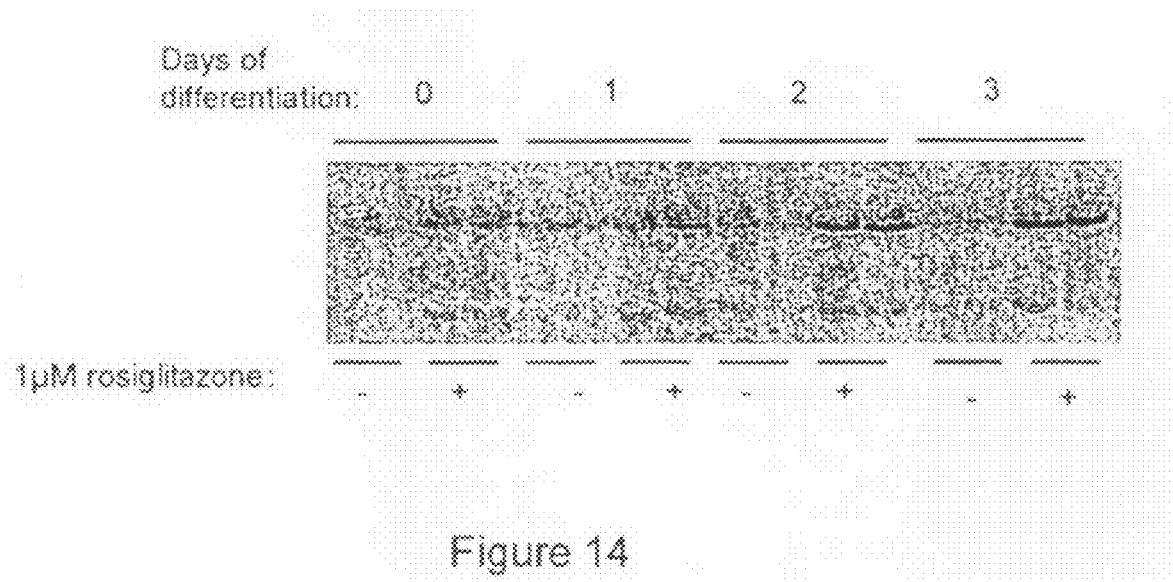
FIG. 14. Rosiglitazone induces mFIT2 expression. NIH 3T3 preadipocytes were differentiated for the days indicated and treated or not treated with 1 µM rosiglitazone for 24 hrs. FIT2 mRNA was increased at all time points of differentiation by treatment with rosiglitazone (−, no rosiglitazone; +1 µM rosiglitazone). All lanes are from duplicate wells of cells.

Rosiglitazone induces mFIT2 expression. NIH 3T3 preadipocytes were differentiated as in FIG. 14 for the days indicated (0, 1, 2, or 3 days) and treated or not treated with 1 μM rosiglitazone for 24 hrs. mRNA was isolated and analyzed by Northern blot analysis. FIT2 mRNA was increased at all time points of differentiation by treatment with rosiglitazone. Importantly, rosiglitazone increased FIT2 at time point zero indicating that the effect is likely independent of differentiation of the preadipocytes into adipocytes.

Figure 15:
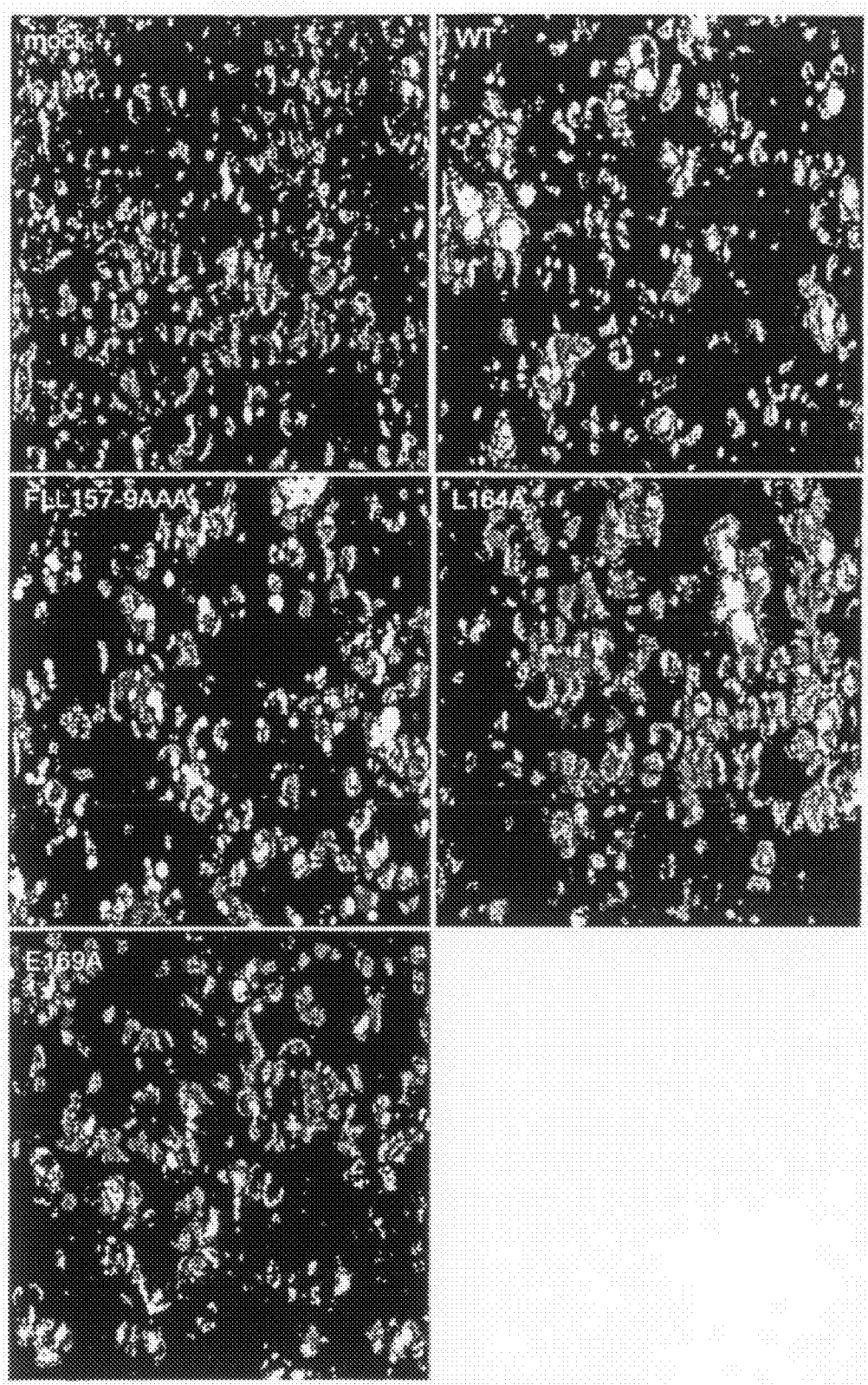
FIG. 15. Lipid droplet formation in HEK 293 cells expressing wild-type or mutant FIT2. Mock, mock transfected control; WT, wild-type FIT2; FLL 157-9 AAA mutation, L164A mutation, E169A mutation.
Figure 16:
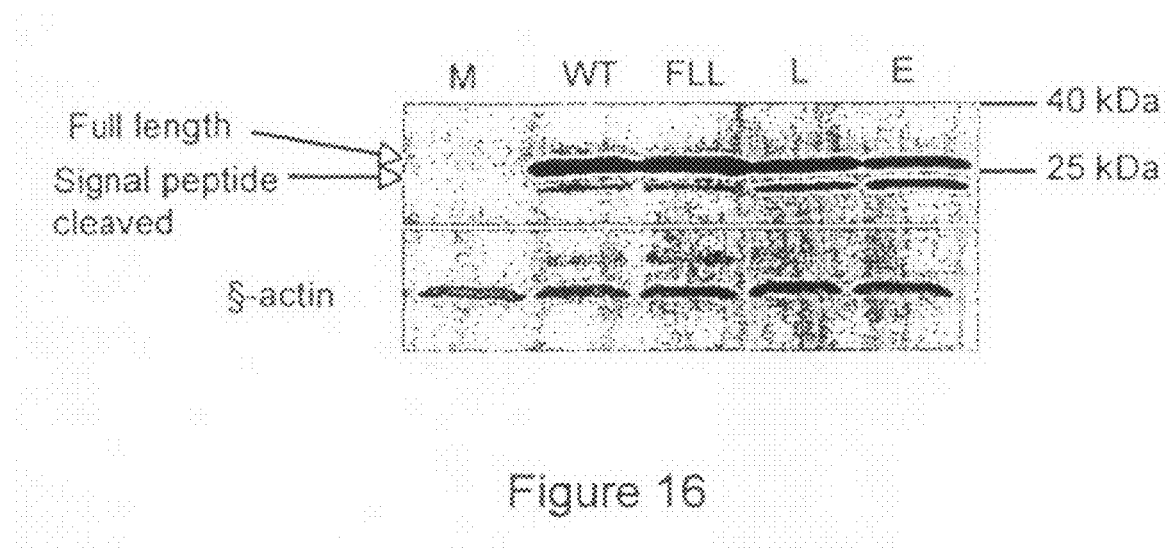
FIG. 16. Western blot of FIT2 protein levels in HEK 293 cells expressing wild-type or mutant FIT2. M, mock transfected control; WT, wild-type FIT2; FLL, 157-9FLLAAA mutation, L, L164A mutation, E, E169A mutation. All mutants and wild-type are c-terminally tagged with the V5 epitope.

Lipid droplet formation in cells transfected with wild-type and mutant FIT2. The effects of mutations in amino acids comprising a highly conserved domain in mouse FIT2 were observed on lipid droplet formation. Amino acids 157 phenylalanine (F), 158 leucine (L), 159 leucine (L), 164 leucine (L), and 169 glutamic acid (E) are among the most highly conserved amino acids found in all species having a FIT2 homolog. Mutations in the tandem amino acids FLL (amino acids 157 through 159) substituted with alanine (A) residues resulted in a FIT2 protein that produced more and brighter droplets than the wild-type FIT2 (FIT2-V5) transiently expressed in HEK 293 cells (FIG. 15). FIT2 mutants having either the 164L or 169E residue substituted by alanine resulted in a greatly diminished ability to produce droplets. Moreover, the L164A and E169A mutants both produced multiple small droplets, a phenotype distinct from the large droplets produced by wild-type and FLL157-9AAA mutant FIT2 proteins (FIG. 15). Importantly, the phenotypes observed were not due to changes in FIT2 protein levels, although L164A and E169A mutants had a minor decrease in levels as well as minor cleavage of the signal peptide as shown in Western blot FIG. 16. Together, the results indicate that the FLL domain plays a role to limit FIT2 activity, while the 164L and 169E residues are essential for FIT2 to form droplets. Thus, these amino acid domains on FIT2 can serve as targets for small molecule activators and inhibitors that may interact with these amino acid domains to either augment FIT2 activity or inhibit FIT2 activity.

Mouse transgenic models of FIT1 and FIT2 overexpression: liver-specific expression. Transgenic mice were generated that overexpress mouse FIT1 and FIT2 specifically in liver. Based on the finding that overexpression of FIT1 and FIT2 in mouse liver using adenovirus results in fatty liver on a high fat diet, these transgenic mouse models are expected to have fatty liver on high fat diets. These animal models should be suitable to study the progression of fatty liver diseases (alcoholic and non-alcoholic) and steatohepatitis as well as the role of fatty liver in type 2 diabetes and insulin resistance. In addition, these models will be useful in testing therapies for these diseases, such as screening therapeutic compounds (small molecules, proteins, RNAi, aptamers).

Mouse transgenic models of FIT1 and FIT2 overexpression: skeletal muscle-specific expression. Transgenic mice were generated that overexpress mouse FIT1 specifically in skeletal muscle. This animal model is expected to be useful in studying type 2 diabetes and obesity, and muscle metabolism and function. This model will be useful in testing therapies or screening therapeutic compounds (small molecules, proteins, RNAi, aptamers) for diseases (rhabomyolysis, myostitis, type 2 diabetes, lipotoxycity) as well as improving normal physiology (i.e. muscle function, lipid and glucose metabolism).

Mouse transgenic models of FIT) and FIT2 overexpression: heart-specific expression. Transgenic mice were generated that overexpress mouse FIT1 specifically in cardiac myocytes. These mice are expected to be suitable models to study cardiomyopathy, and defects in cardiac function related to altered cardiac metabolism. This model will be useful in testing therapies or screening therapeutic compounds (small molecules, proteins, RNAi, aptamers) for diseases such as cardiomyopathy, cardiac dysfunction, cardiac ischemia, and altered cardiac metabolism, as well as improving normal physiology (i.e. cardiac function, lipid and glucose metabolism).

Mouse transgenic models of FIT1 and FIT2 overexpression: adipose-specific expression. Transgenic mice were generated that overexpress mouse FIT2 specifically in adipose tissue (white and brown adipose). These transgenic mice are expected to be useful as a model of obesity and type 2 diabetes and metabolic syndrome. These transgenic mice can be used to test therapeutic compounds or other therapies to treat obesity, type 2 diabetes and metabolic syndrome.

Mouse deficiency models for FIT1 and FIT2: FIT1 gene targeted mice. FIT1 Knockout mice have been generated and found to be viable and fertile. These mice might be a suitable model for defects in cardiac, skeletal muscle, liver and kidney dysfunction and therefore are expected to also be useful to test therapeutic agents that regulate muscle, heart, liver, and kidney function.

Mouse deficiency models for FIT1 and FIT2: FIT2 gene targeted mice. The targeted A3 ES cell line was used to generate chimeric mice. It was determined that deletion of FIT2 results in embryonic lethality. Mouse embryonic fibroblasts from FIT2 knockouts may be useful as a model to screen for small molecule inhibitors of FIT genes. In addition, mice heterozygous for FIT2, which are viable, might be a suitable model to study the effects of inhibitors or activators of FIT2, as well as assessing the effects of having reduced levels of FIT2 on cardiac, muscle, liver, kidney and brain function. These mice having 50% less FIT2 might mimic humans that are heterozygous for mutations in FIT2, since homozygous mutations would be expected to be extremely rare.

FIT2 Conditional targeted mice. Based on the finding that gene targeted deletion of FIT2 results in embryonic lethality, BAC recombineering was used to produce a "floxed" allele of FIT2 to conditionally knock it out in adult mice. Conditional knockout mice for FIT2 are expected to be useful for studying organ specific effects of FIT2 inhibition on normal and pathophysiology. Conditional knockout mice will be an important model to test the safety and efficacy of inhibiting FIT2 in specific cell types and organs. For example, knockdown of FIT2 specifically in white adipose tissue should result in resistance to obesity and enhanced insulin sensitivity.

The present study describes for the first time the identification of a highly conserved family of proteins that are essential in mammalian cells for the formation of lipid droplets, independent of TG biosynthesis. FIT genes encode for multi-transmembrane, endoplasmic reticulum localized proteins. Overexpression of FITs in cell culture and mouse liver resulted in the formation of lipid droplets without enhancing triglyceride biosynthesis. Moreover, shRNA silencing of FIT genes in white adipocytes prevented lipid droplet formation during adipogenesis. Reagents that regulate FIT expression or activity are expected to impact the many diseases associated with excessive lipid droplet formation, such as obesity, diabetes, and atherosclerosis. Regulation of energy metabolism, feeding behavior and hepatic glucose output is highly regulated by lipids and energy status (ATP, AMP) in the brain. Inhibiting or activating FIT1 or FIT2 genes or protein activity in the brain (using small molecules, or nucleic acids, ASO, RNAi, aptamers) may beneficially alter energy metabolism, feeding behavior and hepatic glucose output in humans.

REFERENCES

1. S. Martin, R. G. Parton, *Nat Rev Mol Cell Biol* 7, 373 (May, 2006).
2. R. Zechner, J. G. Strauss, G. Haemmerle, A. Lass, R. Zimmermann, *Curr Opin Lipidol* 16, 333 (June, 2005).
3. J. E. Schaffer, *Curr Opin Lipidol* 14, 281 (June, 2003).
4. B. B. Kahn, J. S. Flier, *J Clin Invest* 106, 473 (August, 2000).
5. B. M. Spiegelman, J. S. Flier, *Cell* 104, 531 (Feb. 23, 2001).
6. G. I. Shulman, *J Clin Invest* 106, 171 (July, 2000).
7. H. Mullner, G. Daum, *Acta Biochim Pol* 51, 323 (2004).
8. D. L. Brasaemle, G. Dolios, L. Shapiro, R. Wang, *J Biol Chem* 279, 46835 (Nov. 5, 2004).
9. P. Liu et al., *J Biol Chem* 279, 3787 (Jan. 30, 2004).
10. M. Beller et al., *Mol Cell Proteomics* (Mar. 16, 2006).
11. C. Londos et al., *Ann N Y Acad Sci* 892, 155 (Nov. 18, 1999).
12. C. Londos, D. L. Brasaemle, C. J. Schultz, J. P. Segrest, A. R. Kimmel, *Semin Cell Dev Biol* 10, 51 (February, 1999).
13. A. B. Novikoff, P. M. Novikoff, O. M. Rosen, C. S. Rubin, *J Cell Biol* 87, 180 (October, 1980).
14. E. J. Blanchette-Mackie et al., *J Lipid Res* 36, 1211 (June, 1995).
15. K. Tauchi-Sato, S. Ozeki, T. Houjou, R. Taguchi, T. Fujimoto, *J Biol Chem* 277, 44507 (Nov. 15, 2002).
16. A. Pol et al., *Mol Biol Cell* 15, 99 (January, 2004).
17. D. J. Mangelsdorf et al., *Cell* 83, 835 (Dec. 15, 1995).
18. B. Staels et al., *Circulation* 98, 2088 (Nov. 10, 1998).
19. I. Issemann, S. Green, *Nature* 347, 645 (Oct. 18, 1990).
20. S. Cases et al., *Proc Natl Acad Sci USA* 95, 13018 (Oct. 27, 1998).
21. S. Cases et al., *J Biol Chem* 276, 38870 (Oct. 19, 2001).
22. R. Ylitalo, O. Jaakkola, P. Lehtolainen, S. Yla-Herttuala, *Life Sci* 64, 1955 (1999).
23. D. J. Rader, E. Pure, *Cell Metab* 1, 223 (April, 2005).
24. A. K. Student, R. Y. Hsu, M. D. Lane, *J Biol Chem* 255, 4745 (May 25, 1980).
25. S. J. Smith et al., *Nat Genet.* 25, 87 (May, 2000).
26. Warming S, Costantino N, Court D L, Jenkins N A, Copeland N G. Simple and highly efficient BAC recombineering using galK selection. Nucleic Acids Res. 2005 Feb. 24; 33(4):e36.

---

What is claimed is:

1. A method for screening for a candidate agent that can reduce fat storage in tissue by determining whether or not the agent is effective to decrease the level of FIT1 and/or FIT2 in tissue or cells, wherein the method comprises contacting the agent with cells or tissue that express FIT1 and/or FIT2, and wherein reduction in expression or activity of FIT1 and/or FIT2 is indicative that the agent is a candidate agent for decreasing fat storage in tissue.

2. A method for screening for a candidate agent that can increase fat storage in tissue by determining whether or not the agent is effective to increase the level of FIT1 and/or FIT2 in tissue or cells, wherein the method comprises contacting the agent with cells or tissue that express FIT1 and/or FIT2, and wherein an increase in expression or activity of FIT1 and/or FIT2 is indicative that the agent is a candidate agent for increasing fat storage in tissue.

3. The method of claim 2, wherein the cells are mouse embryo fibroblasts isolated from FIT2 knockout embryos, and wherein the fibroblasts are stably or transiently transfected with FIT1 and/or FIT2 under control of a regulated or constitutively active promoter.

4. The method of claim 2, wherein the agent affects expression of FIT1 and/or FIT2.

5. The method of claim 2, wherein the agent affects activity of FIT1 and/or FIT2.

6. The method of claim 2, wherein the agent affects FIT1.

7. The method of claim 2, wherein the agent affects FIT2.

8. The method of claim 2, wherein the agent affects FIT1 and FIT2.

9. The method of claim 1, wherein the cells are mouse embryo fibroblasts isolated from FIT2 knockout embryos, and wherein the fibroblasts are stably or transiently transfected with FIT1 and/or FIT2 under control of a regulated or constitutively active promoter.

10. The method of claim 1, wherein the agent affects expression of FIT1 and/or FIT2.

11. The method of claim 1, wherein the agent affects activity of FIT1 and/or FIT2.

12. The method of claim 1, wherein the agent affects FIT1.

13. The method of claim 1, wherein the agent affects FIT2.

14. The method of claim 1, wherein the agent affects FIT1 and FIT2.

* * * * *

SEQUENCE LISTING

```
<160> NUMBER OF SEQ ID NOS: 58

<210> SEQ ID NO 1
<211> LENGTH: 292
<212> TYPE: PRT
<213> ORGANISM: Human
<220> FEATURE:
<221> NAME/KEY: misc_feature
<223> OTHER INFORMATION: FIT1

<400> SEQUENCE: 1

Met Glu Arg Gly Pro Val Val Gly Ala Gly Leu Gly Ala Gly Ala Arg
1               5                   10                  15

Ile Gln Ala Leu Leu Gly Cys Leu Leu Lys Val Leu Leu Trp Val Ala
            20                  25                  30

Ser Ala Leu Leu Tyr Phe Gly Ser Glu Gln Ala Ala Arg Leu Leu Gly
        35                  40                  45

Ser Pro Cys Leu Arg Arg Leu Tyr His Ala Trp Leu Ala Ala Val Val
    50                  55                  60

Ile Phe Gly Pro Leu Leu Gln Phe His Val Asn Pro Arg Thr Ile Phe
65                  70                  75                  80

Ala Ser His Gly Asn Phe Phe Asn Ile Lys Phe Val Asn Ser Ala Trp
                85                  90                  95

Gly Trp Thr Cys Thr Phe Leu Gly Gly Phe Val Leu Leu Val Val Phe
            100                 105                 110

Leu Ala Thr Arg Arg Val Ala Val Thr Ala Arg His Leu Ser Arg Leu
        115                 120                 125

Val Val Gly Ala Ala Val Trp Arg Gly Ala Gly Arg Ala Phe Leu Leu
    130                 135                 140

Ile Glu Asp Leu Thr Gly Ser Cys Phe Glu Pro Leu Pro Gln Gly Leu
145                 150                 155                 160

Leu Leu His Glu Leu Pro Asp Arg Arg Ser Cys Leu Ala Ala Gly His
                165                 170                 175

Gln Trp Arg Gly Tyr Thr Val Ser Ser His Thr Phe Leu Leu Thr Phe
            180                 185                 190

Cys Cys Leu Leu Met Ala Glu Glu Ala Ala Val Phe Ala Lys Tyr Leu
```

```
                195                 200                 205
Ala His Gly Leu Pro Ala Gly Ala Pro Leu Arg Leu Val Phe Leu Leu
    210                 215                 220

Asn Val Leu Leu Gly Leu Trp Asn Phe Leu Leu Cys Thr Val
225                 230                 235                 240

Ile Tyr Phe His Gln Tyr Thr His Lys Val Val Gly Ala Ala Val Gly
                245                 250                 255

Thr Phe Ala Trp Tyr Leu Thr Tyr Gly Ser Trp Tyr His Gln Pro Trp
                260                 265                 270

Ser Pro Gly Ser Pro Gly His Gly Leu Phe Pro Arg Pro His Ser Ser
                275                 280                 285

Arg Lys His Asn
        290

<210> SEQ ID NO 2
<211> LENGTH: 262
<212> TYPE: PRT
<213> ORGANISM: Human
<220> FEATURE:
<221> NAME/KEY: misc_feature
<223> OTHER INFORMATION: FIT2

<400> SEQUENCE: 2

Met Glu His Leu Glu Arg Cys Glu Trp Leu Leu Arg Gly Thr Leu Val
1               5                   10                  15

Arg Ala Ala Val Arg Arg Tyr Leu Pro Trp Ala Leu Val Ala Ser Met
                20                  25                  30

Leu Ala Gly Ser Leu Leu Lys Glu Leu Ser Pro Leu Pro Glu Ser Tyr
            35                  40                  45

Leu Ser Asn Lys Arg Asn Val Leu Asn Val Tyr Phe Val Lys Val Ala
        50                  55                  60

Trp Ala Trp Thr Phe Cys Leu Leu Pro Phe Ile Ala Leu Thr Asn
65                  70                  75                  80

Tyr His Leu Thr Gly Lys Ala Gly Leu Val Leu Arg Arg Leu Ser Thr
                85                  90                  95

Leu Leu Val Gly Thr Ala Ile Trp Tyr Ile Cys Thr Ser Ile Phe Ser
                100                 105                 110

Asn Ile Glu His Tyr Thr Gly Ser Cys Tyr Gln Ser Pro Ala Leu Glu
            115                 120                 125

Gly Val Arg Lys Glu His Gln Ser Lys Gln Cys His Gln Glu Gly
130                 135                 140

Gly Phe Trp His Gly Phe Asp Ile Ser Gly His Ser Phe Leu Leu Thr
145                 150                 155                 160

Phe Cys Ala Leu Met Ile Val Glu Glu Met Ser Val Leu His Glu Val
                165                 170                 175

Lys Thr Asp Arg Ser His Cys Leu His Thr Ala Ile Thr Thr Leu Val
                180                 185                 190

Val Ala Leu Gly Ile Leu Thr Phe Ile Trp Val Leu Met Phe Leu Cys
            195                 200                 205

Thr Ala Val Tyr Phe His Asn Leu Ser Gln Lys Val Phe Gly Thr Leu
        210                 215                 220

Phe Gly Leu Leu Ser Trp Tyr Gly Thr Tyr Gly Phe Trp Tyr Pro Lys
225                 230                 235                 240

Ala Phe Ser Pro Gly Leu Pro Pro Gln Ser Cys Ser Leu Asn Leu Lys
                245                 250                 255

Gln Asp Ser Tyr Lys Lys
```

<210> SEQ ID NO 3
<211> LENGTH: 292
<212> TYPE: PRT
<213> ORGANISM: Mouse
<220> FEATURE:
<221> NAME/KEY: misc_feature
<223> OTHER INFORMATION: FIT1

<400> SEQUENCE: 3

Met Glu Arg Gly Pro Thr Val Gly Ala Gly Leu Gly Ala Gly Thr Arg
1               5                   10                  15

Val Arg Ala Leu Leu Gly Cys Leu Val Lys Val Leu Leu Trp Val Ala
            20                  25                  30

Ser Ala Leu Leu Tyr Phe Gly Ser Glu Gln Ala Ala Arg Leu Leu Gly
        35                  40                  45

Ser Pro Cys Leu Arg Arg Leu Tyr His Ala Trp Leu Ala Ala Val Val
    50                  55                  60

Ile Phe Gly Pro Leu Leu Gln Phe His Val Asn Ser Arg Thr Ile Phe
65                  70                  75                  80

Ala Ser His Gly Asn Phe Phe Asn Ile Lys Phe Val Asn Ser Ala Trp
                85                  90                  95

Gly Trp Thr Cys Thr Phe Leu Gly Gly Phe Val Leu Leu Val Val Phe
            100                 105                 110

Leu Ala Thr Arg Arg Val Ala Val Thr Ala Arg His Leu Ser Arg Leu
        115                 120                 125

Val Val Gly Ala Ala Val Trp Arg Gly Ala Gly Arg Ala Phe Leu Leu
    130                 135                 140

Ile Glu Asp Leu Thr Gly Ser Cys Phe Glu Pro Leu Pro Gln Gly Leu
145                 150                 155                 160

Leu Leu His Glu Leu Pro Asp Arg Lys Ser Cys Leu Ala Ala Gly His
                165                 170                 175

Gln Trp Arg Gly Tyr Thr Val Ser Ser His Thr Phe Leu Leu Thr Phe
            180                 185                 190

Cys Cys Leu Leu Met Ala Glu Glu Ala Ala Val Phe Ala Lys Tyr Leu
        195                 200                 205

Ala His Gly Leu Pro Ala Gly Ala Pro Leu Arg Leu Val Phe Leu Leu
    210                 215                 220

Asn Val Leu Leu Leu Gly Leu Trp Asn Phe Leu Leu Cys Thr Val
225                 230                 235                 240

Ile Tyr Phe His Gln Tyr Thr His Lys Val Val Gly Ala Ala Val Gly
                245                 250                 255

Thr Phe Ala Trp Tyr Leu Thr Tyr Gly Ser Trp Tyr His Gln Pro Trp
            260                 265                 270

Ser Pro Gly Ile Pro Gly His Gly Leu Phe Pro Arg Ser Arg Ser Met
        275                 280                 285

Arg Lys His Asn
    290

<210> SEQ ID NO 4
<211> LENGTH: 262
<212> TYPE: PRT
<213> ORGANISM: Mouse
<220> FEATURE:
<221> NAME/KEY: misc_feature
<223> OTHER INFORMATION: FIT2

<400> SEQUENCE: 4

```
Met Glu His Leu Glu Arg Cys Ala Trp Phe Leu Arg Gly Thr Leu Val
1               5                   10                  15

Arg Ala Thr Val Arg Arg His Leu Pro Trp Ala Leu Val Ala Ala Met
            20                  25                  30

Leu Ala Gly Ser Val Val Lys Glu Leu Ser Pro Leu Pro Glu Ser Tyr
        35                  40                  45

Leu Ser Asn Lys Arg Asn Val Leu Asn Val Tyr Phe Val Lys Leu Ala
    50                  55                  60

Trp Ala Trp Thr Val Cys Leu Leu Pro Phe Ile Ala Leu Thr Asn
65                  70                  75                  80

Tyr His Leu Thr Gly Lys Thr Ser Leu Val Leu Arg Arg Leu Ser Thr
                85                  90                  95

Leu Leu Val Gly Thr Ala Ile Trp Tyr Ile Cys Thr Ala Leu Phe Ser
            100                 105                 110

Asn Ile Glu His Tyr Thr Gly Ser Cys Tyr Gln Ser Pro Ala Leu Glu
        115                 120                 125

Gly Ile Arg Gln Glu His Arg Ser Lys Gln Gln Cys His Arg Glu Gly
    130                 135                 140

Gly Phe Trp His Gly Phe Asp Ile Ser Gly His Ser Phe Leu Leu Thr
145                 150                 155                 160

Phe Cys Ala Leu Met Ile Val Glu Glu Met Ala Val Leu His Glu Val
                165                 170                 175

Lys Thr Asp Arg Gly His His Leu His Ala Ala Ile Thr Thr Leu Val
            180                 185                 190

Val Ala Leu Gly Phe Leu Thr Phe Ile Trp Val Trp Met Phe Leu Cys
        195                 200                 205

Thr Ala Val Tyr Phe His Asp Leu Thr Gln Lys Val Phe Gly Thr Met
    210                 215                 220

Phe Gly Leu Leu Gly Trp Tyr Gly Thr Tyr Gly Tyr Trp Tyr Leu Lys
225                 230                 235                 240

Ser Phe Ser Pro Gly Leu Pro Pro Gln Ser Cys Ser Leu Thr Leu Lys
                245                 250                 255

Arg Asp Thr Tyr Lys Lys
            260

<210> SEQ ID NO 5
<211> LENGTH: 274
<212> TYPE: PRT
<213> ORGANISM: S. cerevisiae
<220> FEATURE:
<221> NAME/KEY: misc_feature
<223> OTHER INFORMATION: YDR319 FIT

<400> SEQUENCE: 5

Met Ile Arg Gln Leu Asn Tyr Trp Ser Arg Lys Ala Tyr Leu Ile Tyr
1               5                   10                  15

Pro Phe Gln Val Phe Val Gly Ala Leu Leu Ser Ile Val Val Ser Ser
            20                  25                  30

Glu Thr Leu Asn His Gln Lys Glu Thr Cys Ala Leu Leu Lys Ser Ser
        35                  40                  45

Asn Ile Phe Asn Val Ile Phe Ala Tyr Lys Ala Asn Gln Leu Trp Pro
    50                  55                  60

Phe Leu Phe Phe Ser Leu Ala Phe Leu Gln Ile Tyr Phe His Tyr Leu
65                  70                  75                  80

Ala Arg Met Asp Ile Leu Pro Leu Pro Ile Ser Ser Thr Glu Thr Ser
                85                  90                  95
```

-continued

```
Ser Ser Tyr Leu Thr Tyr Thr Asn His Trp Pro Leu Leu Lys Asn Arg
            100                 105                 110

Ile Ile Ser Ile Met Ile Thr Gln Tyr Ala Cys Lys Phe Val Leu Lys
            115                 120                 125

Tyr Leu Leu Leu Phe Leu Asn Phe Gln Phe Ile Asp His Val Phe Ile
130                 135                 140

Trp Thr Gly Gly Glu Cys Ser Ser Gly Ser Lys Thr Thr Ser Ala Glu
145                 150                 155                 160

Lys Cys Arg Leu Glu Asn Gly Lys Trp Asp Gly Phe Asp Ile Ser
            165                 170                 175

Gly His Phe Cys Phe Leu Val Ser Ile Ser Met Ile Leu Trp Met Glu
            180                 185                 190

Leu His Leu Phe Ser Arg Phe Val Gln Ala Glu Asp Met Phe Trp Val
            195                 200                 205

Val Asn Lys Trp Val Arg Ala Cys Leu Ala Ile Val Cys Ala Val Leu
            210                 215                 220

Val Ile Trp Ile Cys Ile Leu Trp Val Thr Ala Ile Tyr Tyr His Thr
225                 230                 235                 240

Ile Leu Glu Lys Val Leu Gly Cys Leu Met Gly Phe Ile Cys Pro Val
            245                 250                 255

Phe Ile Tyr His Ile Leu Pro Lys Ile Gly Ile Leu His Asn Tyr Leu
            260                 265                 270

Tyr Leu

<210> SEQ ID NO 6
<211> LENGTH: 380
<212> TYPE: PRT
<213> ORGANISM: S. cerevisiae
<220> FEATURE:
<221> NAME/KEY: misc_feature
<223> OTHER INFORMATION: SCS3 FIT

<400> SEQUENCE: 6

Met Ser Ser Lys Trp Phe Asn Ala Ile His Leu Leu Val Cys Pro Leu
1               5                   10                  15

Thr Val Leu Val Gly Tyr Leu Met Asn Ala Tyr Gly Tyr Gly Ala Ala
            20                  25                  30

Leu Gln Ala Thr Leu Asn Lys Asp Gly Leu Val Asn Ala Met Leu Val
            35                  40                  45

Lys Lys Gly Trp Phe Trp Thr Ser Leu Val Gly Trp Trp Cys Ile Ile
50                  55                  60

Arg Tyr Arg Ala Val Pro Gly Ala Thr Gly Arg Asp Arg Arg His Ile
65                  70                  75                  80

Val Gln Ser Phe Lys Arg Tyr Ala Ile Leu Thr Val Trp Trp Tyr Val
            85                  90                  95

Phe Thr Gln Gly Ile Trp Phe Gly Val Gly Pro Ile Met Asp Leu Val
            100                 105                 110

Phe Val Tyr Thr Gly Gly His Cys His Tyr Asp Val Phe Asp Ala
            115                 120                 125

Gly His Val Asn Glu Asp Phe Gln Gly Ser Val Thr Arg Thr Asn Arg
130                 135                 140

Ala Leu Ala Leu Ile His Asn Val Leu Thr Leu His Gly His His Gln
145                 150                 155                 160

Glu His Arg Gln Gln Gln Leu Trp Asp Arg Ser Ile Gly Ser Ile Gln
            165                 170                 175
```

```
Gly Ala Leu Gln Ala Thr Gln Pro Lys Thr Pro Lys Asn Val Thr Ala
            180                 185                 190

Ser Ala Ala Ala Ile Asn Thr Phe Ile His Asp Gln Met His Arg
        195                 200                 205

Trp Gln Gly Pro Leu Thr Thr Ser Ala Gln Cys Arg Arg Phe Gly Gly
210                 215                 220

His Trp Ala Gly Gly His Asp Pro Ser Gly His Val Phe Leu Ala Thr
225                 230                 235                 240

Leu Met Cys Met Phe Leu Leu Gly Glu Leu Arg Val Phe Gly Arg Arg
                245                 250                 255

Ala Leu Ala His Leu Tyr Ala Gln Lys Trp Gln Leu Val Arg Leu Val
            260                 265                 270

Thr Arg Leu Phe Asp Thr Gly Pro Leu Trp Thr Trp Arg Arg Cys Gly
        275                 280                 285

Gly Gly Ser Met Thr Cys Gly Ala Arg Leu Trp Arg Ala Ile Val Glu
    290                 295                 300

Pro Pro Val Thr Cys Ala Ala Leu Leu Arg Leu Thr Arg Cys Ile
305                 310                 315                 320

Ala Cys Asp His Pro Val Ile Ile Leu Leu Thr Leu Leu Val Thr Trp
                325                 330                 335

Leu Trp Gln Leu Leu Leu Thr Ala Val Ala Ser Arg Phe His Thr Val
            340                 345                 350

Arg Glu His Met Ser Gly Leu Leu Ala Ala Tyr Ile Val Thr Gly Leu
        355                 360                 365

Val Tyr Ala Arg Asp Ala Ala Leu Arg Pro Val
370                 375                 380

<210> SEQ ID NO 7
<211> LENGTH: 283
<212> TYPE: PRT
<213> ORGANISM: C.elegans
<220> FEATURE:
<221> NAME/KEY: misc_feature
<223> OTHER INFORMATION: FIT

<400> SEQUENCE: 7

Met Ser Thr Arg Arg Ser Ser Thr Arg Ala Asp Ser Thr Thr Lys Arg
1               5                   10                  15

Pro Ala Ser Pro Asn Ser Thr Pro Asn Ala Ala Leu Gly Ile Phe Val
            20                  25                  30

Ala Ile Ala Arg Gln Ile Leu Phe Ile Asp Ala Arg Lys Val Ala Leu
        35                  40                  45

Phe Tyr Leu Ala Phe Val Thr Val Leu Ser Phe Ile Glu Ser Arg Ile
50                  55                  60

Glu Leu Asp Ser Thr Tyr Tyr Leu Val Gln Lys His Ser Val Leu Asn
65                  70                  75                  80

Gln Tyr Gly Val Lys Met Gly Trp Phe Trp Thr Leu Val Ile Val Gly
                85                  90                  95

Pro Phe Ile Trp Phe Ser Ser Lys Ala His Asn Arg Arg Asp Arg Asp
            100                 105                 110

Gln Pro Ile Val Asp Val Cys Arg Leu Gly Val Gly Thr Ala Cys Trp
        115                 120                 125

Tyr Phe Ser Val Gln Phe Phe His Lys Val Leu Ala Leu Thr Ser Met
130                 135                 140

Cys Asp Lys Gly Arg Thr Leu Thr Arg Ala Gln Cys Ser Glu Lys Glu
145                 150                 155                 160
```

-continued

```
Gly Val Trp Thr Pro Gly Tyr Asp Ile Ser Gly His Cys Phe Leu Met
                165                 170                 175

Ile Tyr Ser Ile Leu Ile Ile Thr Glu Ala Ile Ala Tyr Arg His
            180                 185                 190

Tyr Gln Gln Val Thr Asp Ala Val His Gln Met Asp Gly Asp Arg Glu
        195                 200                 205

Glu His Asp Arg Leu Thr Arg Cys Ile Gln Tyr Phe Phe Val Ala Met
    210                 215                 220

Leu Phe Leu His Ala Phe Trp Phe Lys Gln Ile Ile Ile Ser Val Leu
225                 230                 235                 240

Tyr Tyr His Ile Phe Ile Glu Glu Ile Leu Gly Ala Val Ala Ala Val
                245                 250                 255

Val Cys Trp Phe Val Thr Tyr Arg Met Leu Tyr Pro Ala Gly Phe Leu
            260                 265                 270

Ala Ser Pro Ile Arg Arg Thr Val Gly Arg Lys
        275                 280

<210> SEQ ID NO 8
<211> LENGTH: 423
<212> TYPE: PRT
<213> ORGANISM: D.melanogaster
<220> FEATURE:
<221> NAME/KEY: misc_feature
<223> OTHER INFORMATION: FIT

<400> SEQUENCE: 8

Met Ala Thr Lys Arg Arg Pro Leu Arg Pro Asn Leu Gly Gly Thr Ala
1               5                   10                  15

Gly Ser Pro Ser Ser Gly Ser Asn Met Asn Phe Arg Pro Gly Gly
            20                  25                  30

Pro Asp Ile Thr Arg Ser Glu Ala Arg Gly Thr Arg Pro Thr Ala Ala
        35                  40                  45

Pro Thr Ser Ile Arg Glu Ile Leu Val Met Gly Val Ile His Leu Cys
    50                  55                  60

Lys Lys Thr Ile Phe Phe Asn Thr Asp Leu Lys Val Ala Leu Tyr Leu
65                  70                  75                  80

Gly Ser Leu Phe Val Ile Ser Val Ile Gly Asp Phe Val Pro Phe Pro
                85                  90                  95

Lys Thr Tyr Phe Ala Arg Ser Asp Asn Leu Phe Asn Gln Tyr Phe Val
            100                 105                 110

Lys Ile Gly Trp Gly Trp Thr Leu Leu Phe Val Val Pro Phe Leu Val
        115                 120                 125

Leu Ser Ala Tyr Thr Ile Thr Cys Gly Asp His Lys Arg Met Leu Arg
    130                 135                 140

His His Phe Pro Arg Ile Val Ile Ala Thr Phe Phe Trp Phe Phe Trp
145                 150                 155                 160

Thr Lys Leu Phe Asn Val Val Glu Asn Ser Tyr Gly Arg Cys Thr Thr
                165                 170                 175

Lys Gly Tyr Ala Thr Lys Ser Ser Cys Leu Lys Ala Gly His Leu Trp
            180                 185                 190

Lys Gly Phe Asp Ile Ser Gly His Ala Phe Ile Leu Ile His Ser Ser
        195                 200                 205

Leu Val Leu Ile Glu Glu Ala Arg Pro Ile Ile Arg Trp Glu Thr Ile
    210                 215                 220

Lys Glu His Ile Arg Asn Glu Arg His Asn Arg Ser Thr Ala Glu Asn
225                 230                 235                 240
```

```
Ser Gly Thr Asn Pro Leu Arg Thr Leu Asn Glu Glu Gln Met Arg Ser
            245                 250                 255

Leu Gln Phe Leu Tyr Lys Arg Leu Thr Pro Ile Ile Arg Thr Leu Phe
            260                 265                 270

Ile Gly Met Ala Ala Leu Gln Leu Leu Trp Asp Ile Met Leu Val Gly
            275                 280                 285

Thr Met Leu Tyr Tyr His Arg Met Ile Glu Lys Val Ile Ser Gly Ile
            290                 295                 300

Ile Ala Ile Leu Thr Trp Tyr Phe Thr Tyr Arg Phe Trp Tyr Pro Thr
305                 310                 315                 320

Pro Gly Leu Leu Pro Glu Ala Pro Gly Asn Gly Ser Phe Ser Tyr Gln
            325                 330                 335

Arg Glu Ile Pro Thr Phe Pro Phe Lys Arg Pro Ser His Leu Ser Thr
            340                 345                 350

Gly Ala Ala Thr Thr Ser Ser Gly Ser Asn Ser Ser Arg Thr Asn Leu
            355                 360                 365

Asn Gly Lys Ala Ala Thr Thr Gly Val Pro Arg Asp Gln Gln Ile Pro
            370                 375                 380

Thr Phe Met Gly Met Pro Leu Phe Thr Ser Pro Lys Ala Ala Ser Ala
385                 390                 395                 400

Ala Ala Asn Leu Leu Met Ser Asp Gln Gln Lys Arg Glu Arg Asp Arg
            405                 410                 415

Glu Gln Gln Thr Leu Glu Ser
            420

<210> SEQ ID NO 9
<211> LENGTH: 242
<212> TYPE: PRT
<213> ORGANISM: A.gambiae
<220> FEATURE:
<221> NAME/KEY: misc_feature
<223> OTHER INFORMATION: FIT

<400> SEQUENCE: 9

Met Ala Ser Lys Arg Lys Pro Ile His Thr Pro Ser Ala Ala Gly Ala
1               5                   10                  15

Ala Gly Gly Asn Ala Ala Arg Pro Gln Met Asn Phe Arg Gln Gly Leu
            20                  25                  30

Asn Asp Thr Thr Ala Arg Ala Glu Ala Lys Gly Thr Arg Pro Thr Ala
            35                  40                  45

Thr Pro Thr Ser Ile Arg Glu Val Leu Thr Met Met Val Leu His Val
            50                  55                  60

Cys Lys Lys Ile Ile Phe Phe Asp Thr Ser Leu Lys Val Pro Leu Tyr
65                  70                  75                  80

Leu Gly Ser Leu Phe Ile Val Ser Leu Ile Gly Asp Phe Leu Pro Tyr
            85                  90                  95

Pro Lys Thr Tyr Leu Ala Arg Thr Asp Asn Leu Phe Asn Val Tyr Phe
            100                 105                 110

Val Lys Leu Gly Trp Ala Trp Thr Leu Leu Phe Ala Phe Pro Tyr Leu
            115                 120                 125

Ala Met Thr Ser Ile Thr Ile Cys Cys Gly Asp Asn Gln Arg Leu Ile
            130                 135                 140

Arg Asn His Leu Pro Arg Leu Gly Ile Ala Thr Val Phe Trp Phe Val
145                 150                 155                 160

Trp Thr Lys Leu Phe Asn Val Ile Glu Ser Ser Tyr Gly Arg Cys Ser
            165                 170                 175
```

```
Val Arg Gly Phe Asp Ala Lys Thr Pro Cys Leu Lys Ala Gly His Leu
            180                 185                 190

Trp Asn Gly Phe Asp Ile Ser Gly His Ala Phe Ile Leu Ile Tyr Ser
            195                 200                 205

Ser Leu Val Leu Met Glu Glu Ala Arg Pro Ile Ile Gly Trp Glu Ser
    210                 215                 220

Ile Lys Asp Leu Leu Arg Asn Glu Glu His Asn Arg Ser Asn Asn Asp
225                 230                 235                 240

Asn Ser
```

<210> SEQ ID NO 10
<211> LENGTH: 288
<212> TYPE: PRT
<213> ORGANISM: T.nigroviridis
<220> FEATURE:
<221> NAME/KEY: misc_feature
<223> OTHER INFORMATION: FIT

<400> SEQUENCE: 10

```
Arg Val Thr Ala Ala Leu Arg Ala Ala Ala Arg Arg Phe Leu Gly Leu
1               5                   10                  15

Leu Asn Ala Ala Leu Val Leu Ala Ser Asp Leu Leu Ala Arg Leu Phe
            20                  25                  30

Gly Ser Gly Pro Val Arg Arg His Phe His Leu Leu Leu Ser Ser Leu
            35                  40                  45

Val Leu Leu Gly Pro Ala Leu Ser Phe Trp Val Ser Lys Tyr Ser Ile
        50                  55                  60

Phe Ala Asn Ser His Asn Tyr Leu Tyr Arg Lys Phe Leu Gly Ser Thr
65                  70                  75                  80

Trp Gly Trp Thr Cys Thr Leu Thr Gly Ser Phe Val Leu Leu Leu Ser
                85                  90                  95

Ile Ser Ala Arg Arg Ser Ala Ser Thr Ser Leu Lys His Leu Ser Arg
            100                 105                 110

Leu Val Val Leu Gly Leu Leu Trp Gly Gly Cys Arg Cys Leu Leu Thr
            115                 120                 125

Leu Leu Glu Asp Ala Ala Gly Ala Cys Tyr Glu Pro Leu Ser Ser Gly
    130                 135                 140

Pro Glu Ser Glu Gly Leu Ala Ser Pro Leu Gln Pro Leu Leu Leu Leu
145                 150                 155                 160

His Glu Asp Gln Ser Lys Ala Ser Cys Leu Lys Ala Gly Leu Leu Trp
                165                 170                 175

Arg Gly Tyr Gln Val Ser Gln Glu Val Leu Val Leu Cys Leu Cys Cys
            180                 185                 190

Leu Ala Leu Val Glu Glu Val Ser Val Phe Arg Phe His Leu Asp Gln
            195                 200                 205

Ala Ala Ser Leu His Arg Pro Pro Ile Gly Pro Leu Arg Cys Leu Phe
        210                 215                 220

Leu Leu Cys Val Leu Leu Gly Leu Trp Val Phe Leu Leu Leu Leu Cys
225                 230                 235                 240

Leu Leu Ala His Phe Pro Gln Phe Pro Ser Gln Gln Leu Gly Gly Ala
                245                 250                 255

Val Gly Tyr Leu Gly Trp Arg Gly Leu Tyr Gln Gly Trp Phe Arg Leu
            260                 265                 270

Pro Pro Ser Trp Met Cys Pro Gly Leu Pro Gly Glu Gly Leu Leu Pro
            275                 280                 285
```

```
<210> SEQ ID NO 11
<211> LENGTH: 290
<212> TYPE: PRT
<213> ORGANISM: D.rerio
<220> FEATURE:
<221> NAME/KEY: misc_feature
<223> OTHER INFORMATION: FIT

<400> SEQUENCE: 11

Met Phe Leu Asn Ser Ile Leu Val Val Ile Thr Asp Leu Ala Ala Gly
1               5                   10                  15

Leu Leu Gly Asn Thr Ser Phe Arg Arg His Phe His Leu Leu Leu Ser
            20                  25                  30

Ala Leu Leu Phe Gly Pro Leu Leu Ser Leu Trp Val Ser His Tyr
        35                  40                  45

Ser Val Phe Ala Lys Arg Thr His Phe Leu Tyr Arg Val Phe Leu Arg
    50                  55                  60

Ser Gly Trp Gly Trp Thr Cys Ile Phe Val Gly Ser Phe Val Phe Val
65                  70                  75                  80

Leu Ser Phe Ser Val Arg Arg Ser Leu Thr Leu Ser Leu Arg His Leu
                85                  90                  95

Ser Arg Leu Ala Val Ala Gly Gly Leu Trp Leu Gly Phe Arg Lys Leu
            100                 105                 110

Leu Cys Leu Leu Glu Asn Ala Thr Gly Ser Cys Tyr Glu Pro Leu Ser
        115                 120                 125

Ala Ala Leu Glu Met Thr Ser Gly Thr Asn Gly Glu Gly Gln Pro Leu
    130                 135                 140

Leu Leu Leu Arg Glu Ala Glu Thr Lys Glu Thr Cys Val Arg Ser Gly
145                 150                 155                 160

Met Leu Trp Arg Gly Tyr Glu Val Ser Glu Asp Ala Leu Leu Leu Cys
                165                 170                 175

Leu Cys Cys Leu Leu Leu Ala Glu Glu Thr Ala Val Phe Gly Pro Tyr
            180                 185                 190

Leu Asn Leu Gly Gly Pro Ser Glu Ala Pro Leu Arg Ile Leu Phe Leu
        195                 200                 205

Phe Cys Val Leu Leu Leu Ser Leu Trp Val Phe Leu Leu Cys Leu
    210                 215                 220

Leu Ala Tyr Phe Pro Glu Phe Pro Thr Gln Leu Leu Gly Gly Ala Leu
225                 230                 235                 240

Gly Cys Leu Ser Trp Arg Ala Leu Tyr Gln Gly Trp Tyr Arg Leu Arg
                245                 250                 255

Pro Ser Trp Tyr Cys Pro Gly Arg Pro Gly Val Gly Leu Leu Ser Thr
            260                 265                 270

Gln Ser Lys Gln Asp Glu Leu Leu Glu Thr Gln Thr Asn Ala Lys Glu
        275                 280                 285

Ile Asp
    290

<210> SEQ ID NO 12
<211> LENGTH: 260
<212> TYPE: PRT
<213> ORGANISM: X.laevis
<220> FEATURE:
<221> NAME/KEY: misc_feature
<223> OTHER INFORMATION: FIT

<400> SEQUENCE: 12

Met Glu Arg Leu Glu Asn Cys Ala Gln Met Phe Gln Arg Lys Phe Leu
1               5                   10                  15
```

Asn Glu Ala Phe Arg Arg His Cys Pro Val Leu Leu Ala Cys Ile Ala
            20                  25                  30

Leu Gly Gly Ser Leu Leu Lys Glu Leu Ser Pro Leu Pro Asp Ser Tyr
        35                  40                  45

Trp Asn Asn Lys Arg Asn Val Leu Asn Val Tyr Phe Val Lys Phe Cys
 50                  55                  60

Trp Gly Trp Thr Leu Trp Leu Leu Pro Phe Ile Thr Leu Thr Asn
 65                  70                  75                  80

Tyr Lys Leu Thr Gly Ser Ile Thr Lys Val Leu Arg Arg Leu Ser Ser
            85                  90                  95

Leu Leu Val Gly Thr Leu Phe Trp Tyr Leu Cys Thr Asn Leu Phe Leu
        100                 105                 110

Tyr Ile Glu His Ile Thr Gly Ser Cys Tyr Glu Ser Glu Ala Leu Leu
    115                 120                 125

Asp Ser Ile Glu His Gln Asp Arg Lys Glu Cys Arg Leu His Gly Gly
130                 135                 140

Phe Trp His Gly Phe Asp Ile Ser Gly His Cys Phe Leu Leu Ser Tyr
145                 150                 155                 160

Cys Ile Leu Ile Ile Leu Glu Glu Thr Ser Val Ile Arg Ser Ile Gln
                165                 170                 175

Phe Glu Arg His Trp His Arg Met Ala Ile Asn Ala Gln Phe Thr Ala
            180                 185                 190

Leu Ser Ile Leu Val Ile Ile Trp Val Trp Met Phe Leu Cys Thr Ala
        195                 200                 205

Val Tyr Phe His Asn Ile Phe Gln Lys Val Ile Gly Thr Ala Phe Gly
    210                 215                 220

Met Leu Ala Trp Tyr Ile Thr Tyr Arg Trp Trp Tyr Leu Gln Pro Ile
225                 230                 235                 240

Ser Pro Gly Leu Pro Pro Ala Ser Ala Ser His Ser Glu Lys Glu Pro
                245                 250                 255

Val Tyr Lys Asn
            260

<210> SEQ ID NO 13
<211> LENGTH: 271
<212> TYPE: PRT
<213> ORGANISM: G.gallus
<220> FEATURE:
<221> NAME/KEY: misc_feature
<223> OTHER INFORMATION: FIT

<400> SEQUENCE: 13

Met Glu Arg Leu Glu Arg Cys Ala Arg Cys Leu Arg Ala Arg Leu Val
1               5                   10                  15

Ala Ala Ala Val Arg Arg Arg Leu Pro Trp Leu Leu Leu Gly Leu Val
            20                  25                  30

Phe Leu Gly Ser Ala Leu Lys Asp Gly Asp Leu Val Pro Glu Thr Pro
        35                  40                  45

Met Gln Asn Lys Arg Asn Val Phe Asn Val Tyr Phe Val Lys Val Ala
    50                  55                  60

Trp Ala Trp Thr Phe Trp Leu Leu Pro Phe Ile Gly Val Thr Thr
 65                  70                  75                  80

Tyr Leu Phe Ala Lys Ser Lys Phe Leu Tyr Gly Pro Thr Lys Ser Ile
            85                  90                  95

Leu Ala Ala Leu Arg Arg Leu Ser Thr Leu Leu Val Gly Thr Ala Val
        100                 105                 110

```
Trp Tyr Val Cys Thr Glu Leu Phe Met Tyr Ile Glu Asn Leu Thr Gly
            115                 120                 125

Thr Cys Ser Thr Ser Ser Lys Leu Ser Glu Pro His Gln Leu Tyr Ala
130                 135                 140

Thr Lys Gln Glu Cys His Arg Asn Asn Gly Ile Trp Asn Gly Phe Asp
145                 150                 155                 160

Ile Ser Gly His Cys Phe Leu Leu Ser Tyr Cys Ala Leu Met Ile Val
                165                 170                 175

Glu Glu Met Ala Val Leu Glu Gly Leu Ser Ile Asp Arg Asn Ser Arg
            180                 185                 190

Leu Arg Val Val Ile Asn Gly Leu Phe Val Ser Leu Cys Phe Leu Thr
        195                 200                 205

Met Ile Trp Val Phe Met Phe Leu Cys Thr Thr Val Tyr Phe His Asp
    210                 215                 220

Phe Ser Gln Lys Leu Leu Gly Ala Leu Ile Gly Leu Ala Ala Trp Tyr
225                 230                 235                 240

Ala Thr Tyr Arg Val Trp Tyr Leu Lys Pro Phe Ser Pro Gly Leu Pro
                245                 250                 255

Leu Pro Asn Ile Pro Leu Ser Ser Lys Lys Tyr Ser Tyr Ser Arg
            260                 265                 270

<210> SEQ ID NO 14
<211> LENGTH: 262
<212> TYPE: PRT
<213> ORGANISM: P.troglodytes
<220> FEATURE:
<221> NAME/KEY: misc_feature
<223> OTHER INFORMATION: FIT2

<400> SEQUENCE: 14

Met Glu His Leu Glu Arg Cys Glu Trp Leu Leu Arg Gly Thr Leu Val
1               5                   10                  15

Arg Ala Ala Val Arg Arg Tyr Leu Pro Trp Ala Leu Val Ala Ser Met
            20                  25                  30

Leu Ala Gly Ser Leu Leu Lys Glu Leu Ser Pro Leu Pro Glu Ser Tyr
        35                  40                  45

Leu Ser Asn Lys Arg Asn Val Leu Asn Val Tyr Phe Val Lys Val Ala
    50                  55                  60

Trp Ala Trp Thr Phe Cys Leu Leu Pro Phe Ile Ala Leu Thr Asn
65                  70                  75                  80

Tyr His Leu Thr Gly Lys Ala Gly Leu Val Leu Arg Arg Leu Ser Thr
                85                  90                  95

Leu Leu Val Gly Thr Ala Ile Trp Tyr Ile Cys Thr Ser Ile Phe Ser
            100                 105                 110

Asn Ile Glu His Tyr Thr Gly Ser Cys Tyr Gln Ser Pro Ala Leu Glu
        115                 120                 125

Gly Val Arg Lys Glu His Gln Ser Lys Gln Gln Cys His Gln Glu Gly
    130                 135                 140

Gly Phe Trp His Gly Phe Asp Ile Ser Gly His Ser Phe Leu Leu Thr
145                 150                 155                 160

Phe Cys Ala Leu Met Ile Val Glu Glu Met Ser Val Leu His Glu Val
                165                 170                 175

Lys Thr Asp Arg Ser His Cys Leu His Thr Ala Ile Thr Thr Leu Val
            180                 185                 190

Val Ala Leu Gly Ile Leu Thr Phe Ile Trp Val Leu Met Phe Leu Cys
        195                 200                 205
```

```
Thr Ala Val Tyr Phe His Asn Leu Ser Gln Lys Val Phe Gly Thr Leu
        210                 215                 220

Phe Gly Leu Leu Ser Trp Tyr Gly Thr Tyr Gly Phe Trp Tyr Pro Lys
225                 230                 235                 240

Ala Phe Ser Pro Gly Leu Pro Pro Gln Ser Cys Ser Leu Asn Leu Lys
                245                 250                 255

Gln Asp Ser Tyr Lys Lys
            260
```

<210> SEQ ID NO 15
<211> LENGTH: 262
<212> TYPE: PRT
<213> ORGANISM: C.familiaris
<220> FEATURE:
<221> NAME/KEY: misc_feature
<223> OTHER INFORMATION: FIT2

<400> SEQUENCE: 15

```
Met Glu His Leu Glu Arg Cys Ala Arg Leu Leu Arg Gly Thr Leu Val
1               5                   10                  15

Arg Ala Ala Val Arg Arg Tyr Leu Pro Trp Ala Leu Ala Phe Ser Met
            20                  25                  30

Leu Ala Gly Ser Val Leu Lys Glu Leu Ser Pro Leu Pro Glu Ser Tyr
        35                  40                  45

Leu Ser Asn Lys Arg Asn Val Leu Asn Val Tyr Phe Val Lys Leu Ala
    50                  55                  60

Trp Ala Trp Thr Phe Cys Leu Leu Pro Phe Ile Ala Leu Thr Asn
65                  70                  75                  80

Tyr His Leu Thr Gly Arg Ala Gly Leu Val Leu Arg Arg Leu Ser Thr
                85                  90                  95

Leu Leu Val Gly Thr Ala Ile Trp Tyr Val Cys Thr Ala Ile Phe Ser
            100                 105                 110

Asn Ile Glu Asp Tyr Thr Gly Ser Cys Tyr Gln Ser Pro Thr Leu Glu
        115                 120                 125

Gly Val Arg Lys Glu His Gln Ser Lys Gln Cys His Gly Glu Gly
    130                 135                 140

Gly Phe Trp His Gly Phe Asp Ile Ser Gly His Ser Phe Leu Leu Thr
145                 150                 155                 160

Phe Cys Ala Leu Met Ile Val Glu Glu Met Ala Val Leu His Glu Leu
                165                 170                 175

Lys Met Asp Arg Ser His Cys Leu His Thr Ala Ile Thr Thr Leu Val
            180                 185                 190

Val Ala Leu Gly Phe Leu Thr Phe Ile Trp Val Trp Met Phe Leu Cys
        195                 200                 205

Thr Ala Val Tyr Phe His Asn Leu Ser Gln Lys Val Phe Gly Thr Leu
    210                 215                 220

Phe Gly Leu Leu Gly Trp Tyr Gly Thr Tyr Gly Phe Trp Tyr Leu Lys
225                 230                 235                 240

Ser Phe Ser Pro Gly Leu Pro Pro Gln Ser Ser Ser Leu Asn Leu Lys
                245                 250                 255

Gln Asp Ser Tyr Lys Lys
            260
```

<210> SEQ ID NO 16
<211> LENGTH: 262
<212> TYPE: PRT
<213> ORGANISM: B.taurus

```
<220> FEATURE:
<221> NAME/KEY: misc_feature
<223> OTHER INFORMATION: FIT2

<400> SEQUENCE: 16

Met Glu His Leu Glu Arg Cys Ala Trp Val Leu Arg Gly Thr Leu Val
1               5                   10                  15

Arg Ser Ala Val Arg Lys Tyr Leu Pro Trp Ala Leu Ala Ala Ser Met
            20                  25                  30

Leu Ala Gly Ser Leu Leu Lys Glu Leu Ser Pro Leu Pro Glu Ser Tyr
        35                  40                  45

Leu Ser Asn Lys Arg Asn Val Leu Asn Val Tyr Phe Val Lys Val Ala
    50                  55                  60

Trp Ala Trp Thr Phe Cys Leu Leu Pro Phe Ile Ala Leu Thr Asn
65                  70                  75                  80

Tyr His Leu Thr Gly Lys Ala Gly Leu Val Leu Arg Arg Leu Ser Thr
                85                  90                  95

Leu Leu Val Gly Thr Ala Ile Trp Tyr Val Cys Thr Ala Ile Phe Ser
            100                 105                 110

Asn Ile Glu His Tyr Thr Gly Ser Cys Tyr Gln Ser Pro Ala Leu Glu
        115                 120                 125

Gly Glu Arg Lys Glu His Gln Ser Lys Gln Cys His Gly Glu Gly
    130                 135                 140

Gly Phe Trp His Gly Phe Asp Ile Ser Gly His Ser Phe Leu Leu Thr
145                 150                 155                 160

Phe Cys Ala Leu Met Ile Val Glu Glu Met Ala Val Leu His Glu Val
                165                 170                 175

Lys Thr Asp Arg Asn His Cys Leu His Ala Ala Ile Thr Thr Leu Val
            180                 185                 190

Val Ala Leu Gly Phe Leu Thr Phe Ile Trp Val Trp Met Phe Leu Cys
        195                 200                 205

Thr Ala Val Tyr Phe His Asn Leu Ser Gln Lys Val Phe Gly Thr Leu
    210                 215                 220

Phe Gly Leu Leu Gly Trp Tyr Gly Thr Tyr Gly Cys Trp Tyr Leu Lys
225                 230                 235                 240

Ser Phe Ser Pro Gly Leu Pro Pro Gln Ser Ser Leu Asn Leu Lys
                245                 250                 255

Gln Asp Thr Tyr Lys Lys
            260

<210> SEQ ID NO 17
<211> LENGTH: 300
<212> TYPE: PRT
<213> ORGANISM: P.troglodytes
<220> FEATURE:
<221> NAME/KEY: misc_feature
<223> OTHER INFORMATION: FIT1

<400> SEQUENCE: 17

Met Asp Lys Asp Ser Pro Glu Gln Leu Ala Leu Arg Tyr Glu Leu Glu
1               5                   10                  15

His Gly Pro Gly Ala Arg Ala Arg Ile Gln Ala Leu Leu Asp Cys Leu
            20                  25                  30

Val Lys Val Leu Leu Trp Val Ala Ser Ala Leu Leu Tyr Phe Gly Ser
        35                  40                  45

Glu Gln Ala Ala Arg Leu Leu Gly Ser Pro Cys Leu Arg Arg Leu Tyr
    50                  55                  60
```

His Ala Trp Leu Ala Val Val Ile Phe Gly Pro Leu Leu Gln Phe
 65                  70                  75                  80

His Val Asn Pro Arg Thr Ile Phe Ala Ser His Gly Asn Phe Phe Asn
                 85                  90                  95

Ile Lys Phe Val Asn Ser Ala Trp Gly Trp Thr Cys Thr Phe Leu Gly
            100                 105                 110

Gly Phe Val Leu Val Val Phe Leu Ala Thr Arg Val Ala Val
        115                 120                 125

Thr Ala Arg His Leu Ser Arg Leu Val Val Gly Ala Ala Val Trp Arg
130                 135                 140

Gly Ala Gly Arg Ala Phe Leu Leu Ile Glu Asp Leu Thr Gly Ser Cys
145                 150                 155                 160

Phe Glu Pro Leu Pro Gln Gly Leu Leu Leu His Glu Leu Pro Asp Arg
                165                 170                 175

Arg Ser Cys Leu Ala Ala Gly His Gln Trp Arg Gly Tyr Thr Val Ser
            180                 185                 190

Ser His Thr Phe Leu Leu Thr Phe Cys Cys Leu Leu Met Ala Glu Glu
        195                 200                 205

Ala Ala Val Phe Ala Lys Tyr Leu Ala His Gly Leu Pro Ala Gly Ala
210                 215                 220

Pro Leu Arg Leu Val Phe Leu Leu Asn Val Leu Leu Gly Leu Trp
225                 230                 235                 240

Asn Phe Leu Leu Leu Cys Thr Val Ile Tyr Phe His Gln Tyr Thr His
                245                 250                 255

Lys Val Val Gly Ala Ala Val Gly Thr Phe Ala Trp Tyr Leu Thr Tyr
            260                 265                 270

Gly Ser Trp Tyr His Gln Pro Trp Ser Pro Gly Ser Pro Gly His Gly
        275                 280                 285

Leu Phe Pro Arg Pro His Ser Ser Arg Lys His Asn
290                 295                 300

<210> SEQ ID NO 18
<211> LENGTH: 292
<212> TYPE: PRT
<213> ORGANISM: C.familiaris
<220> FEATURE:
<221> NAME/KEY: misc_feature
<223> OTHER INFORMATION: FIT1

<400> SEQUENCE: 18

Met Glu Arg Gly Pro Ala Val Gly Ala Gly Leu Gly Ala Gly Ala Arg
1               5                   10                  15

Ile Arg Ala Leu Leu Gly Cys Leu Val Lys Val Leu Leu Trp Val Ala
            20                  25                  30

Ser Ala Leu Leu Tyr Phe Gly Ser Glu Gln Ala Ala Arg Leu Leu Gly
        35                  40                  45

Ser Pro Cys Leu Arg Arg Leu Tyr His Ala Trp Leu Ala Ala Val Val
    50                  55                  60

Ile Phe Gly Pro Leu Leu Gln Phe His Val Asn Pro Arg Thr Ile Phe
65                  70                  75                  80

Ala Ser His Gly Asn Phe Phe Asn Ile Lys Phe Val Asn Ser Ala Trp
                85                  90                  95

Gly Trp Thr Cys Thr Phe Leu Gly Gly Phe Val Leu Val Val Phe
            100                 105                 110

Leu Ala Thr Arg Arg Val Ala Val Thr Ala Arg His Leu Ser Arg Leu
        115                 120                 125

```
Val Val Gly Ala Ala Val Trp Arg Gly Ala Gly Arg Ala Phe Leu Leu
    130                 135                 140
Ile Glu Asp Leu Thr Gly Ser Cys Phe Glu Pro Leu Pro Gln Gly Leu
145                 150                 155                 160
Leu Leu His Glu Leu Pro Asp Arg Arg Ser Cys Leu Ala Ala Gly His
                165                 170                 175
Gln Trp Arg Gly Tyr Thr Val Ser Ser His Thr Phe Leu Leu Thr Phe
                180                 185                 190
Cys Cys Leu Leu Met Ala Glu Ala Ala Val Phe Ala Lys Tyr Leu
                195                 200                 205
Ala His Gly Leu Pro Ala Gly Ala Pro Leu Arg Leu Val Phe Leu Leu
    210                 215                 220
Asn Val Leu Leu Gly Leu Trp Asn Phe Leu Leu Cys Thr Val
225                 230                 235                 240
Ile Tyr Phe His Gln Tyr Thr His Lys Val Val Gly Ala Ala Val Gly
                245                 250                 255
Thr Phe Ala Trp Tyr Leu Thr Tyr Gly Ser Trp Tyr His Gln Ser Trp
                260                 265                 270
Ser Pro Gly Ser Pro Gly His Gly Leu Phe Pro Arg Pro His Ser Ser
                275                 280                 285
Arg Lys His Asn
    290

<210> SEQ ID NO 19
<211> LENGTH: 292
<212> TYPE: PRT
<213> ORGANISM: B.taurus
<220> FEATURE:
<221> NAME/KEY: misc_feature
<223> OTHER INFORMATION: FIT1

<400> SEQUENCE: 19

Met Glu Arg Gly Pro Val Val Gly Ala Gly Arg Gly Ala Gly Ala Arg
1               5                   10                  15
Ile Arg Ala Leu Leu Gly Gly Leu Val Arg Val Leu Leu Trp Val Ala
                20                  25                  30
Ser Ala Leu Leu Tyr Phe Gly Ser Glu Gln Ala Ala Arg Leu Leu Gly
            35                  40                  45
Ser Pro Cys Leu Arg Arg Leu Tyr His Ala Trp Leu Ala Ala Val Val
        50                  55                  60
Ile Phe Gly Pro Leu Leu Gln Phe His Val Asn Pro Arg Thr Ile Phe
65                  70                  75                  80
Ala Ser His Gly Asn Phe Phe Asn Ile Lys Phe Val Asn Ser Ala Trp
                85                  90                  95
Gly Trp Thr Cys Thr Phe Leu Gly Gly Phe Val Leu Val Val Phe
                100                 105                 110
Leu Ala Thr Arg Arg Val Ala Val Thr Ala Arg His Leu Ser Arg Leu
            115                 120                 125
Val Val Gly Ala Ala Val Trp Arg Gly Ala Gly Arg Ala Phe Leu Leu
    130                 135                 140
Ile Glu Asp Leu Thr Gly Ser Cys Phe Glu Pro Leu Pro Gln Gly Leu
145                 150                 155                 160
Leu Leu His Glu Leu Pro Asp Arg Arg Ser Cys Leu Ala Ala Gly His
                165                 170                 175
Gln Trp Arg Gly Tyr Thr Val Ser Ser His Thr Phe Leu Leu Thr Phe
                180                 185                 190
```

```
Cys Cys Leu Leu Met Ala Glu Glu Ala Ala Val Phe Ala Lys Tyr Leu
        195                 200                 205

Ala His Gly Leu Pro Ala Gly Ala Pro Leu Arg Leu Val Phe Leu Leu
    210                 215                 220

Asn Val Leu Leu Leu Gly Leu Trp Asn Phe Leu Leu Cys Thr Val
225                 230                 235                 240

Ile Tyr Phe His Gln Tyr Thr His Lys Val Val Gly Ala Ala Val Gly
                245                 250                 255

Thr Phe Ala Trp Tyr Leu Thr Tyr Gly Ser Trp Tyr His Gln Pro Trp
            260                 265                 270

Ser Pro Gly Ser Pro Gly His Gly Leu Phe Pro Arg Pro His Ser Ile
        275                 280                 285

His Lys His Asn
    290

<210> SEQ ID NO 20
<211> LENGTH: 47
<212> TYPE: DNA
<213> ORGANISM: artificial sequence
<220> FEATURE:
<223> OTHER INFORMATION: shRNA control

<400> SEQUENCE: 20
caccgaattc tccgaacgtg tcacgcgaac gtgacacgtt cggagaa                47

<210> SEQ ID NO 21
<211> LENGTH: 50
<212> TYPE: DNA
<213> ORGANISM: artificial sequence
<220> FEATURE:
<223> OTHER INFORMATION: shRNA FIT2

<400> SEQUENCE: 21
caccgcacca tgtttggttt gttggcgaac caacaaacca acatggtgc              50

<210> SEQ ID NO 22
<211> LENGTH: 76
<212> TYPE: DNA
<213> ORGANISM: Artificial Sequence
<220> FEATURE:
<223> OTHER INFORMATION: Primer

<400> SEQUENCE: 22
cattagcccc tcctcagcct ccagcagagc agacagttag tggggagggg ccatggccga  60
tcatattcaa taaccc                                                  76

<210> SEQ ID NO 23
<211> LENGTH: 69
<212> TYPE: DNA
<213> ORGANISM: Artificial Sequence
<220> FEATURE:
<223> OTHER INFORMATION: Primer

<400> SEQUENCE: 23
tgtttgcgca ttgagcggga tcgagggaag agcccgtggc ctgggatccc ataacttcgt  60
atagcatac                                                          69

<210> SEQ ID NO 24
<211> LENGTH: 32
<212> TYPE: DNA
<213> ORGANISM: Artificial Sequence
<220> FEATURE:
<223> OTHER INFORMATION: Primer
```

<210> SEQ ID NO 24

<400> SEQUENCE: 24
gttgaccgtc agtcctcaaa ctggcccctt gc                                        32

<210> SEQ ID NO 25
<211> LENGTH: 31
<212> TYPE: DNA
<213> ORGANISM: Artificial Sequence
<220> FEATURE:
<223> OTHER INFORMATION: Primer

<400> SEQUENCE: 25
gcttggctgg acgtaaactc ctcttcagac c                                         31

<210> SEQ ID NO 26
<211> LENGTH: 33
<212> TYPE: DNA
<213> ORGANISM: Artificial Sequence
<220> FEATURE:
<223> OTHER INFORMATION: Primer

<400> SEQUENCE: 26
gaaaagaatc ggaggagaca gagccaggcc tgg                                       33

<210> SEQ ID NO 27
<211> LENGTH: 31
<212> TYPE: DNA
<213> ORGANISM: Artificial Sequence
<220> FEATURE:
<223> OTHER INFORMATION: Primer

<400> SEQUENCE: 27
gaaccagctg gggctcgact agagcttgcg g                                         31

<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28
acacaagttt tgcacagaca tagatgcagg                                           30

<210> SEQ ID NO 29
<211> LENGTH: 38
<212> TYPE: DNA
<213> ORGANISM: Artificial Sequence
<220> FEATURE:
<223> OTHER INFORMATION: Primer

<400> SEQUENCE: 29
caacttcaca cagcctagaa tcatctgaga ggagaacc                                  38

<210> SEQ ID NO 30
<211> LENGTH: 73
<212> TYPE: DNA
<213> ORGANISM: Artificial Sequence
<220> FEATURE:
<223> OTHER INFORMATION: Primer

<400> SEQUENCE: 30
acacaagttt tgcacagaca tagatgcagg taaaatatac ataagtaagc gaacaactcc          60
gccgcgcgcg ctc                                                             73

```
<210> SEQ ID NO 31
<211> LENGTH: 70
<212> TYPE: DNA
<213> ORGANISM: Artificial Sequence
<220> FEATURE:
<223> OTHER INFORMATION: Primer

<400> SEQUENCE: 31
caacttcaca cagcctagaa tcatctgaga ggagaacctc aatggaggaa gagtaaactt      60
ggtctgacag                                                            70

<210> SEQ ID NO 32
<211> LENGTH: 31
<212> TYPE: DNA
<213> ORGANISM: Artificial Sequence
<220> FEATURE:
<223> OTHER INFORMATION: Primer

<400> SEQUENCE: 32
caggctgctc ttcaggagta tatctgggtt c                                    31

<210> SEQ ID NO 33
<211> LENGTH: 32
<212> TYPE: DNA
<213> ORGANISM: Artificial Sequence
<220> FEATURE:
<223> OTHER INFORMATION: Primer

<400> SEQUENCE: 33
ccgggagcca ccttcttctc caaccgtccc gg                                   32

<210> SEQ ID NO 34
<211> LENGTH: 31
<212> TYPE: DNA
<213> ORGANISM: Artificial Sequence
<220> FEATURE:
<223> OTHER INFORMATION: Primer

<400> SEQUENCE: 34
agttacagac aattgtgagt tgccatgtgg c                                    31

<210> SEQ ID NO 35
<211> LENGTH: 32
<212> TYPE: DNA
<213> ORGANISM: Artificial Sequence
<220> FEATURE:
<223> OTHER INFORMATION: Primer

<400> SEQUENCE: 35
ctgagatagg tgcctcactg attaagcatt gg                                   32

<210> SEQ ID NO 36
<211> LENGTH: 31
<212> TYPE: DNA
<213> ORGANISM: Artificial Sequence
<220> FEATURE:
<223> OTHER INFORMATION: Primer

<400> SEQUENCE: 36
gtaccccaca gtcacatcca taggacaatc c                                    31

<210> SEQ ID NO 37
<211> LENGTH: 32
<212> TYPE: DNA
<213> ORGANISM: Artificial Sequence
<220> FEATURE:
<223> OTHER INFORMATION: Primer
```

<400> SEQUENCE: 37
ctaactgtct gctctgctgg aggctgagga gg                                    32

<210> SEQ ID NO 38
<211> LENGTH: 70
<212> TYPE: DNA
<213> ORGANISM: Artificial Sequence
<220> FEATURE:
<223> OTHER INFORMATION: Primer

<400> SEQUENCE: 38
gctcagagga ggcagacatg gcagatgttg ctgtatctgg cctaatgaac ccgatcatat      60
tcaataaccc                                                            70

<210> SEQ ID NO 39
<211> LENGTH: 69
<212> TYPE: DNA
<213> ORGANISM: Artificial Sequence
<220> FEATURE:
<223> OTHER INFORMATION: Primer

<400> SEQUENCE: 39
acgtgggaat cctattagcc attgtcctcc tgtccctatg tccttctctt ataacttcgt      60
atagcatac                                                             69

<210> SEQ ID NO 40
<211> LENGTH: 32
<212> TYPE: DNA
<213> ORGANISM: Artificial Sequence
<220> FEATURE:
<223> OTHER INFORMATION: Primer

<400> SEQUENCE: 40
taagaataga gtgtaagggt ggtagttgtt cc                                    32

<210> SEQ ID NO 41
<211> LENGTH: 32
<212> TYPE: DNA
<213> ORGANISM: Artificial Sequence
<220> FEATURE:
<223> OTHER INFORMATION: Primer

<400> SEQUENCE: 41
ccttcatcct tccccactcg tagtggctgg tc                                    32

<210> SEQ ID NO 42
<211> LENGTH: 73
<212> TYPE: DNA
<213> ORGANISM: Artificial Sequence
<220> FEATURE:
<223> OTHER INFORMATION: Primer

<400> SEQUENCE: 42
acagtcccag ctcccatggc actcctcact gtaaatataa ctcgccgatg gaacaactcc      60
gccgcgcgcg ctc                                                        73

<210> SEQ ID NO 43
<211> LENGTH: 70
<212> TYPE: DNA
<213> ORGANISM: Artificial Sequence
<220> FEATURE:
<223> OTHER INFORMATION: Primer

<400> SEQUENCE: 43

```
gctggcctgg aactcacttt atagagaggg ctggttttga acctgtgttg gagtaaactt    60
ggtctgacag                                                          70
```

<210> SEQ ID NO 44
<211> LENGTH: 32
<212> TYPE: DNA
<213> ORGANISM: Artificial Sequence
<220> FEATURE:
<223> OTHER INFORMATION: Primer

<400> SEQUENCE: 44

```
cttcgtgcac actagtcaag catcctacca ac                                 32
```

<210> SEQ ID NO 45
<211> LENGTH: 31
<212> TYPE: DNA
<213> ORGANISM: Artificial Sequence
<220> FEATURE:
<223> OTHER INFORMATION: Primer

<400> SEQUENCE: 45

```
ctattttgaa acaggatctc ttacgtgacc c                                  31
```

<210> SEQ ID NO 46
<211> LENGTH: 62
<212> TYPE: DNA
<213> ORGANISM: Artificial Sequence
<220> FEATURE:
<223> OTHER INFORMATION: Primer

<400> SEQUENCE: 46

```
taatgaacca ggagcccagc agcctggcac gccaattgtt tagggtagc gatatcgaat     60 tc                                                                  62
```

<210> SEQ ID NO 47
<211> LENGTH: 62
<212> TYPE: DNA
<213> ORGANISM: Artificial Sequence
<220> FEATURE:
<223> OTHER INFORMATION: Primer

<400> SEQUENCE: 47

```
gaaaaaaga aagaaagaaa gcgagcaagc tttagttcaa gctacaagac agtggatcca     60
cc                                                                  62
```

<210> SEQ ID NO 48
<211> LENGTH: 31
<212> TYPE: DNA
<213> ORGANISM: Artificial Sequence
<220> FEATURE:
<223> OTHER INFORMATION: Primer

<400> SEQUENCE: 48

```
accacatggt ggctcataac catctgtcat g                                  31
```

<210> SEQ ID NO 49
<211> LENGTH: 32
<212> TYPE: DNA
<213> ORGANISM: Artificial Sequence
<220> FEATURE:
<223> OTHER INFORMATION: Primer

<400> SEQUENCE: 49

```
taagaataga gtgtaagggt ggtagttgtt cc                                 32
```

<210> SEQ ID NO 50
<211> LENGTH: 62
<212> TYPE: DNA
<213> ORGANISM: Artificial Sequence
<220> FEATURE:
<223> OTHER INFORMATION: Primer

<400> SEQUENCE: 50
acaagcttag ttggcagact ctgctggcgg tgccaccatg ttgccagcag gatatcgaat    60
tc    62

<210> SEQ ID NO 51
<211> LENGTH: 62
<212> TYPE: DNA
<213> ORGANISM: Artificial Sequence
<220> FEATURE:
<223> OTHER INFORMATION: Primer

<400> SEQUENCE: 51
acgatgaggc aggctgctct ccctctgctg agcctcagct ctccctctgg agtggatcca    60
cc    62

<210> SEQ ID NO 52
<211> LENGTH: 31
<212> TYPE: DNA
<213> ORGANISM: Artificial Sequence
<220> FEATURE:
<223> OTHER INFORMATION: Primer

<400> SEQUENCE: 52
agtgagttcc agaacacgca gggctacaca g    31

<210> SEQ ID NO 53
<211> LENGTH: 33
<212> TYPE: DNA
<213> ORGANISM: Artificial Sequence
<220> FEATURE:
<223> OTHER INFORMATION: Primer

<400> SEQUENCE: 53
gctcagcaga gggagagcag cctgcctgat cgt    33

<210> SEQ ID NO 54
<211> LENGTH: 4823
<212> TYPE: DNA
<213> ORGANISM: Artificial Sequence
<220> FEATURE:
<223> OTHER INFORMATION: Plasmid

<400> SEQUENCE: 54
ttaatatttt gttaaaattc gcgttaaatt tttgttaaat cagctcattt tttaaccaat    60
aggccgaaat cggcaaaatc ccttataaat caaaagaata gaccgagata gggttgagtg    120
ttgttccagt ttggaacaag agtccactat taaagaacgt ggactccaac gtcaaagggc    180
gaaaaaccgt ctatcagggc gatggcccac tacgtgaacc atcaccctaa tcaagttttt    240
tggggtcgag gtgccgtaaa gcactaaatc ggaaccctaa agggagcccc cgatttagag    300
cttgacgggg aaagccggcg aacgtggcga gaaaggaagg gaagaaagcg aaaggagcgg    360
gcgctagggc gctggcaagt gtagcggtca cgctgcgcgt aaccaccaca cccgccgcgc    420
ttaatgcgcc gctacagggc gcgtcaggtg gcacttttcg gggaaatgtg cgcggaaccc    480
ctatttgttt atttttctaa atacattcaa atatgtatcc gctcatgaga caataaccct    540

```
gataaatgct tcaataatat tgaaaaagga agagtatgag tattcaacat ttccgtgtcg     600
cccttattcc cttttttgcg gcattttgcc ttcctgtttt tgctcaccca gaaacgctgg     660
tgaaagtaaa agatgctgaa gatcagttgg gtgcacgagt gggttacatc gaactggatc     720
tcaacagcgg taagatcctt gagagttttc gccccgaaga acgttttcca atgatgagca     780
cttttaaagt tctgctatgt ggcgcggtat tatcccgtat tgacgccggg caagagcaac     840
tcggtcgccg catacactat tctcagaatg acttggttga gtactcacca gtcacagaaa     900
agcatcttac ggatggcatg acagtaagag aattatgcag tgctgccata accatgagtg     960
ataacactgc ggccaactta cttctgacaa cgatcggagg accgaaggag ctaaccgctt    1020
ttttgcacaa catgggggat catgtaactc gccttgatcg ttgggaaccg gagctgaatg    1080
aagccatacc aaacgacgag cgtgacacca cgatgcctgt agcaatggca acaacgttgc    1140
gcaaactatt aactggcgaa ctacttactc tagcttcccg gcaacaatta atagactgga    1200
tggaggcgga taaagttgca ggaccacttc tgcgctcggc ccttccggct ggctggttta    1260
ttgctgataa atctggagcc ggtgagcgtg ggtctcgcgg tatcattgca gcactggggc    1320
cagatggtaa gccctcccgt atcgtagtta tctacacgac ggggagtcag gcaactatgg    1380
atgaacgaaa tagacagatc gctgagatag gtgcctcact gattaagcat tggtaactgt    1440
cagaccaagt ttactcatat atactttaga ttgatttaaa acttcatttt taatttaaaa    1500
ggatctaggt gaagatcctt tttgataatc tcatgaccaa aatcccttaa cgtgagtttt    1560
cgttccactg agcgtcagac cccgtagaaa agatcaaagg atcttcttga gatcctttt    1620
ttctgcgcgt aatctgctgc ttgcaaacaa aaaaaccacc gctaccagcg gtggtttgtt    1680
tgccggatca agagctacca actctttttc cgaaggtaac tggcttcagc agagcgcaga    1740
taccaaatac tgttcttcta gtgtagccgt agttaggcca ccacttcaag aactctgtag    1800
caccgcctac atacctcgct ctgctaatcc tgttaccagt ggctgctgcc agtggcgata    1860
agtcgtgtct taccgggttg gactcaagac gatagttacc ggataaggcg cagcggtcgg    1920
gctgaacggg gggttcgtgc acacagccca gcttggagcg aacgacctac accgaactga    1980
gatacctaca gcgtgagcta tgagaaagcg ccacgcttcc cgaagggaga aaggcggaca    2040
ggtatccggt aagcggcagg gtcggaacag gagagcgcac gagggagctt ccaggggaa    2100
acgcctggta tctttatagt cctgtcgggt ttcgccacct ctgacttgag cgtcgatttt    2160
tgtgatgctc gtcaggggg cggagcctat ggaaaaacgc cagcaacgcg gcctttttac    2220
ggttcctggc cttttgctgg ccttttgctc acatgttctt tcctgcgtta tcccctgatt    2280
ctgtggataa ccgtattacc gcctttgagt gagctgatac cgctcgccgc agccgaacga    2340
ccgagcgcag cgagtcagtg agcgaggaag cggaagagcg cccaatacgc aaaccgcctc    2400
tccccgcgcg ttggccgatt cattaatgca gctggcacga caggtttccc gactggaaag    2460
cgggcagtga gcgcaacgca attaatgtga gttagctcac tcattaggca ccccaggctt    2520
tacactttat gcttccggct cgtatgttgt gtggaattgt gagcggataa caatttcaca    2580
caggaaacag ctatgaccat gattacgcca agctcgaaat taaccctcac taaagggaac    2640
aaaagctggt accgggcccc ccctcgaggt cgacctgcag ccaagctatc gaattcctgc    2700
agcccaattc cgatcatatt caataaccct aatataact tcgtataatg tatgctatac    2760
gaagttatta ggtctgaaga ggagtttacg tccagccaag ctagcttggc tgcaggtcgt    2820
cgaaattcta ccgggtaggg gaggcgcttt tcccaaggca gtctggagca tgcgctttag    2880
cagccccgct gggcacttgg cgctacacaa gtggcctctg gcctcgcaca cattccacat    2940
```

```
ccaccggtag cgccaaccg gctccgttct tggtggccc cttcgcgcca ccttctactc    3000
ctcccctagt caggaagttc cccccgccc cgcagctcgc gtcgtgcagg acgtgacaaa    3060
tggaagtagc acgtctcact agtctcgtgc agatggacag caccgctgag caatggaagc    3120
gggtaggcct ttggggcagc ggccaatagc agctttgctc cttcgctttc tgggctcaga    3180
ggctgggaag gggtgggtcc gggggcgggc tcagggggcgg gctcaggggc ggggcgggcg    3240
cccgaaggtc ctccggaggc ccggcattct gcacgcttca aaagcgcacg tctgccgcgc    3300
tgttctcctc ttcctcatct ccgggccttt cgacctgcag cctgttgaca attaatcatc    3360
ggcatagtat atcggcatag tataatacga caaggtgagg aactaaacca tgggatcggc    3420
cattgaacaa gatggattgc acgcaggttc tccggccgct tgggtggaga ggctattcgg    3480
ctatgactgg gcacaacaga caatcggctg ctctgatgcc gccgtgttcc ggctgtcagc    3540
gcaggggcgc ccggttcttt ttgtcaagac cgacctgtcc ggtgccctga atgaactgca    3600
ggacgaggca gcgcggctat cgtggctggc cacgacgggc gttccttgcg cagctgtgct    3660
cgacgttgtc actgaagcgg gaagggactg gctgctattg ggcgaagtgc cggggcagga    3720
tctcctgtca tctcaccttg ctcctgccga gaaagtatcc atcatggctg atgcaatgcg    3780
gcggctgcat acgcttgatc cggctacctg cccattcgac caccaagcga acatcgcat    3840 cgagcgagca cgtactcgga tggaagccgg tcttgtcgat caggatgatc tggacgaaga    3900
gcatcagggg ctcgcgccag ccgaactgtt cgccaggctc aaggcgcgca tgcccgacgg    3960
cgatgatctc gtcgtgaccc atggcgatgc ctgcttgccg aatatcatgg tggaaaatgg    4020
ccgcttttct ggattcatcg actgtggccg gctgggtgtg gcggaccgct atcaggacat    4080
agcgttggct acccgtgata ttgctgaaga gcttggcggc gaatgggctg accgcttcct    4140
cgtgctttac ggtatcgccg ctcccgattc gcagcgcatc gccttctatc gccttcttga    4200
cgagttcttc tgagggggatc aattctctag agctcgctga tcagcctcga ctgtgccttc    4260
tagttgccag ccatctgttg tttgccccctc ccccgtgcct tccttgaccc tggaaggtgc    4320
cactcccact gtcctttcct aataaaatga ggaaattgca tcgcattgtc tgagtaggtg    4380
tcattctatt ctgggggtg gggtggggca ggacagcaag ggggaggatt gggaagacaa    4440
tagcaggcat gctggggatg cggtgggctc tatggcttct gaggcggaaa gaaccagctg    4500
gggctcgact agagcttgcg gaacccttaa tataacttcg tataatgtat gctatacgaa    4560
gttattaggt ccctcgaggg gatccactag ttctagagcg gccgccaccg cggtggagct    4620
ccaattcgcc ctatagtgag tcgtattaca attcactggc cgtcgtttta caacgtcgtg    4680
actgggaaaa ccctggcgtt acccaactta atcgccttgc agcacatccc cctttcgcca    4740
gctggcgtaa tagcgaagag gcccgcaccg atcgcccttc ccaacagttg cgcagcctga    4800
atggcgaatg gaaattgtaa gcg                                            4823
```

<210> SEQ ID NO 55
<211> LENGTH: 4832
<212> TYPE: DNA
<213> ORGANISM: Artificial Sequence
<220> FEATURE:
<223> OTHER INFORMATION: Plasmid

<400> SEQUENCE: 55

```
ctaaattgta agcgttaata ttttgttaaa attcgcgtta aatttttgtt aaatcagctc     60
attttttaac caataggccg aaatcggcaa aatcccttat aaatcaaaag aatagaccga    120
gatagggttg agtgttgttc cagtttggaa caagagtcca ctattaaaga acgtggactc    180
```

```
caacgtcaaa gggcgaaaaa ccgtctatca gggcgatggc ccactacgtg aaccatcacc      240
ctaatcaagt ttttttggggt cgaggtgccg taaagcacta aatcggaacc ctaaagggag      300
cccccgattt agagcttgac ggggaaagcc ggcgaacgtg gcgagaaagg aagggaagaa      360
agcgaaagga gcgggcgcta gggcgctggc aagtgtagcg gtcacgctgc gcgtaaccac      420
cacacccgcc gcgcttaatg cgccgctaca gggcgcgtcc cattcgccat tcaggctgcg      480
caactgttgg gaagggcgat cggtgcgggc ctcttcgcta ttacgccagc tggcgaaagg      540
gggatgtgct gcaaggcgat taagttgggt aacgccaggg ttttcccagt cacgacgttg      600
taaaacgacg gccagtgaat tgtaatacga ctcactatag ggcgaattgg gtaccgggcc      660 cccctcgag tcgacggta tcgataagct tgatatcgaa ttcgaagtt cctattctct       720 agaaagtata ggaacttcag gtctgaagag gagtttacgt ccagccaagc tagcttggct      780
gcaggtcgtc gaaattctac cgggtagggg aggcgctttt cccaaggcag tctggagcat      840
gcgctttagc agccccgctg gcacttggc gctacacaag tggcctctgg cctcgcacac      900
attccacatc caccggtagg cgccaaccgg ctccgttctt tggtggcccc ttcgcgccac      960
cttctactcc tcccctagtc aggaagttcc cccccgcccc gcagctcgcg tcgtgcagga    1020
cgtgacaaat ggaagtagca cgtctcacta gtctcgtgca gatggacagc accgctgagc    1080 aatgaagcg gtaggccctt ggggcagcg gccaatagca gctttgctcc ttcgcttttct    1140 gggctcagag gctgggaagg ggtgggtccg ggggcgggct cagggcggg ctcagggcg    1200 gggcgggcgc ccgaaggtcc tccggaggcc cggcattctg cacgcttcaa aagcgcacgt    1260
ctgccgcgct gttctcctct tcctcatctc cgggcctttc gacctgcagc ctgttgacaa    1320
ttaatcatcg gcatagtata tcggcatagt ataatacgac aaggtgagga actaaaccat    1380
gggatcggcc attgaacaag atggattgca cgcaggttct ccggccgctt gggtggagag    1440
gctattcggc tatgactggg cacaacagac aatcggctgc tctgatgccg ccgtgttccg    1500
gctgtcagcg caggggcgcc cggttctttt tgtcaagacc gacctgtccg gtgccctgaa    1560
tgaactgcag gacgaggcag cgcggctatc gtggctggcc acgacgggcg ttccttgcgc    1620
agctgtgctc gacgttgtca ctgaagcggg aagggactgg ctgctattgg gcgaagtgcc    1680
ggggcaggat ctcctgtcat ctcacccttgc tcctgccgag aaagtatcca tcatggctga    1740
tgcaatgcgg cggctgcata cgcttgatcc ggctacctgc ccattcgacc accaagcgaa    1800
acatcgcatc gagcgagcac gtactcggat ggaagccggt cttgtcgatc aggatgatct    1860
ggacgaagag catcaggggc tcgcgccagc cgaactgttc gccaggctca aggcgcgcat    1920
gcccgacggc gatgatctcg tcgtgaccca tggcgatgcc tgcttgccga atatcatggt    1980
ggaaaatggc cgcttttctg gattcatcga ctgtggccgg ctgggtgtgg cggaccgcta    2040
tcaggacata gcgttggcta cccgtgatat tgctgaagag cttggcggcg aatgggctga    2100
ccgcttcctc gtgctttacg gtatcgccgc tcccgattcg cagcgcatcg ccttctatcg    2160
ccttcttgac gagttcttct gaggggatca attctctaga gctcgctgat cagcctcgac    2220
tgtgccttct agttgccagc catctgttgt ttgcccctcc cccgtgcctt ccttgaccct    2280
ggaaggtgcc actcccactg tccttttccta ataaaatgag gaaattgcat cgcattgtct    2340
gagtaggtgt cattctattc tggggggtgg ggtggggcag gacagcaagg gggaggattg    2400
ggaagacaat agcaggcatg ctggggatgc ggtgggctct atggcttctg aggcggaaag    2460
aaccagctgg ggctcgacta gagcttgcgg aaccccttga gttcctattt ctctagaaag    2520
tataggaact tcatcagtca ggtacataat ataacttcgt ataatgtatg ctatacgaag    2580
```

```
ttattaggtg gatccactag ttctagagcg gccgccaccg cggtggagct ccagcttttg   2640 ttcccttag tgagggttaa tttcgagctt ggcgtaatca tggtcatagc tgtttcctgt    2700
gtgaaattgt tatccgctca caattccaca acacatacga gccggaagca taaagtgtaa   2760 agcctgggt gcctaatgag tgagctaact cacattaatt gcgttgcgct cactgcccgc    2820
tttccagtcg ggaaacctgt cgtgccagct gcattaatga atcggccaac gcgcggggag   2880
aggcggtttg cgtattgggc gctcttccgc ttcctcgctc actgactcgc tgcgctcggt   2940
cgttcggctg cggcgagcgg tatcagctca ctcaaaggcg gtaatacggt tatccacaga   3000
atcaggggat aacgcaggaa agaacatgtg agcaaaaggc cagcaaaagg ccaggaaccg   3060
taaaaaggcc gcgttgctgg cgttttcca taggctccgc cccctgacg agcatcacaa    3120 aaatcgacgc tcaagtcaga ggtggcgaaa cccgacagga ctataaagat accaggcgtt   3180
tccccctgga agctccctcg tgcgctctcc tgttccgacc ctgccgctta ccggatacct   3240
gtccgccttt ctcccttcgg gaagcgtggc gctttctcat agctcacgct gtaggtatct   3300
cagttcggtg taggtcgttc gctccaagct gggctgtgtg cacgaacccc ccgttcagcc   3360
cgaccgctgc gccttatccg gtaactatcg tcttgagtcc aacccggtaa gacacgactt   3420
atcgccactg gcagcagcca ctggtaacag gattagcaga gcgaggtatg taggcggtgc   3480
tacagagttc ttgaagtggt ggcctaacta cggctacact agaagaacag tatttggtat   3540
ctgcgctctg ctgaagccag ttaccttcgg aaaaagagtt ggtagctctt gatccggcaa   3600
acaaaccacc gctggtagcg gtggtttttt tgtttgcaag cagcagatta cgcgcagaaa   3660
aaaaggatct caagaagatc ctttgatctt ttctacgggg tctgacgctc agtggaacga   3720
aaactcacgt taagggattt tggtcatgag attatcaaaa aggatcttca cctagatcct   3780
tttaaattaa aaatgaagtt ttaaatcaat ctaaagtata tatgagtaaa cttggtctga   3840
cagttaccaa tgcttaatca gtgaggcacc tatctcagcg atctgtctat ttcgttcatc   3900
catagttgcc tgactccccg tcgtgtagat aactacgata cgggagggct taccatctgg   3960
ccccagtgct gcaatgatac cgcgagaccc acgctcaccg gctccagatt tatcagcaat   4020
aaaccagcca gccggaaggg ccgagcgcag aagtggtcct gcaactttat ccgcctccat   4080
ccagtctatt aattgttgcc gggaagctag agtaagtagt tcgccagtta atagtttgcg   4140
caacgttgtt gccattgcta caggcatcgt ggtgtcacgc tcgtcgtttg gtatggcttc   4200
attcagctcc ggttcccaac gatcaaggcg agttacatga tcccccatgt tgtgcaaaaa   4260
agcggttagc tccttcggtc ctccgatcgt tgtcagaagt aagttggccg cagtgttatc   4320
actcatggtt atggcagcac tgcataattc tcttactgtc atgccatccg taagatgctt   4380
ttctgtgact ggtgagtact caaccaagtc attctgagaa tagtgtatgc ggcgaccgag   4440
ttgctcttgc ccggcgtcaa tacgggataa taccgcgcca catagcagaa ctttaaaagt   4500
gctcatcatt ggaaaacgtt cttcggggcg aaaactctca aggatcttac cgctgttgag   4560
atccagttcg atgtaaccca ctcgtgcacc caactgatct tcagcatctt ttactttcac   4620
cagcgtttct gggtgagcaa aaacaggaag gcaaaatgcc gcaaaaaagg gaataagggc   4680
gacacggaaa tgttgaatac tcatactctt cctttttcaa tattattgaa gcatttatca   4740
gggttattgt ctcatgagcg gatacatatt tgaatgtatt tagaaaaata aacaaatagg   4800
ggttccgcgc acatttcccc gaaaagtgcc ac                                 4832

<210> SEQ ID NO 56
<211> LENGTH: 39
```

```
<212> TYPE: DNA
<213> ORGANISM: artificial sequence
<220> FEATURE:
<223> OTHER INFORMATION: primer

<400> SEQUENCE: 56
caccatggag catctggagc gctgcgagtg gttgttgcg                         39

<210> SEQ ID NO 57
<211> LENGTH: 35
<212> TYPE: DNA
<213> ORGANISM: artificial sequence
<220> FEATURE:
<223> OTHER INFORMATION: primer

<400> SEQUENCE: 57
ttatttcttg taactatctt gcttcaaatt caaac                             35

<210> SEQ ID NO 58
<211> LENGTH: 35
<212> TYPE: DNA
<213> ORGANISM: artificial sequence
<220> FEATURE:
<223> OTHER INFORMATION: primer

<400> SEQUENCE: 58
tttcttgtaa ctatcttgct tcaaattcaa actac                             35
```